United States Patent [19]
Karimian et al.

[11] Patent Number: 6,114,537
[45] Date of Patent: Sep. 5, 2000

[54] PROCESS FOR SCAVENGING THIOLS

[75] Inventors: Khashayar Karimian, Mississauga; Tim F. Tam, Woodbridge; Denis Desilets, St-Jean-Sur-Richelieu, all of Canada; Sue Lee, Cedar Knolls, N.J.; Tullio Cappelletto, North York; Wanren Li, Etobicoke, both of Canada

[73] Assignee: Apotex Inc., Ontario, Canada

[21] Appl. No.: 08/803,651

[22] Filed: Feb. 21, 1997

Related U.S. Application Data

[63] Continuation-in-part of application No. 08/606,705, Feb. 26, 1996, abandoned.
[51] Int. Cl.$^7$ .................................................. C07D 285/08
[52] U.S. Cl. .......................... 548/130; 548/128; 548/129; 568/26
[58] Field of Search ................................. 548/130, 128, 548/129

[56] References Cited

PUBLICATIONS

Kihara, Synthesis 1990 (11) 1020–3 Abstract Only, Nov. 1990.
1,2,4–Thiadiazoles, Frederick Kurzer, Advances in Heterocyclic Chemistry, vol. 12, p. 286–398.
"Umsetzung von Mercapto–N–Heterocyclenmit Arylcyanaten" Journal f. prakt. Chemie. Band 320, Heft 4, 1978, S677–684, J.A. Barth, Leipzig.
"Spaltung von 1,2,4–thiadiazol–3–onen . . . ", Journal f. prakt, Chemie, Band 330, Heft 3, 1988 S 338–348, V E B J.A. Barth, Leipzig.
"Exchange, Elimination, and Ring Opening Reactions . . . ", Chem. Soc. Perkin Trans 1, 1985, 1007–1011.
"Acylierung Von Heterocyclen mit Kohlensaurederivaten–III", Martin & Tittlebach, vol. 39, No. 13–0, p. 2311–2313.
"Toxic Effects of a Fungicide, 5–Ethoxy–3–(Trichloromethyl) . . . " Dalvi & Howell, Bulletin of Environmental Contamination & Toxicology, vol. 17, No. 2, 1977.
"Imidazo [1,2–d]–1,2,4–thiadiazoles" Pentimalli, et al., Gazzetta Chimica Italiana, 107, 1977, p. 1–5.
"The Chemistry of o–phenylene di–isothiocyanate, Part 2 . . . ", Faull et al., p. 2587–2610.
"The Thiadiazoles" William R. Sherman, Abbott Laboratories, North Chicago, Illinois, p 542–619.
"Inhibitors of the Adeovirus Type 2 Proteinase Based on Substrate–Like Tetrapeptide Nitriles", Cornish et al., 1995 Bioorganic & Medicinal Chemistry Letters vol. 5, No. 1 pp 25–30.
"Potent Inactivation of Cathepsins S and L by Peptidyl . . . ", Biol. Chem. Hoope–Seyler, vol. 375, p. 343–347 May 1994, Bromme.
"Vinyl Sulfones as Mechanism–Based Cysteine Protease Inhibitors" Palmer et al., J. Med. Chem. 1995, 38, 3193–3196.
E64[trans–epoxycuccinyl–L–leucylamido–(4–guanidino) butane]. . . Gour–Salin et al., Biotechnology Research, Montreal CA, 389–91.
"Molecular Basis of the Action of Drugs and Toxic Substances" Proceedings International Symposium, San Francisco, CA, Apr. 23–26, 1987, Singer et al., p. 273–284.
"Streptonigrin . . . ", J. Med. Chem. 1986, 29, 1329–1340 (1986) Shaikh, et al.
"Chemical Reactions of Omeprazole & Omeprazole Analogs . . . " Brandstrom et al., Acta Chemica Scandinavica 43 (1989) 577–587.
"Chemical Reactions of Omeprazole & Omeprazole Analogs . . . " Brandstrom et al., Acta Chemica Scandinavica 43 (1989) 536–548.
"The Structure, Reactions, Synthesis, and Uses of Heterocyclic Compounds" Comprehensive Heterocyclic Chemistry II, A Review of the Literature 1982–1995, vol. 4, p. 307–354.

*Primary Examiner*—Robert Gerstl
*Attorney, Agent, or Firm*—Ridout & Maybee; Robert G. Hirons

[57] ABSTRACT

Thiols are trapped, and converted to disulfide compounds, by a process of reacting them with compounds containing a 1,2,4-thiadiazole ring structure carrying a substituent at position 3 of the thiadiazole ring, and being unsubstituted at position N-2. The process is useful pharmacologically, in inhibiting certain thiol-containing enzymes such as $H^+/K^+$-ATPase (the proton pump), and industrially, in selective removal of thiol compounds from gas or liquid mixtures.

5 Claims, 3 Drawing Sheets

PROCESS FOR SCAVENGING THIOLS

CROSS REFERENCE TO RELATED APPLICATION

This application is a continuation-in-part of U.S. patent application Ser. No. 08/606,705 filed Feb. 26, 1996, now abandoned.

FIELD OF THE INVENTION

This invention relates to chemical processes for trapping thiols, and selectively converting thiol compounds to disulfide compounds. It also relates to the use of certain thiadiazole compounds, some of which are novel, as thiol trapping agents, in selective reaction with thiols to convert them to disulfides.

BACKGROUND OF THE INVENTION AND PRIOR ART

Thiol compounds exist in many chemical and biochemical systems, and in many cases are undesirable or harmful compounds requiring selective removal or chemical conversion from the system. The thiol group SH (otherwise known as the mercaptan group or the sulfhydryl group) often confers malodorous properties on compounds containing it. Minerals such as mineral fuel deposits (oil, natural gas and coal, for example) are often contaminated with malodorous thiol compounds. Gaseous effluents from the extraction and refining of crude oil, gasification of coal and mining of natural gas are often contaminated with thiols, and require removal of thiols therefrom to meet environmental standards.

The manufacture of certain pharmaceutical products, for example cimetidine, ranitidine and nizatidine, involves the use of sulfur-containing reagents and the production of methyl mercaptan by-products. The current method of disposal of these products is by incineration, which leads to the production of sulfuric acid, discharged as a component of "acid rain". An improved method of trapping thiols in this context is also required.

Thiol trapping agents can be used in diagnostic processes to trap organic mercaptans. Also, they can be used as diagnostic reagents, for example, in the detection of sulfhydryl groups of proteins.

Of particular interest in connection with the present invention is the trapping of biochemical thiol compounds such as enzymes. Many enzymes contain active thiol groups, derived from their cysteine residues. Selective inhibition of the activity of such enzymes, reversibly or irreversibly, by reaction to modify their thiol groups, in a biological system, may thus form the basis of therapeutic treatment. Examples of such enzymes are Cathepsin B, Papain, $H^+/K^+$-ATPase, Interleukin β-1 Converting Enzyme, protein disulfide isomerase (HIV).

Cathepsin B and L have been implicated in a number of diseases, including progressive cartilage and bone degradation associated with arthritis. Inhibitors of these cathepsins have caused reduced inflammation and joint destruction in animal models of arthritis C. The calcium associated proteases calpain I and II have been associated with Alzheimer's disease.

Interleukin beta converting enzyme (M. Mullican et al., Bioorganic & Medicinal Chem. Lett., 1994, 2359) is a key target for drug discovery because of its key role in the release of the inflammatory protein, interleukin-1 b eta. Excessive levels of interleukin-1 beta are implicated in a wide variety of diseases including rheumatoid arthritis, psoriasis, inflammatory bowel disease, and insulin-dependent diabetes. Like thiol protease, its mechanism of action involves a cysteine resides at the active site.

Proposed reversible inhibitors of these enzymes include peptido aldehydes, nitrites, α-ketocarbonyl compounds. Proposed irreversible inhibitors include peptido halomethyl ketones, diazomethylketones, acyloxymethyl ketones, ketomethylsulfonium salts, epoxides and vinyl sulfones. Although these compounds are known to be thiol protease inhibitors, none of the structural types have found serious utilities as drug candidates.

The enzyme proton pump gastric $H^{s+}/K^+$-ATPase, also known as the proton pump, has been implicated in the development of peptic ulcers in mammals. This enzyme also contains active thiol groups, derived from their cysteine residues. The inhibition of this enzyme is one of the primary bases of treatment of peptic ulcer in humans. Thiol trapping agents can be used to inhibit the enzyme $H^+/K^+$-ATPase. An example of such compound is omeprazole.

SUMMARY OF THE INVENTION

The present invention provides novel processes for trapping thiol compounds, which comprises reacting them with certain thiadiazoles. Some of the thiadiazoles used in the present invention are novel chemical compounds. Others are known compounds, but not previously proposed for this use. The compounds used in the present invention are characterized by a 1,2,4-thiadiazole ring structure, substituted at position 3 but unsubstituted at position N-2.

One group of compounds for use in the process of the invention are 1,2,4-thiadiazolo-[4,5-a]benzimidazoles corresponding to the following formula I:

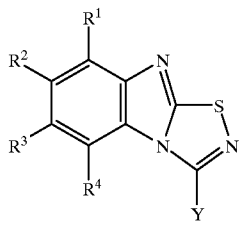

or pharmaceutically acceptable salts thereof, wherein:
$R^1$, $R^2$, $R^3$, $R^4$ are independently hydrogen, lower alkyl, halo, nitro, amino, hydroxy, lower alkoxy, lower alkylamino, lower dialkylamino, NR'R", OC(O)R', OC(O)OR', OC(O)NR'R", NR' (COR'), NHC(O)NR'RR", NHC(O)OR'.
R', R" are independently hydrogen, lower alkyl, aryl or lower arylalkyl, or R' and R" in NR'R" form with the N-atom a five or six-membered heterocyclic ring of formula

wherein n is 4 or 5, and y is selected from:
(1) groups of the formula:

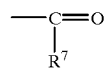

in which $R^7$ represents hydrogen, hydroxy, lower alkyl, lower cycloalkyl, lower alkoxy, lower alkenyl, lower alkynyl, aryl, lower arylalkyl, heterocyclyl, heterocyclyloxy, heterocyclyl-loweralkylene, a group NR'R" where R' and R" are independently selected from hydrogen, lower alkyl, aryl and lower arylalkyl, or R' and R" when taken together form with the N-atom a five or six membered heterocyclic ring N (CH$_2$)$_n$ wherein n=4 or 5; and a group ANR'R", AOR' wherein A is an amino acid residue or a peptide of 2 to 3 amino acid residues and R', R" have the same definition as above (2) heterocyclyl, lower alkylene-heterocyclyl, lower alkyl-lower alkylene heterocyclyl amino, lower alkylene-amino-heterocyclyl or amino-heterocyclyl, the heterocyclic ring being attached at any heteroatom or carbon atom which results in the creation of a stable structure, and the heterocyclic ring being optionally substituted with 1–3 substituents selected from lower alkyl; hydroxy; nitro; amino; lower alkylamino; di-lower alkylamino; lower alkoxy; lower alkyl substituted with 1–3 substituents s elected from hydroxy, lower alkylcarbamoyl, phenyl, halophenyl, heterocyclyl, carboxy and lower alkoxycarbonyl; lower acyl; lower alkocycarbonyl; lower alkylsulfonyl; amido; allyl; benzyl; phenyl optionally substituted with amino, halo hydroxy, lower alkoxy, lower alkyl, lower alkylamino or di-lower alkylamino; heterocyclyl optionally substituted with 1–3 substituents selected from nitro, hydroxy, lower alkoxy, lower alkyl, amino, halo, lower alkylamino, di-lower alkylamino; with the proviso that the heterocyclyl group Y is not 1-imidazolyl or substituted 1-imidazolyl;

(3) NR'R" or —CH$_2$—NR'R" wherein R', R" have the same definition as above;

(4) ANR'R", AOR' wherein A is an amino acid residue or a peptide of 2 to 3 amino acid residues and R', R" have the same definition as above (5) lower 2-(alkoxycarbonyl)alkyl (6) halo (7) groups of formula R$^8$—CHOH— wherein R$^8$ is hydrogen, lower alkyl, aryl, lower arylalkyl, lower cycloalkyl, lower alkenyl, lower alkynyl or heterocyclyl, the heterocyclic ring being attached at any heteroatom or carbon atom which results in the creation of a stable structure, (8) groups of formula R$^9$—C(=NOR$^{10}$)— wherein R$^{10}$ is hydrogen lower alkyl or lower arylalkyl, and R$^9$ is lower alkyl, aryl, lower arylalkyl, lower cycloalkyl, lower alkenyl, lower alkynyl or heterocyclyl, the heterocyclic ring being attached at any carbon atom which results in the creation of a stable structure;

(9) lower alkoxy, lower arylalkoxy, lower cycloalkoxy, lower heterocyclylalkoxy or heterocyclyloxy;

(10) lower alkylsulfonyl, lower alkylsulfinyl, arylsulfonyl, arylsulfinyl, lower arylalkylsulfonyl, lower arylalkylsulfinyl, heterocyclylsulfonyl, heterocyclylsulfinyl; optionally substituted with 1 to 2 substituents selected from lower alkyl, halo, nitro, hydroxy, lower alkoxy, or groups of formula NR'R", OC(O)R', OC(O)OR', OC(O)NR'R", NR'(COR'), NHC(O)NR'R", NHC(O)OR' where R' and R" have the meanings given above;

(11) groups of the formula —C(=NOH)COOR$^{11}$ wherein R$^{11}$ is lower alkyl;

(12) hydrogen, substituted lower alkyl, aryl, lower arylalkyl, lower cycloalkyl, each group being optionally substituted with 1 to 2 substituents selected from halo, nitro, amino, hydroxy, lower alkoxy, lower alkylamino, lower dialkylamino, NR'R", OC(O)R', OC(O)OR', OC(O)NR'R", NR'(COR'), NHC(O)NR'R", NHC(O)OR', with R' and R" having the meanings given above.

A second class of compounds for use in the process of the present invention is bicyclic compounds, namely imidazo[1,2-d]-1,2,4-thiadiazole of the following formula II:

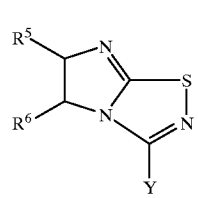

(II)

wherein R$^5$ and R$^6$ can have the same meanings as R$^1$, R$^2$, R$^3$ and R$^4$ in formula II above, and Y is as previously defined.

A third class of compounds for use in the present invention are 3-substituted, N-2-unsubstituted thiadiazoles of general formula III

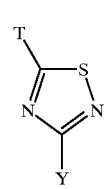

III where Y is as defined above, and T represents (a) a lower alkyl group, a lower alkylaryl group, a secondary or tertiary amine group, an amino acid residue or a heterocyclic group selected from azole, pyridine, piperadine, piperazine and morpholino;

or (b) a group —M[—AMA—] L where M is a chemical spacer group bonded to the thiadiazole nucleus and selected from

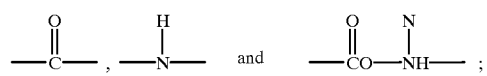

L is an N-terminal peptide protector group or a terminal group

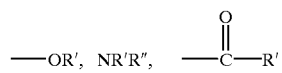

where R' and R" are as defined above; and —AMA— is an amino acid or peptide residue —[NH—CHA$^1$—CO]—$_n$ where A$^1$ is any one of the known amino acid α-substituents and n is an integer from 1 to 3;

or (c) —NHPh or a diphenyl-guanidine group of the formula

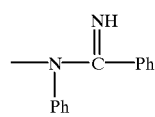

in which Ph represents phenyl optionally substituted with hydroxy, lower alkoxy or amino.

Novel, monocyclic compounds fo ruse in the present invention are 3-substituted, N-2-unsubstituted thiadiazoles of general formula IIIa

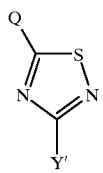

IIIa where Y' is lower alkyl, lower alkoxy, amino, carboxyl, lower alkoxycarbonyl or 1-piperazinyl optionally substituted at the 4-position with lower alkyl; lower alkyl substituted with 1 or 2 substituents selected from hydroxy, lower alkylcarbamoyl, phenyl, halophenyl, heterocyclyl, carboxy and lower alkoxycarbonyl; benzyl; phenyl optionally substituted with amino, halo, hydroxy, lower alkoxy, lower alkyl, lower alkylamino, or di(lower alkyl)amino; heterocyclyl optionally substituted with 1–3 substituents selected from nitro, amino, halo, hydroxy, lower alkoxy, lower alkyl, lower alkylamino, or di(lower alkyl)amino; 1,1-diphenylmethyl wherein both phenyl rings are optionally substituted with halo, amino, hydroxy or lower alkoxy; 2-pyridyl where the pyridyl ring is optionally substituted with 1–3 substituents selected from nitro, amino, halo, hydroxy, lower alkoxy, lower alkyl, lower alkylamino, or di(lower alkyl)amino; or a group —$CH_2$—CO—NH-loweralkyl;

and Q represents (a) a group —T[—AMA—] L where T is a chemical spacer group bonded to the thiadiazole nucleus and selected from

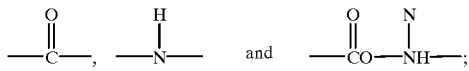

L is an N-terminal peptide protector group or a terminal group

where R' and R" are as defined above; and —AMA— is an amino acid or peptide residue —[NH—$CHA^1$—CO]—$_n$ where $A^1$ is any one of the known amino acid α-substituents and n is an integer from 1 to 3; with the provisos that, when Q is —NHPh, then Y' is not alkoxy; and when Y' is 4-substituted piperazinyl, Q is not a group —T—[AMA]—L.

Another aspect of the present invention is the use of compounds of the general formulae given above as thiol trapping agents in the reaction of thiol compounds therewith to form disulfide compounds. The reactions with thiol compounds take place in solution, e.g. in aqueous medium such as body fluids, at temperatures and under other appropriate conditions to maintain liquid solutions or suspensions of the reactants.

BRIEF REFERENCE TO THE DRAWINGS

DESCRIPTION OF THE PREFERRED EMBODIMENTS

Figure 1:
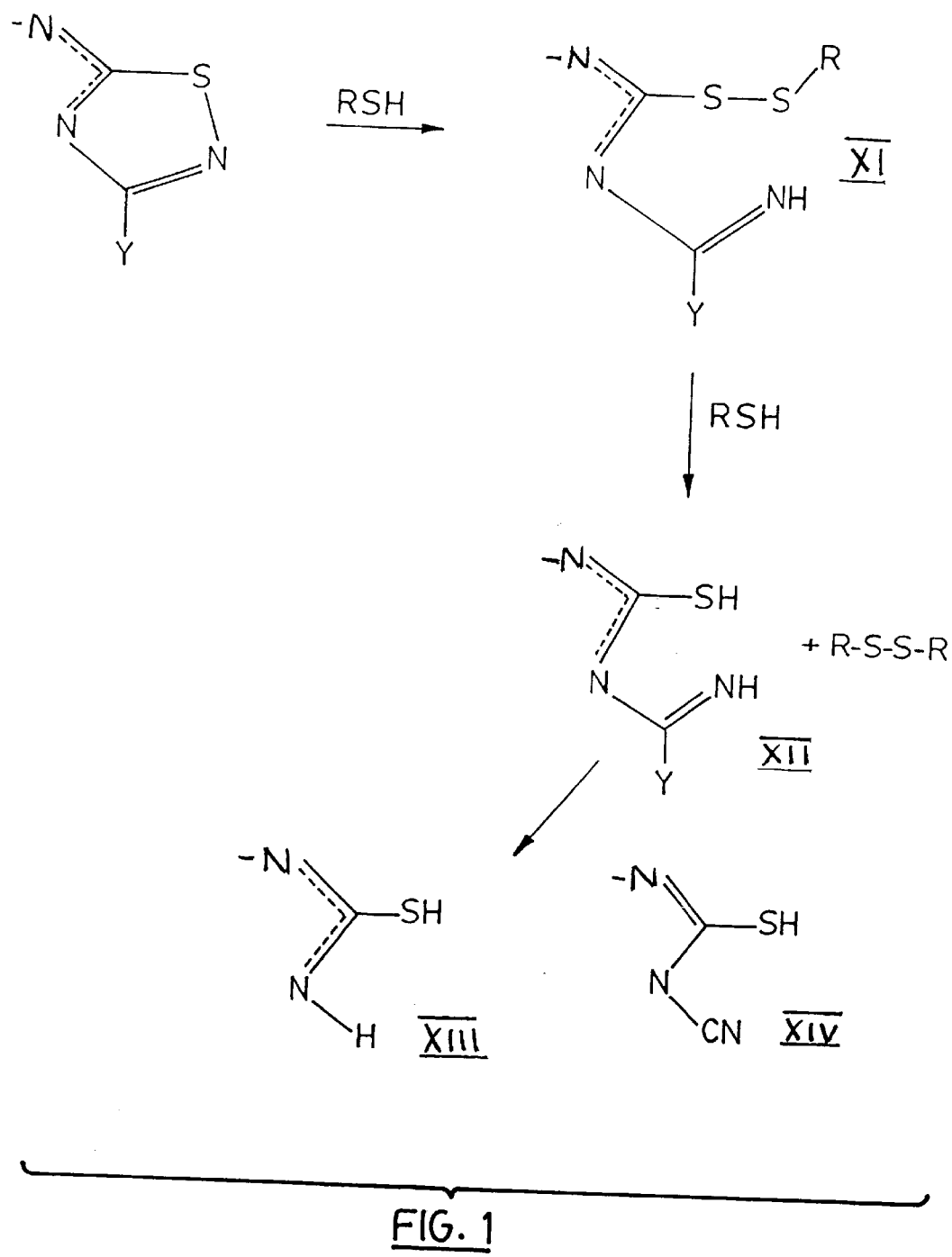
FIG. 1 is an illustration of the chemical interaction between thiol compounds and 3-substituted 1,2,4-thiadiazole compounds according to the present invention.
Figure 2:
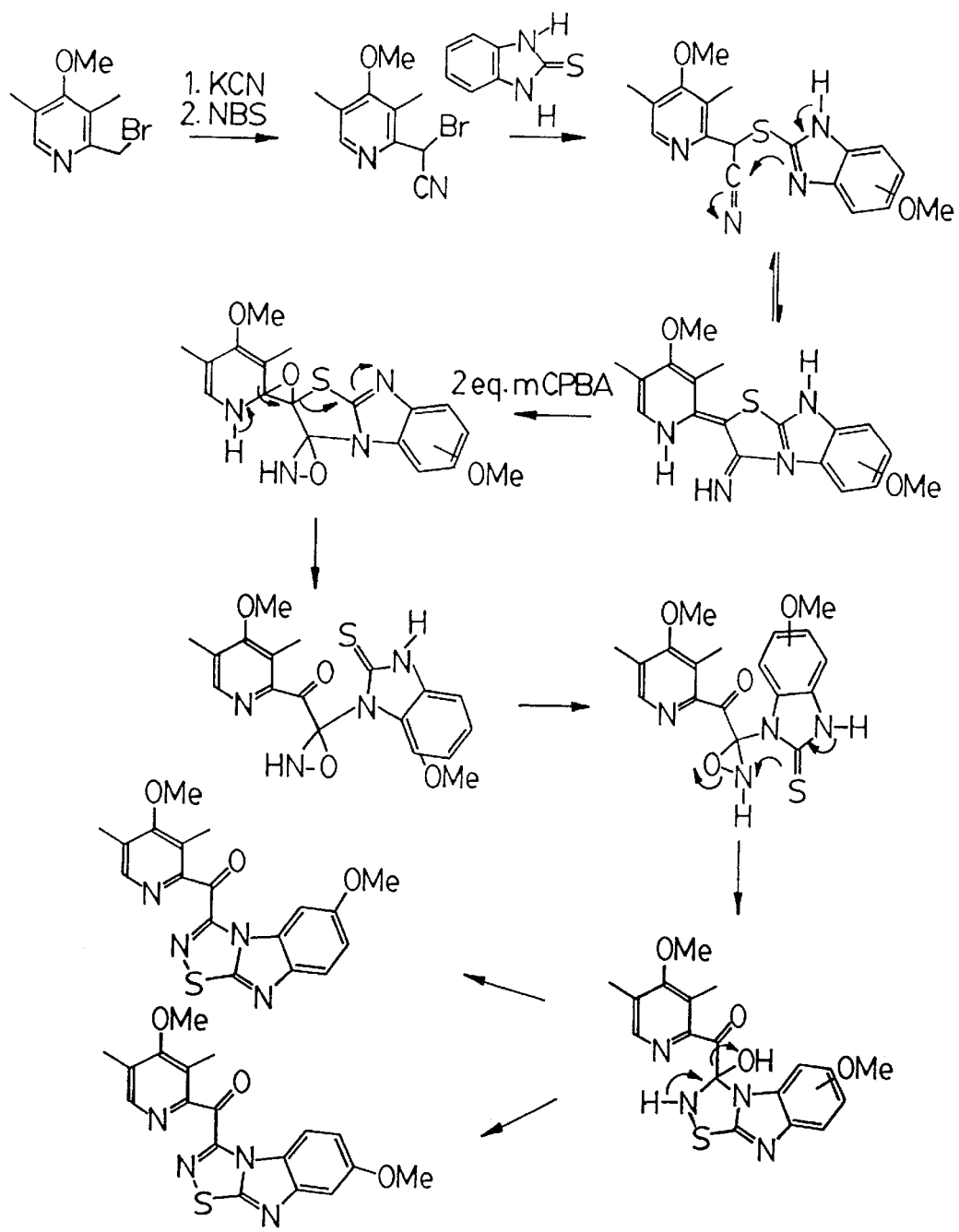
FIG. 2 is an illustration of a synthetic route for preparation of the most preferred compound for use in the process of the present invention.

The preferred compounds used in the pharmaceutical processes of the present invention, i.e. in inhibition of the proton pump enzyme by reaction of the mercaptan group thereof, show specificity for the mercaptan functional group as demonstrated by the fact that the imidazo[1,2-d]-thiadiazole nucleus of these compound show limited or no reactivity towards other nucleophiles present in vivo such as amines, hydroxide or iodide ions. In chemical model systems, the heterocyclic ring of 1,2,4-thiadiazolo[4,5-a] benzimidazole in particular is unreactive towards these nucleophiles.

Particularly preferred compounds of formulae I and II for use in processes according to the invention are those in which $R^5$ and $R^6$ are hydrogen, and Y is $R^7CO$ wherein $R^7$ is lower alkyl, aryl, hydrogen, or 2-pyridyl optionally substituted with 1 to 3 substituents selected from methyl and methoxy.

A particularly interesting, and preferred, group of compounds according to the present invention are those having amino acid or peptide residue side chains. These can be mono, di or tri-cyclic compounds according to the invention. The amino acid or peptide residue side chains can be attached to the bicyclic or tricyclic nucleus at the 3-position of the thiadiazole ring (group Y). In monocyclic compounds, such side chains can be attached at position 3 or position 5.

The use of amino acid or peptide residues as side chains in the monocyclic compounds used in the present invention, particularly when they are attached to the nucleus at position 5, allows selection of an appropriate such group having binding affinity for the enzyme which is to be inhibited by the compound. Furthermore, the binding affinity can be arranged, by appropriate choice of such a side group, so that the compound binds to the enzyme at a location on the proteinaceous chain of the enzyme adjacent to the thiol group of the enzyme which the compound is to attack. As described below and illustrated in FIG. 1 of the accompanying drawings, it is the —S—N═C— grouping of the compounds of the invention, activated by an appropriately chosen group Y, which is instrumental in attacking the thiol compound to form a disulfide. The presence of an appropriately chosen enzyme binding or recognition group as a side chain on the compound at a position remote from the —S—N═C— group allows the compound to seek out and bind to the selected enzyme, to enhance the chemical attack of the thiol group of the enzyme. Compounds of this nature, according to the invention, are accordingly highly selective in their attack upon a specific, chosen enzyme, and are much less reactive towards other thiols which they might encounter, due to the presence of the recognition side group.

A specific example of such a side group is the amino acid residue leucyl isoamylamide, of formula:

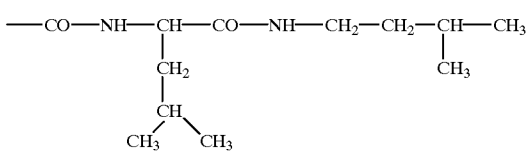

This group is the recognition sequence for cathepsin B and papain, at a location adjacent to the —SH group thereof. Accordingly, a compound such as 3-methoxy-5-amino-1,2,4-thiadiazole bearing this side group bound through its 5-amino group, is a good inhibitor of cathepsin L, cathepsin B and papain.

Peptido recognition sequences for cathepsin B and L may be defined as follows (shown attached to the 5-position of 1,2,4-thiadiazole of the present invention):

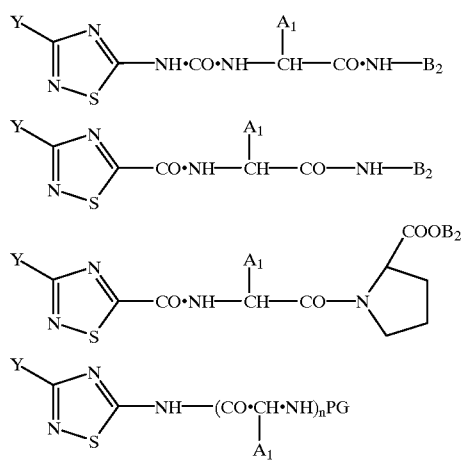

where Y is as previously defined;

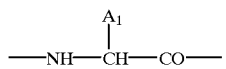

in each case representing an amino acid residue so that $A_1$ is any α-group from known amino acids, PG is an N-protective group selected from heterocyclylcarbonyl, benzoyl, carbobenzyloxy and tert. butoxy; $B_2$ is hydrogen, lower alkyl optionally substituted with amino, guanidino or N,N-di-(loweralkyl)quanidino; and n is 1 or 2.

The same groups can be utilized in bi- and tricyclic compounds according to the present invention. Preferred as group —NH—$CHA_1$—CO— is leucyl. Preferred as group $B_2$ is hydrogen, isoamyl or 4-quanidinobutyl. Preferred as group PG is carbobenzyloxy. Preferred as group (CO—$CHA_1$—NH)$_n$ is the dipeptide phenylalanyl-alanyl.

For inhibition of interleukin β-1 converting enzyme, the recognition side chain as compounds of the present invention is preferably a tripeptide, e.g. a side group of general formula:

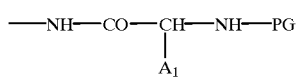

where —(CO—$CHA_1$—NH)— is -valinyl-alaninyl-aspartyl- and PG is carbobenzyloxy, preferably attached to a position remote from the —S—N=C— grouping, e.g. position 5 of a monocyclic thiadiazole of the invention.

Accordingly, additional specifically preferred compounds of formula III for the present invention include compounds in which T represents an amino acid or peptide residue, e.g. compounds of formula:

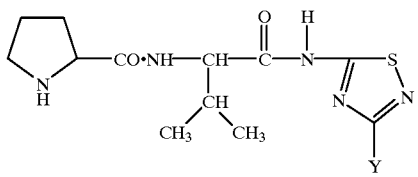

of formula:

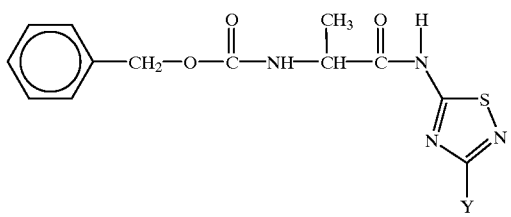

of formula:

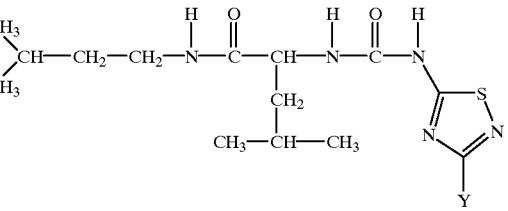

especially when Y=$OCH_3$ of formula:

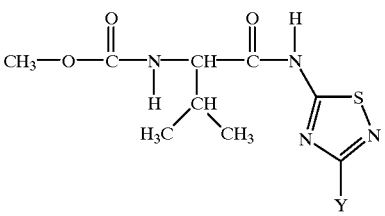

compounds in which W and T when taken together with the N atom to which they are bonded form an amino acid or peptide residue of formula AOR' or ANR'R", e.g. compounds of formula:

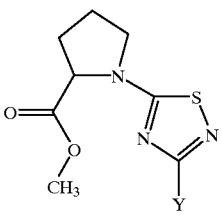

and of formula:

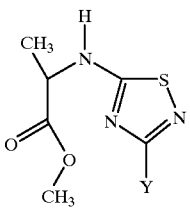

All compounds used in the process of the present invention are characterized by the 3-substituted 1,2,4-thiadiazole ring structure, unsubstituted at N-2 capable of chemical reaction with thiols to cleave the S—N bond at position 1,2. Provided that these characteristics are maintained, the range of groups and substituents at position 4 and 5 of the thiadiazole nucleus can be very broad, without seriously impacting upon this essential chemical reactivity of the compounds.

As used herein:

The term "lower", as applied for example to lower alkyl, means 1 to 8 carbon atoms.

The term "aryl", alone or in combination, means a phenyl or naphthyl radical which optionally carries one or more substituents selected from alkyl, alkoxy, halogen, hydroxy, amino and the like, such as phenyl, p-tolyl, 4-methoxyphenyl, 4-(tert-butoxy)phenyl, 4-fluorophenyl, 4-chlorophenyl, 4-hydroxyphenyl, 1-naphthyl, 2-naphthyl and the like.

The term "arylalkoxy carbonyl", alone or in combination, means a radical of the formula —C(O)—O— arylalkyl, in which the term "arylalkyl" has the significance given above. An example of an arylalkoxycarbonyl radical is benzyloxycarbonyl.

The term "arylalkyl", means an alkyl radical in which one hydrogen atom is replaced by an aryl radical, such as benzyl, phenylethyl and the like.

The term "cycloalkylcarbonyl" means an acyl group derived from a monocyclic or bridged cycloalkanecarboxylic acid such as cyclopropanecarbonyl, cyclohexanecarbonyl, adamantanecarbonyl, and the like, or from a benz-fused monocyclic cycloalkanecarboxylic acid which is optionally substituted by, for example, alkylamino, such as 1,2,3,4-tetrahydro-2-naphthoyl, 2-acetamido-1,2,3,4-tetrahydro-2-naphthoyl.

The term "arylalkanoyl" means an acyl radical derived from an aryl-substituted alkanecarboxylic acid such as phenylacetyl, 3-phenylpropionyl, hydrocinnamoyl, 4-phenylbutyryl, (2-naphthyl)acetyl, 4-chlorohydrocinnamoyl, 4-aminohydrocinnamoyl, 4-methoxyhydrocinnamoyl, and the like.

The term "aroyl" means an acyl radical derived from an aromatic carboxylic acid. Examples of such radicals include aromatic carboxylic acid, an optionally substituted benzoic or naphthoic acids such as benzoyl, 4-chloro-benzoyl, 4-carboxybenzoyl, 4-[(benzyloxy-carbonyl]benzoyl, 1-naphthoyl, 2-naphthoyl, 6-carboxy-2-naphthoyl, 6-[(benzyloxy)carbonyl]-2-naphthoyl, 3-benzyloxy-2-naphthoyl, 3-hydroxy-2-naphthoyl, 3-[(benzyloxy)formamido]-2-naphthoyl, and the like.

The term "heterocyclyl", as used herein except where noted, represents a stable 5- to 7-membered mono or bicyclic or stable 7- to 10-membered bicyclic heterocyclic ring which is either saturated or unsaturated, and which consists of carbon atoms, and from one to three heteroatoms selected from the group consisting of N, O, S, and wherein the nitrogen and sulfur heteroatoms may be optionally oxidized, and the nitrogen atom may optionally be quaternized, and including any bicyclic group in which any of the above defined heterocyclic rings is fused to a benzene ring. The heterocyclic ring may be attached at any heteroatom or carbon atom which results in the creation of a stable structure. Examples of such heterocyclic elements, commonly known as heterocyclyl include piperidinyl, piperazinyl, 2-oxopiperazinyl, 2-oxopiperazinyl, 2-oxopiperidinyl, 2-oxopyrrolidinyl, 2-oxoazepinyl, azepinyl, pyrrolyl, 4-piperidonyl, pyrrolidinyl, pyrazolyl, pyrazolidinyl, imidazolyl, imidazolinyl, imidazolidinyl, pyridyl, pyrazinyl, pyrimidinyl, pyridazinyl, oxazolidinyl, isoxazolyl, isoxazolidinyl, morpholinyl, thiazolyl, thiazolidinyl, isothiazolyl, quinuclidinyl, isothiazolidinyl, indolyl, quinolinyl, isoquinolinyl, benzimidazolyl, thiadiazolyl, benzopyranyl, benzothiazolyl, benzoxazolyl, furyl, tetrahydrofuryl, tetrahydropyranyl, thienyl, benzothienyl, tetrahydroquinolinyl (e.g. 1,2,3,4-tetrahydro-2-quinolinyl, etc.), 1,2,3,4-tetrahydroisoquinolinyl (e.g. 1,2,3,4-tetrahydro-1-oxo-isoquinolinyl etc.), quinoxalinyl, beta-carbolinyl, 2-benzofurancarbonyl, thiamorpholinyl, thiamorpholinyl sulfoxide, thiamorpholinyl sulfone, oxadiazolyl and the like. The heterocycle may be substituted on one or more carbon atoms or heteroatom which results in the creation of a stable structure. "Amino acid residues" means any of the naturally occurring alpha-, beta-, and gamma-amino carboxylic acids, including their D and L optical isomers and racemic mixtures thereof, and the N-lower alkyl- and N-phenyl lower alkyl-derivatives of these amino acids. The amino acid residue is bonded through a nitrogen of the amino acid. The naturally occurring amino acids which can be incorporated into the present invention include, but are not limited to, alanine, arginine, asparagine, aspartic acid, cysteine, cystine, glutamic acid, glutamine, glycine, histidine, isoleucine, leucine, lysine, methionine, ornithine, phenylalanine, proline, serine, threonine, thyroxine, tryptophan, tyrosine, valine, beta-alanine, and gamma-aminobutyric acid. Preferred amino acid residues include proline, leucine, phenylalanine, isoleucine, alanine, γ-amino butyric acid, valine, glycine, and phenylglycine.

All alpha-amino acids except glycine contain at least one asymmetric carbon atom. As a result, they are optically active, existing in either D or L form as a racemic mixture. Accordingly, some of the compounds of the present invention may be prepared in optically active form, or as racemic mixtures of the compounds claimed herein.

The term "A" wherein A is an amino acid or peptide of 2 to 3 amino acid residues refers to an amino acid or a peptide diradical starting with the HN— radical on the left hand side of A and terminated by the —C(O) radical on the right hand side. For example, the amino acid glycine is abbreviated HAOH wherein A is HN—$CH_2$—C(O).

The term "aryloxyalkanoyl" means an acyl radical of the formula aryl-O-alkanoyl.

The term "heterocyclyloxycarbonyl" means an acyl group derived from heterocyclyl-O—CO— wherein heterocyclyl is defined above.

The term "heterocyclylalkanoyl" means an acyl radical derived from a heterocyclyl-substituted alkane carboxylic acid wherein heterocyclyl has the same significance given above.

The term "heterocyclylalkoxycarbonyl" means an acyl radical derived from a heterocyclyl-substituted alkyl-O—COOH wherein heterocyclyl has the same significance given above.

The term "aminoalkanoyl" means an acyl radical derived from an amino-substituted alkanecarboxylic acid wherein the amino group can be a primary, secondary or tertiary amino group containing substituents selected from hydrogen, and alkyl, aryl, aralkyl, cycloalkyl, cycloalkylalkyl radicals and the like.

"Pharmaceutically acceptable, non-toxic salts" refers to pharmaceutically acceptable salts of the compounds of this invention which retain the biological activity of the parent compounds and are not biologically or otherwise undesirable (e.g. the salts are stable). Salts of the two types may be formed from the compounds of this invention: (1) salts of inorganic and organic bases from compounds Formula I which have a carboxylic acid functional group. (2) Acid addition salts may be formed at the amine functional group of many of the compounds of this invention.

Pharmaceutically acceptable salts derived from inorganic bases include sodium, potassium, lithium, ammonium, calcium, magnesium, ferrous, zinc, copper, manganous, aluminum, ferric, manganic salts and the like. Particularly preferred are the ammonium, potassium, sodium, calcium and magnesium salts. Pharmaceutically acceptable, non-toxic salts derived from organic bases include salts of primary, secondary and tertiary amines, substituted amines including naturally occurring substituted amines, cyclic amines and basic ion exchange resins. Such salts are exemplified by, for example, isopropopylamine, trimethylamine, diethylamine, triethylamine, tripropylamine, ethanolamine, 2-dimethylaminoethanol, tromethamine, dicyclohexamine, lysine, arginine, histidine, caffeine, procaine, hydrabramine, choline, betaine, ethylenediamine, glucosamine, metylglucamine, theobromine, purines, piperazine, piperidine, N-ethylpiperidine, polyamine resins and the like. Particularly preferred organic non-toxic bases are isopropylamine, diethylamine, ethanolamine, piperidine, tromethamine, dicyclohexylamine, choline and caffeine.

Pharmaceutically acceptable acid addition salts are formed with inorganic acids such as hydrochloric acid, hydrobromic acid, sulfuric acid, nitric acid, phosphoric acid and the like and organic acids such as acetic acid, propionic acid, glycolic acid, pyruvic acid, oxalic acid, malic acid, malonic acid, succinic acid, maleic acid, fumaric acid, tartaric acid, citric acid, benzoic acid, cinnamic acid, mandelic acid, methanesulfonic acid, ethanesulfonic acid, p-toluenesulfonic acid, salicylic acid and the like.

The term "animals" refers to humans as well as all other animal species, particularly mammals (e.g. dogs, cats, horses, cattle, pigs etc.), reptiles, fish, insects and helminths.

Some specific, most preferred compounds for use in processes according to the present invention are the following:

3-(1-oxoethyl)-1,2,4-thiadiazolo[4,5-a]benzimidazole, which has the following chemical formula:

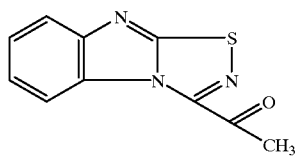

3-(oxophenylmethyl)-1,2,4-thiadiazolo[4,5-a] benzimidazole, which has the following chemical formula:

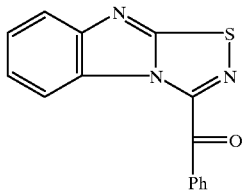

3-(2-pyridyl)-1,2,4-thiadiazolo[4,5-a]benzimidazole, which has the following chemical formula:

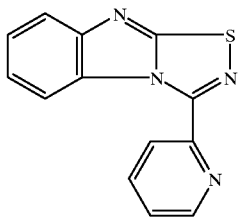

3-(4-methyl-1-piperazinyl)-1,2,4-thiadiazolo-[4,5-a] benzimidazole, which has the following chemical formula:

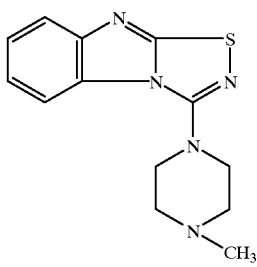

3-(4-morpholinyl)-1,2,4-thiadiazolo[4,5-a] benzimidazole, which has the following chemical formula:

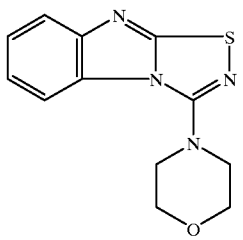

3-(1-pyrrolidinyl)-1,2,4-thiadiazolo [4,5-a] benzimidazole, which has the following chemical formula:

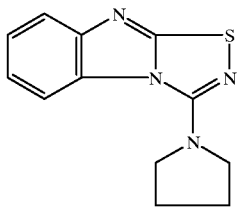

3-bromo-1,2,4-thiadiazolo[4,5-a]benzimidazole, which has the following chemical formula:

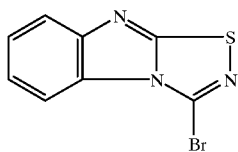

3-[(4-methoxy-3,5-dimethyl-2-pyridyl)oxomethyl]-1,2,4-thiadiazolo[4,5-a]benzimidazole, which has the following chemical formula:

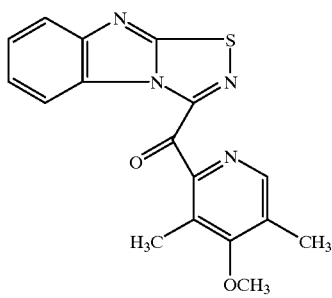

3-carboxy-1,2,4-thiadiazolo-[4,5-a]benzimidazole, which has the following chemical formula:

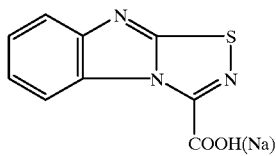

7-methoxy-3-[(4-methoxy-3,5-dimethyl-2-pyridyl)oxomethyl]-1,2,4-thiadiazolo[4,5-a]benzimidazole, which has the following chemical formula:

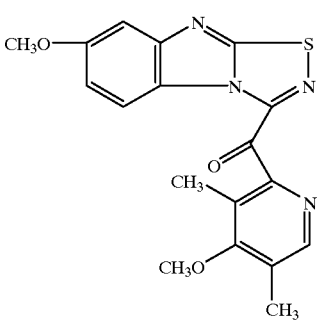

3-(4-methylphenylsulfonyl)-1,2,4-thiadiazolo [4,5-a] benzimidazole, which has the following chemical formula:

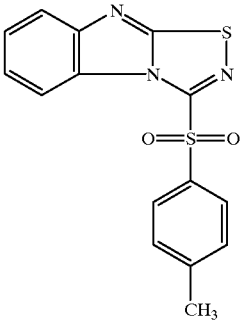

3-(1-oxoethyl)imidazo[1,2-d]-1,2,4-thiadiazole, which has the following chemical formula:

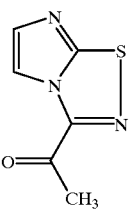

3-(oxophenylmethyl)imidazo[1,2-d]-1,2,4-thiadiazole, which has the following chemical formula:

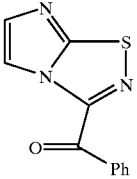

3-(4-acetyl-i-piperazinyl)-1,2,4-thiadiazolo[4,5-a]benzimidazole, which has the following chemical formula:

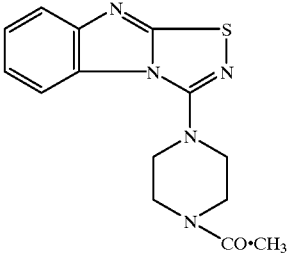

3-[4-(3-amino-2-pyridyl)piperazinyl]-1,2,4-thiadiazolo[4,5-a]benzimidazole, which has the following chemical formula:

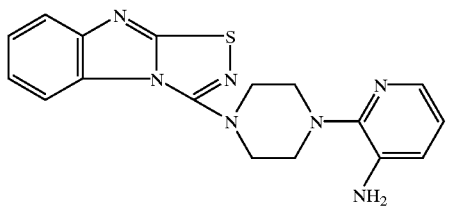

3-[4-(2-pyridyl)piperazinyl]1,2,4-thiadiazolo-[4,5-a]benzimidazole, which has the following chemical formula:

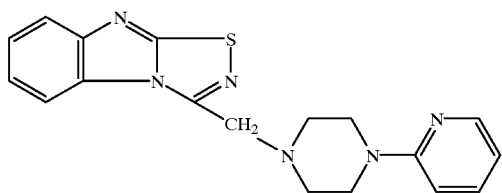

3-[4-(3-amino-2-pyridyl)piperazinyl-methyl]-1,2,4-thiadiazolo-[4,5-a]benzimidazole, which has the following chemical formula:

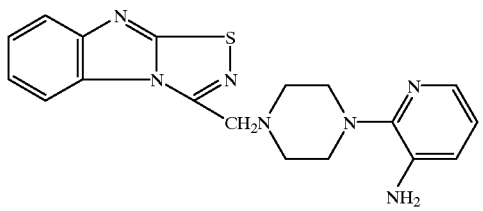

3-[4-(2-pyridyl)piperazinyl-methyl]-1,2,4-thiadiazolo-[4,5-a]benzimidazole, which has the following chemical formula:

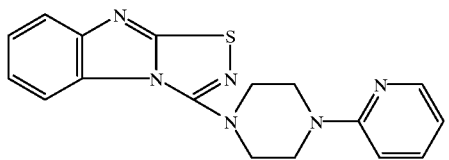

3-{[4-(1-(4-chlorophenyl)-1-phenylmethyl)piperazinyl]methyl}-1,2,4-thiadiazolo[4,5-a]benzimidazole, which has the following chemical formula:

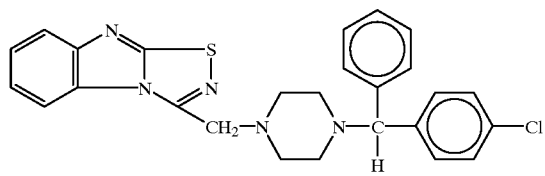

(3-Methoxy-1,2,4-thiadiazol-5-yl)carbamoyl-L-leucyl isoamylamide, which has the following chemical formula:

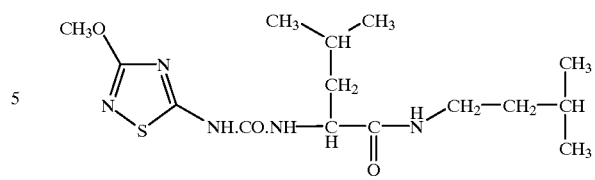

and N-(3-methoxy-1,2,4-thiadiazol-5-yl)-carbobenzyloxy-L-phenylalanyl-L-alaninamide, which has the following chemical formula:

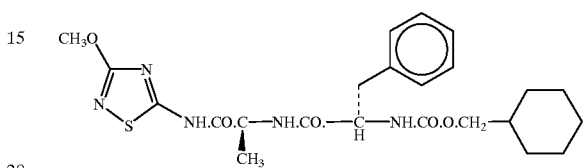

The present invention provides synthetic methods for preparing compounds useful in the invention. Some of these methods involve conversion of one compound into another, different such compound. The choice of method depends largely upon the desired Y group, i.e. the substituent on the 3-position in the final compound.

In a first process, applicable to bi- or tricyclic compounds, the corresponding 3-oxo compound of formula V (below), carrying a lower alkyl or lower arylalkyl substituent at position 2 is reacted with YCN in an inert solvent. This method is appropriate for compounds in which Y is lower alkyl, aryl, arylalkyl, cycloalkyl, 1-haloalkyl, 1,1-dihaloalkyl, heterocyclyl, lower alkyl sulfonyl or aryl sulfonyl. The reaction can be represented as follows:

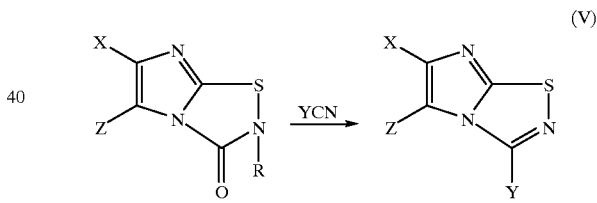

(V)

The appropriate nitrile compounds YCN wherein Y is lower alkyl, aryl, arylalkyl, cycloalkyl, 1-haloalkyl, 1,1-dihaloalkyl, lower alkylsulfonyl, arylsulfonyl or heterocyclyl are for the most part commercially available e.g. from Aldrich Chemical Co. Alternatively, they can be prepared by methods known in the Art (see for example Chapter 17 in Organic Functional Group Preparations, Vol. I by Sandler and Karo, Academic Press, 1983). Acetonitrile, benzonitrile, 2-cyanopyridine, cyclo-pentylcyanide, dibromoacetonitrile, 6-cyanopurine and p-toluenesulfonyl cyanide are some typical examples. The reaction normally takes place at elevated temperature between 70 to 140° C. in an inert solvent such as toluene, dimethylformamide for a period of 6 to 24 hours, preferably 16 hours. In some cases, YCN is used as the solvent. The product is isolated by conventional means.

Compounds of formulae II and III, i.e. bicyclic and tricyclic compounds, in which Y is amino, lower alkylamino, lower dialkylamino, thioalkyl can also be prepared by using compounds of formula YCN wherein Y is amino, lower alkylamino, lower dialkylamino or lower thioalkyl. Examples of YCN is this category are cyanamide, 1-piperidinecarbo-nitrile, methyl thiocyanate which are commercially available. Compounds YCN can also be synthesized from cyanogen bromide according to literature procedures (see p.174, Fieser and Fieser, Reagents in Organic Synthesis, John Wiley and Sons, 1967).

2-Alkyl-1,2,4-thiadiazolo[4,5-a]benzimidazole-3(2H)-ones of formula V are prepared from alkyl isocyanate and 2-mercaptobenzimidazole according to the procedure of Martin et al., Tetrahedron, 1983, 39, 2311. 2-Alkylimidazo[1,2-d]-1,2,4-thiadiazole-3(2H)-ones of formula V are prepared from alkyl isocyanate and 2-mercaptoimidazole according to the procedure of Tittlebach et al., J. Prakt Chem. 1988, 330, 338–348. The 2-mercaptobenzimidazoles are either commercially available, or can be prepared by methods well known in the art or readily available in the literature. Commercially available 2-mercaptobenzimidazoles includes 5-methyl-2-mercaptobenzimidazole, 5-methoxy-2-mercaptobenzimidazole, 5-chloro-2-mercaptobenzimidazole. Suitable 2-mercaptobenzimidazole which are not commercially available can be prepared by known methods. Preparative method include those of Billeter et al., Ber., 1887, 20, 231, Org. Synth., Coll. Vol. 4, 569, Futaki et al., J. Pharm. Soc. Jpn., 1954, 74, 1365, Bucknall et al., Nature, 1967, 213, 1099.

In a second, similar process, applicable for the preparation of bicyclic and tricyclic compounds in which group Y in the final compound is $R^7$—C=O and $R^7$ is lower alkyl, aryl, lower arylalkyl, lower cycloalkyl, lower alkoxy, amino, lower alkylamino, lower dialkylamino, heterocyclyl, the heterocyclic ring being attached at any heteroatom or carbon atom which results in the creation of a stable structure, NR'R", ANR'R", AOR' wherein A is an amino acid residue or a peptide of 2 to 3 amino acid residues and R', R" have the same definition as above, a compound of general formula:

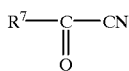

is reacted with the corresponding 3-oxo compound carrying a lower alkyl or lower arylalkyl substituent at position 2, i.e. a compound of formula V used in the first process above, thus:

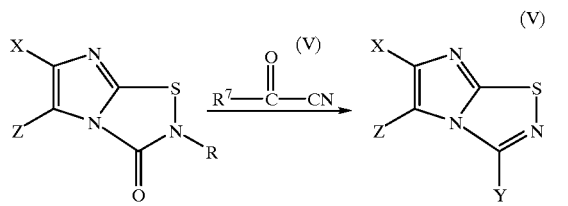

The reaction may be carried out in an inert solvent such as dichloromethane, tetrahydrofuran or dimethylformamide. The reaction takes place at room temperature over a period of 3 to 48 hours, usually about 6 hours. The resulting solid is then isolated by conventional means.

Most cyanoketones, cyanoester derivatives of formula VI are commercially available. The cyanoketone derivatives used in this invention are either commercially available or can be prepared by methods known in the art. The commercially available cyanoketones include, benzoyl cyanide, acetyl cyanide, methoxycarbonyl cyanide. A list of commercially available cyanide derivatives is available (Chem Sources, U.S.A., 24th Ed., 1983, Directories Publishing Company Inc., Ormont Beach, Fla.). Appropriate cyanoketones, cyanoesters which are not commercially available can be readily prepared by methods known in the art such as the ones described in Mathieu et al., Formation of C—C Bonds, Vol I, p. 456–457, George Thieme Verlag, 1973, Stuttgart. Other suitable methods include those of Koenig et al., Tet. Lett., 1974, 2275 and Ando et al., Synthesis, 1983, 637. These methods include reacting an acid chloride with cuprous cyanide or potassium cyanide.

Alternatively, compounds of formula I in which Y is $R^7$—C=O wherein $R^7$ has the same definition as above can be prepared by the hydrolysis of compounds of formula I wherein Y is $R^7$—C(Hal)$_2$ and wherein Hal is a halogen. Such an hydrolysis can be carried out in a strongly acidic media or in aqueous silver nitrate, and can be represented thus:

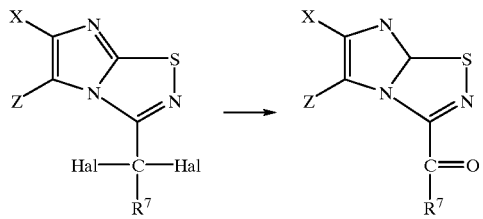

A third process for making the imidazole and benzimidazole products with Y-groups as in the second process described above, involves, as a final step, reacting a 2-thioether diazole compound of formula VII with m-chloroperbenzoic acid (MCPBA) in an inert solvent, to effect cyclization to form the 1,2,4-thiadiazole ring, and can be represented as follows:

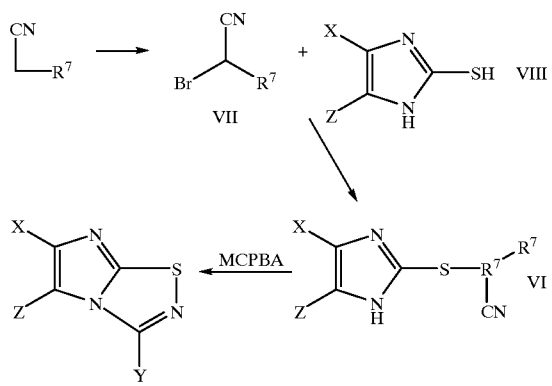

A bromoheterocyclylacetonitrile derivative (IV) can be reacted with 2-mercaptobenzimidazole (VIII) in base to give a compound of formula VI. Examples of those bases are sodium hydroxide or potassium hydroxide. The reaction takes place in a mixture of water and alcohol at room temperature for about 1 to 16 hours, preferably 8 hours, the product compound VII is isolated by conventional means.

Compound VI reacts with m-chloroperbenzoic acid, in an inert solvent such as dichloromethane, or 1,2-dichloroethane to give the compound of formula I where Y is $R^7$—C=O. The reaction takes place at room temperature for about 3 to 8 hours, preferably 3 hours. The product is isolated by conventional means.

The bromoheterocyclylacetonitrile (VII) derivative is in turn prepared by reacting a compound of formula X with N-bromosuccinimide in an inert solvent such as carbon tetrachloride.

A fourth process uses a compound of formula I in which Y is $R^7$—C=O (formula IA) as the starting material, and derivatizes it to a compound of formula I in which Y is —CHOH—$R^7$ (formula IB) or —C=NOH—$R^7$ (formula IC), or —COOH (formula ID), thus:

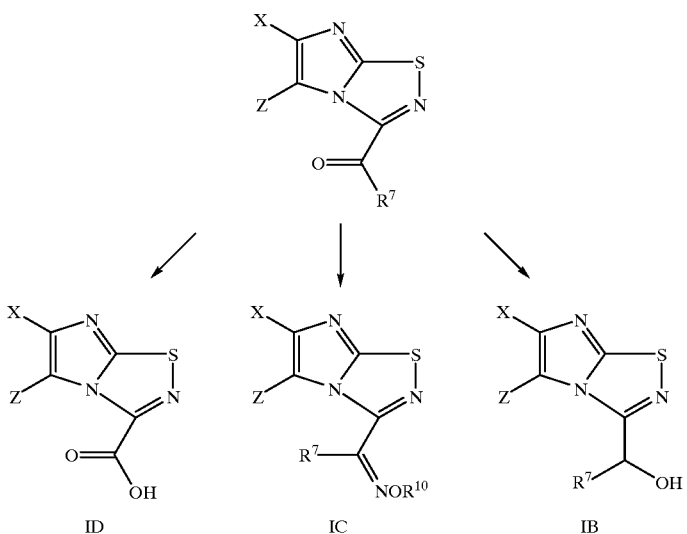

Compounds of formula IB can be prepared by the reduction of the corresponding compounds of formula IA wherein Y is $R^7$—C=O with sodium borohydride, or sodium cyanoborohydride in alcohol. Compound of formula IB is isolated by conventional means.

Compounds of formula IC can be prepared by reacting compound of formula I wherein Y is $R^7$—C=O with hydroxylamine derivatives. Examples of hydroxylamines are hydroxylamine, methoxylamine, ethoxylamine, benzyloxylamine. The conversion of a ketone to an oxime is well-documented in the art (see, for example, Sandler and Karo, Organic Functional Group Preparations, 1989, Vol. III, Chapter II).

Compounds of formula ID in which $R^7$ is hydroxy can be prepared by the base hydrolysis of the compounds of formula I wherein Y is $R^7$—C=O and $R^7$ is lower alkoxy. The reaction is carried out in 1M sodium hydroxide at room temperature in a mixture of water and an organic solvent such as methanol, ethanol, 1,4-dioxane or acetonitrile. The product is isolated by conventional means after neutralization of the base with diluted acid.

A fifth process, applicable to the preparation of compounds of formula I according to the invention in which Y represents halogen, uses the same starting compound of formula V as used in the first and second process, and reacts it with cyanogen halide, thus:

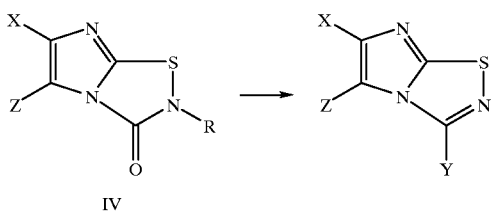

The reaction takes place in an inert solvent. The compound is isolated by conventional means.

A sixth process uses as starting materials the compounds of formula I where Y represents halogen, e.g. compounds prepared according to the fifth process above, and reacts them with a primary or secondary amine, or alcohol, to give a compound of formula I wherein Y is NR'R", AOR', ANR'R", OR'. R', R" have the same definition as above. This process proceeds best when Y in the starting material is bromine. It can be represented thus:

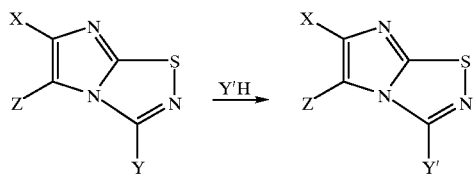

Nucleophiles such as lower alkoxides, aryloxides, lower arylalkoxides, lower cycloalkoxides, ammonia, lower alkylamines, lower dialkylamines, heterocyclic amines, HNR'R", HANR'R", HAOR', wherein A is an amino acid residue or a peptide of 2 to 3 amino acid residues, react with compounds of formula I wherein Y=bromide in an inert solvent to give compounds of formula I wherein Y is lower alkoxy, aryloxy, lower arylalkoxy, lower cycloalkoxy, amino, lower alkylamino, lower dialkylamino, NR'R", ANR'R", AOR', wherein A is an amino acid residue or a peptide of 2 to 3 amino acid residues.

A seventh process uses as starting materials compounds of formula I according to the invention in which Y represents COOH (preparable by the fourth process above), and reacts them with an amine to give a compound of formula I wherein Y is CO—$R^7$, wherein $R^7$ is NR'R", AOR', ANR'R", thus:

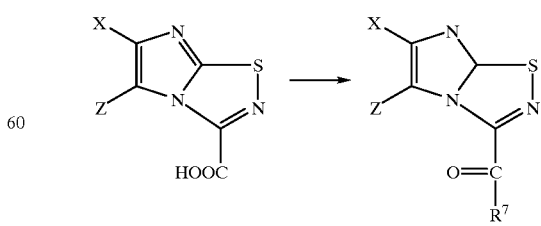

In this way, compounds of formula I in which Y is $R^7$—C=O and $R^7$ is NR'R", AOR', ANR'R" can be prepared by reacting the carboxylic acid compound of formula I wherein Y is COOH with an amino acid amide HANR'R", or amines HNR'R", or amino acid ester HAOR', in the presence of a dehydrating agent such as 1-(3-dimethylaminopropyl)-3-ethylcarbodiimide (EDCI) and hydroxybenzotriazole in an inert solvent such as tetrahydrofuran, dimethylformamide or dichloromethane.

An eighth process applicable for the preparation of compounds in which Y represents lower alkylsulfonyl, arylsulfonyl, heterocyclylsulfonyl, lower aryl alkylsulfonyl, lower alkylsulfinyl, arylsulfinyl, heterocyclylsulfinyl or lower arylalkylsulfinyl comprises reaction of the corresponding thioether compound with the predetermined stoichiometric amount of an oxidizing agent, thus:

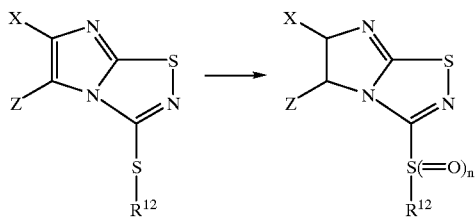

where n=1 or 2. A preferred oxidizing agent for use in this process is meta-chloroperbenzoic acid mCPBA, but there are many other, suitable such oxidizing agents.

One of the preferred processes according to the invention is the inhibition of enzymes, in vitro or in vivo, and specifically the inhibition of the proton pump enzyme $H^+/K^+$-ATPase, so as to treat gastric ulcers in humans. A major development in the treatment of peptic ulcers has been realized with the introduction of $H^+/K^+$-ATPase inhibitors. The enzyme $H^+/K^+$-ATPase, which is also known as the proton pump, is located in the membrane of gastric parietal cells and is responsible for the transport of protons from blood to lumen, decreasing the pH of stomach contents which leads to aggravation of peptic ulcers. The effectiveness of the process of the present invention in trapping this enzyme, and hence providing a means of treating peptic ulcers, is demonstrated in the specific examples below. The processes of the present invention are however applicable to a wide variety of other thiol trapping chemical systems, both biochemical (enzymatic) and industrial, as set out below in connection with their reactivity towards phenethylmercaptan.

Since the thiadiazole compounds trap thiol containing compounds by the formation of a S—S bond, they can be cysteine SH modifiers. Thus the thiol trapping agents can be used as affinity labels in the chemical modification of cysteine residues on an enzyme. Because these compounds can function as affinity labels to enzymes containing cysteine residues, they are useful inhibitors of many physiologic enzymes such as Cathepsin B, Papain, Interleukin β-1 Converting Enzyme, and protein disulfide isomerase (HIV), as well as $H^+/K^+$-ATPase. Because enzyme pathways are implicated in a variety of physiological conditions and disease states, the compounds of this invention have many potential therapeutic utilities.

Alternatively, thiol trapping agents can react with cysteine residue on enzymes and proteins, and thereby alter the biochemical properties of the enzyme. Thiol trapping agents can be useful stabilizers and enhancers of cysteine residue containing enzymes. Example of some of these therapeutic important enzymes are PC1 convertase, furin (see O'Rabilly S. et al., New England Journal of Medicine, 1995, 23, 1386–1390). PC1 is the convertase responsible for the processing of proglucagon into the peptide GLP-1. Regulators of GLP-1 may be useful therapeutic agents for the treatment of diabetes and obesity. Compounds of this invention are thiol trapping a gents and can be used as stabilizers and enhancers of cysteine containing enzymes.

The reactivity of the compounds in the process of the invention can be illustrated by means of their reaction with phenethyl mercaptan. This is generally illustrated in FIG. 1 of the accompanying drawings, with R of the thiol reagent representing a phenethyl group. In addition, based on prior art (Im et al., J. Biol. Chem., 1985, 260, 4591; Sturm et al., J. Org. Chem., 1987, 52, 4573; Lorentzon et al., Biochim., Biophys. Acta, 1985, 817, 25), phenethylmercaptan is useful as a model for the $H^+/K^+$-ATPase to examine the reactivity of compounds towards thiol group(s) of the enzyme. It was found that compounds of formula I react with phenethyl mercaptan ($RSH=PhCH_2CH_2SH$, FIG. 1) in an inert solvent to give the compound of formula XI. The compound of formula XI reacts with an additional mole of phenethyl mercaptan to produce a compound of formula XII which decomposes to give compounds of formula XIII and XIV.

A minimum of two moles of phenethyl mercaptan for 1 mole of substrate is required to effect the ring opening of 1,2,4-thiadiazolo[4,5-a]benzimidazoles to give the compound of formula XII. In general, the ring opening reaction is slow with two moles of phenethyl mercaptan. The reaction rate increases rapidly when a large excess of phenethyl mercaptan (for example, 25 fold) is used. It was found that compounds used in the present invention react rapidly with phenethyl mercaptan according to the process set out in FIG. 1. The disulfide could not be isolated since it was found to react rapidly with a second mercaptan to give the disulfide of phenethyl mercaptan and the illustrated intermediate. This degradation of the trapped thiol intermediate to form the disulfide has also been observed in the chemical model for the $H^+/K^+$-ATPase (Lindberg et al., J. Med. Chem., 1986, 29, 1329). It is noteworthy that in the real enzyme, the second step involving attack of another thiol group would not happen because of steric factors prohibiting the approach of two enzymes or would lead to formation of a disulfide bond in the event that another proximal thiol group is present. In both cases, this would lead to inhibition of the enzyme.

According to the present invention, it has been found that compound such as 3-methoxy-5-amino-1,2,4-thiadiazoles reacted with benzyl mercaptan in an organic solvent such as methanol to give 3-thiocarbamoyl methoxyisourea:

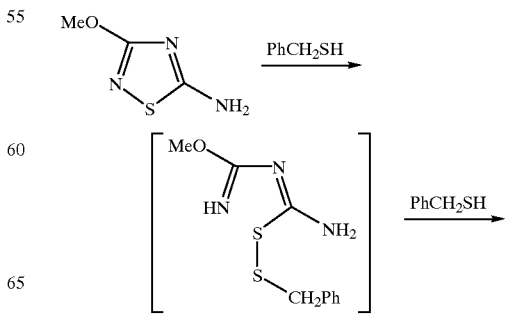

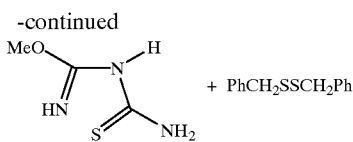

Other 1,2,4-thiadiazoles such as 3-methyl-5-dibenzylamino-1,2,4-thiadiazole, 3-methyl-5-benzylamino-1,2,4-thiadiazole and 3,5-di(3-pyridyl)-1,2,4-thiadiazole do not react with benzyl mercaptan under similar conditions. The chemical reactivity of monocyclic 1,2,4-thiadiazole as thiol trapping agent depends on the substituent at the 3 and 5 position of the ring system.

1,2,4-thiadiazolo[4,5-a]benzimidazole derivatives undergo similar reaction with mercaptans

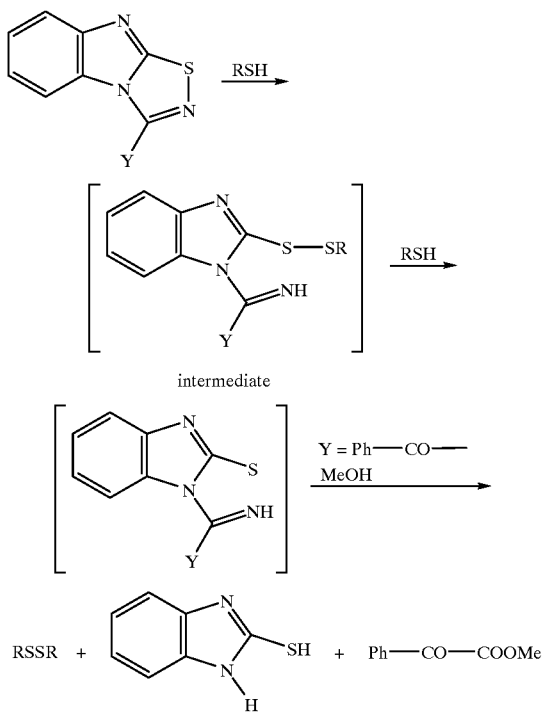

When RSH is thiolphenol, the resulting Ph—S—S—Ph dimer can be isolated. This reaction is also general for a variety of 1,2,4-bicyclic and tricyclic 1,2,4-thiadiazoles with different substituent at the 3 position of the heterocycle.

The preferred compounds used in the processes of this invention are heterocycles with molecular weight less than 440. The spectrum of log P of these molecules, i.e. the partition coefficient between octanol and water, varies from 0.5 to 4.0 which covers the lipophilicity range of most known drugs. These are important factors in the development of therapeutic agents, and reflect that individual analogs may have potential application as therapeutic agents in diseases wherein the inhibition of thiol containing enzymes is a potential solution to treatment of the disease.

The specificity of the compounds used in processes of the present invention for the mercaptan functional group is shown by the fact that these compounds show limited or no reactivity towards other nucleophiles present in vivo such as amines, hydroxide or iodide ions. In chemical model systems, the heterocyclic ring of 1,2,4-thiadiazolo[4,5-a] benzimidazole is unreactive towards these nucleophiles.

One specific, preferred compound for use in processes according to the present invention is 7-methoxy-3-[(4-methoxy-3,5-dimethyl-2-pyridyl)oxomethyl]-1,2,4-thiadiazolo[4,5-a]benzimidazole. This molecule carries an electron-withdrawing group at the 3-position of the heterocyclic ring. It has limited solubility in water. The structure of this compound was proved by X-ray crystallography. $^1$H and $^{13}$C NMR, IR, mass spectrometry and elemental analysis provided additional evidence for the chemical identity of this compound. Further specific details of its preparation, characterization and properties are given in the specific examples below. The compound is active in the suppression of gastric acid secretion in animal model.

For the treatment of peptic ulcers, the compounds may be used in the process of the invention by administration orally, topically, or parenterally in dosage unit formulations containing conventional non-toxic pharmaceutically acceptable carriers, adjuvants and vehicles. The term parenteral as used herein includes subcutaneous injection or infusion techniques. In addition to the treatment of warm-blooded animals such as mice, rats, horses, cattle, sheep, dogs, cats, etc., the compounds of the invention are effective in the treatment of humans.

For compositions, conventional non-toxic solid carriers include, for example, pharmaceutical grades of mannitol, lactose, starch, magnesium stearate, sodium saccharin, talcum, cellulose, glucose, sucrose, magnesium carbonate, and the like may be used. The active compound as defined above may be formulated as liquid pharmaceutically administrable compositions can, for example, be prepared by dissolving, dispersing, etc. an active compound as defined above and optional pharmaceutically adjuvants in a carrier, such as, for example, water, saline, aqueous dextrose, glycerol, ethanol, and the like, to thereby form a solution or suspension. If desired, the pharmaceutical composition to be administered may also contain a minor amount of non-toxic auxiliary substances such as wetting or emulsifying agents and the like, for example, sodium acetate, sorbitan monolaurate, triethanolamine sodium acetate, triethanolamine oleate, etc. Actual methods of preparing such dosage forms are known, or will be apparent to those skilled in this art: for example, see Remington's Pharmaceutical Sciences, Mack Publishing Company, Easton, Pa., 15th Edition, 1975. The composition of formulation to be administered will, in any event, contain a quantity of the active compound(s) in an amount effective to alleviate the symptoms of the subject being treated.

The pharmaceutical compositions containing the active ingredient may be in a form suitable for oral use, for example, as tablets, troches, lozenges, aqueous or oily suspensions, dispersible powders or granules, emulsions, hard and soft capsules, or syrups or elixirs. Compositions intended for oral use may be prepared according to any method known to the art for the manufacture of pharmaceutical compositions and such compositions contain one or more agents from the group consisting of sweetening agents, flavouring agents, colouring agents and preserving agents in order to provide pharmaceutically elegant and palatable preparations. Tablets contain the active ingredient in admixture with the non-toxic pharmaceutically acceptable excipients which are suitable for the manufacture of tablets. The excipients may be for example, inert diluents, such as calcium phosphate or sodium phosphate; granulating and disintegrating agents, for example, corn starch, or alginic acid; binding agents, for example starch, gelatin or acacia, and lubricating agents, for example magnesium stearate, stearic acid or talc. The tablets may be coated by known techniques to delay the disintegration and absorption in the gastrointestinal tract and thereby provide a sustained action over a long period. For monostearate or glyceryl distearate may be employed.

Formulations for oral use may also be presented as hard gelatin capsules wherein the active ingredients are mixed with an inert solid diluent, for example, calcium phosphate or kaolin, or as soft gelatin capsules wherein the active ingredient is mixed with water or an oil medium, for example peanut oil, liquid paraffin, or olive oil.

Aqueous suspensions contain the active materials in admixture with the excipient suitable for the manufacture of aqueous suspensions. Such excipients are suspending agents, for example sodium carboxymethylcellulose, methylcellulose, hydroxypropylmethylcellulose, sodium alginate, polyvinylpyrrolidone, gum and gum acacia; dispersing or wetting agents may be a naturally-occurring phosphate, for example lecithin, or condensation products of an alkene oxide with fatty acids, for example polyoxyethylene stearate, or condensation products of ethylene oxide with long chain aliphatic alcohols, for example heptadecathyl-eneoxycetanol, or condensation products of ethylene oxide with partial esters derived from fatty acids and hexitol anhydrides, for example polyethylene sorbitan monooleate. The aqueous suspensions may also contain one or more preservatives, for example ethyl, or n-propyl, p-hydroxybenzoate, one or more colouring agents, such as sucrose or saccharin.

Oily suspensions may be formulated by suspending the active ingredient in a vegetable oil, for example arachis oil, olive oil, sesame oil or coconut oil, or in a mineral oil such as liquid paraffin. The oily suspensions may contain a thickening agent, for example beeswax, hard paraffin or cetyl alcohol. Sweetening agents such as those set forth above, and flavouring agents may be added to provide a palatable oral preparation. These compositions may be preserved by the addition of an anti-oxidant such as ascorbic acid.

Dispersible powders and granules suitable for preparation of an aqueous suspension by the addition of water provide the active ingredient in admixture with the dispersing or wetting agent, suspending agent and one or more preservatives. Suitable dispersing or wetting agents and suspending agents are exemplified by those already mentioned above. Additional recipients, for example sweetening, flavouring and colouring agents, may also be present.

The pharmaceutical composition of the invention may also be in the form of oil-in-water emulsions. The oily phase may be a vegetable oil, for example olive oil or arachis oil, or a mineral oil, for example liquid paraffin or mixtures of these. Suitable emulsifying agents may be naturally-occurring phosphates, esters derived from fatty acids and hexitol anhydrides, for example sorbitan monooleate, and condensation products of the said partial esters with ethylene oxide, for example polyoxyethylene sorbitan monooleate. The emulsion may also contain sweetening and flavouring agents.

Syrups and elixirs may be formulated with sweetening agents, for example glycerol, propylene glycol, sorbitol or sucrose. Such formulations may also contain a demulcent, a preservative and flavouring and colouring agents. The pharmaceutical compositions may be formulated according to the known art using those suitable dispersing or wetting agents and suspending agents which have been mentioned above. The sterile injectable preparation may also be a sterile injectable solution or suspension in a non-toxic parenterally-acceptable diluent or solvent, for example as a solution in 1,3-butane diol. Among the acceptable vehicles and solvents that may be employed are water, Ringer's solutions and isotonic sodium chloride solution. In addition, fixed oils are conventionally employed as a solvent or suspending medium. For this purpose any bland fixed oil may be employed including synthetic mono- or diglycerides. In addition, fatty acids such as oleic acid find use in the preparation or injectables.

Parenteral administration is generally characterized by injection, either subcutaneously, intramuscularly or intravenously. Injectables can be prepared in conventional forms, either as liquid solutions or suspension in liquid prior to injection, or as emulsions. Suitable excipients are for example, water, saline, dextrose, glycerol, ethanol or the like. In addition, if desired, the pharmaceutical compositions to be administered may also contain minor amounts of non-toxic auxiliary substance such as wetting or emulsifying agents, pH buffering agents and the like, such as for example, sodium acetate, sorbitan monolaurate, triethanolamine oleate, etc.

The amount of active ingredient that may be combined with the carrier materials to produce a single dosage form will vary depending upon the host treated and the particular mode of administration of humans may contain from 0.5 mg to 5 gm of active agent compounded with an appropriate and convent amount of carrier material which may vary from about 5 to about 95% of the total composition. Dosage unit forms will generally contain between from about 1 mg to about 500 mg of an active ingredient.

It will be understood, however, that the specific dose level for any particular patient will depend upon a variety of factors including the activity of the specific compound employed, the age, body weight, general health, sex, diet, time of administration, drug combination and the severity of the particular disease undergoing therapy.

The invention is further described and illustrated in the following specific examples.

SPECIFIC DESCRIPTION OF THE MOST PREFERRED EMBODIMENTS

EXAMPLE 1

Preparation of Bromo(2-pyridyl)acetonitrile

To a solution of (2-pyridyl)acetonitrile (12.0 g, 0.10 mole) in 150 ml of carbon tetrachloride, was added 18.1 g of N-bromosuccinimide (0.10 mole) at room temperature. The mixture was refluxed for 1.5 h. The resulting precipitate was removed by filtration and the solvent was removed under reduced pressure to give the crude product, which was recrystallized from hexane to yield 18.6 g (94%) of the title compound as red crystals:

mp 62–64° C.; $^1$H NMR (DMSO-$d_6$)δ 8.67 (d, 1H), 7.97 (t, 1H), 7.70 (d, 1H), 7.51 (td, 1H) 5.60(ρ, 1H) ppm; IR (KBr)ν 3064, 2972, 1712, 1587, 1470, 1439, 1051, 993 cm$^{-1}$; MS m/z 196, 198 (M$^+$), 117 (M$^+$–Br); HRMS calcd for $C_7H_5BrN_2$ 195.9630, found 195.9645.

Proceeding in a similar manner, the following compound was made:

bromo(4-methoxy-3,5-dimethyl-2-pyridyl)acetonitrile:

mp 56–57° C.; $^1$H NMR (CDCl$_3$)δ 8.31 (s, 1H), 5.67 (s, 1H) 3.81 (s, 3H), 2.37 (s, 3H), 2.30 (s, 3H) ppm; $^{13}$C NMR (CDCl$_3$)δ 164.84, 150.19, 149.56, 128.28, 125.59, 115.49, 60.135, 27.99, 13.51, 11.05 ppm; IR (KBr)ν 3415, 2988, 2210, 1568, 1472, 1255, 997, 791 cm$^{-1}$; MS m/z 255, 257 (MH$^+$) 175 (M$^+$–Br)

EXAMPLE 2

Synthesis of [(2-benzimidazolyl)thio](2-pyridyl) acetonitrile

A mixture of 2-mercaptobenzimidazole (0.30 g, 3.0 mmole), bromo(2-pyridyl)acetonitrile (0.59 g, 3.0 mmole) and potassium carbonate (0.37 g 3.0 mmole) in 50 ml of dry N,N-dimethylformamide was heated at 60° C. for 6 h. The solvent was evaporated. The residue was dissolved in ethyl acetate, washed with water and then saturated sodium chloride solution. The organic layer was dried over magnesium sulfate and evaporated to give a solid. The crude product was further purified by column chromatography on silica gel (100% ethyl acetate) to give 66 mg (10%) of the title compound as a solid; mp 166–167° C.; $^1$H NMR (DMSO-$d_6$)δ 9.3 (m, 1H), 8.65 (m, 2H), 8.32 (m, 1H), 7.78 (br s, 4H), 4.81 (br s, 2H) ppm; IR ν 2206, 1512, 1465, 1432, 1357, 1179, 740 cm$^{-1}$.

In a similar manner, by replacing 2-mercaptobenzimidazole with 2-mercaptoimidazole, the following compound was made:

[(2-imidazolyl)thio](2-pyridyl)acetonitrile:

mp 203–204° C. (dec); $^1$H NMR (CDCl$_3$)δ 8.51 (d, 1H), 7.65 (t, 1H), 7.36 (d, 2H), 7.12 (d, 1H), 7.03 (dd, 1H), 6.33 (br s, 2H) ppm, $^{13}$C NMR (CDCl$_3$)δ 154.08, 148.23, 145.76, 136.84, 134.95, 134.43, 119.15, 118.40, 109.32, 96.15 ppm; IR (KBr)ν 3344, 3225, 2202, 1643, 1493, 1485, 1427 cm$^{-1}$

EXAMPLE 3

Synthesis of [(5-methoxy-2-benzimidazolyl) thio](4-methoxy-3,5-dimethyl-2-pyridyl)acetonitrile To a solution of 2-mercapto-5-methoxybenzimidazole (15.1 g, 0.14 mole) dissolved in 40 ml of 8.4% sodium hydroxide, was added 170 ml of methanol, followed by bromo(4-methoxy-3,5-dimethyl-2-pyridyl)acetonitrile(21.4 g, 0.11 mole) at room temperature. The mixture was heated to reflux for 1 h under a nitrogen atmosphere. The resulting precipitate was removed by filtration and the methanol was evaporated. The residue obtained was extracted with chloroform, and the chloroform was washed 3 times with water and dried over magnesium sulfate. After evaporation of the solvent, the crude product was recrystallized from diethyl ether to give 22.6 g (90%) of the title compound as yellowish crystals: mp 193–197° C.; $^1$H NMR (CDCl$_3$)δ 8.25 (s, 1H), 7.65 (dd, 1H), 7.30 (m, 1H), 6.90 (m, 1H), 6.30 (br s, 2H), 3.95 (s, 3H), 3.75 (s, 3H), 2.50 (s, 3H), 2.20 (s, 3H) ppm.

EXAMPLE 4

Synthesis of 3-[oxo(2-pyridyl)methyl]imidazo[1,2-d]-1,2,4-thiadiazole

To a solution of [(2-imidazolyl)thio](2-pyridyl) acetonitrile (30 mg, 0.14 mmole) in 5 ml of chloroform, was added portionwise 0.12 g of 60% m-chloroperbenzoic acid (0.42 mmol). The mixture was stirred at room temperature for 10 h. The resulting mixture was washed with water and saturated sodium bicarbonate solution. The organic phase was then treated with charcoal, and filtered to give the crude product. Chromatography on silica gel (100% ethyl acetate) affords 22 mg (84 %) of the title compound as a yellowish solid: mp 147–148° C.; $^1$H NMR (CDCl$_3$)δ 8.87 (d, 1H), 8.30 (m, 2H), 7.95 (m, 1H), 7.57 (m, 1H), 7.52 (m, 1H) ppm; IR (KBr)ν 1700, 1660 cm$^{-1}$; MS m/z 230 (M$^+$); HRMS calcd for C$_{10}$H$_6$N$_4$OS 230.0262, found: 230.0267.

EXAMPLE 5

Synthesis of 7-methoxy-3-[(4-methoxy-3,5-dimethyl-2-pyridyl)oxomethyl]-1,2,4-thiadiazolo[4,5-a]benzimidazole and 6-methoxy-3-[(4-methoxy-3,5-dimethyl-2-pyridyl) oxomethyl]-1,2,4-thiadiazolo[4,5-a]benzimidazole To a solution of [(5-methoxy-2-benzimidazolyl) thio](4-methoxy-3,5-dimethyl-2-pyridyl)acetonitrile (5.31 g, 15 mmole) in 400 ml of chloroform, was added dropwise 60% m-chloroperbenzoic acid (8.62 g, 30 mmole) dissolved in 100 ml of chloroform at 0–5° C. during a period of 1 h. After the addition was over, the reaction mixture was stirred at room temperature for 1 h. The resulting mixture was then washed with water and dried over magnesium sulfate. The solvent was evaporated to give the crude product. Chromatography on silica gel (ethyl acetate: hexane 1:1) yields 0.828 g (10%) of 7-methoxy-3-[(4-methoxy-3,5-dimethyl-2-pyridyl)oxomethyl]-1,2,4-thiadiazolo[4,5-a] benzimidazole as a yellowish solid and 0.828 g (10%) of 6-methoxy-3-[(4-methoxy-3,5-dimethyl-2-pyridyl) oxomethyl]-1,2,4-thiadiazolo[4,5-a]benzimidazoleas a solid.

7-methoxy-3-[(4-methoxy-3,5-dimethyl-2-pyridyl) oxomethyl]-1,2,4-thiadiazolo[4,5-a]benzimidazole: mp 170–171° C.; $^1$H NMR (DMSO-$d_6$)δ 8.34 (s, 1H), 7.86 (d, 1H), 7.29 (d, 1H), 6.93 (dd, 1H), 3.84 (s, 6H), 2.42 (s, 3H), 2.31 (s, 3H) ppm; IR (KBr)ν 1684, 1654 cm$^{-1}$; MS m/z 369 (M$^+$+1).

6-methoxy-3-[(4-methoxy-3,5-dimethyl-2-pyridyl) oxomethyl]-1,2,4-thiadiazolo[4,5-a]benzimidazole: mp 196–197° C.; $^1$H NMR (DMSO-$d_6$)δ 8.34 (s, 1H), 7.67 (d, 1H)$_1$ 7.34 (d, 1H), 7.10 (dd, 1H), 3.84 (s, 3H), 3.74 (s, 3H),2.44 (s, 3H),2.31 (s, 3H) ppm; IR (KBr)ν 1684 cm$^{-1}$; MS ml/z 369 (M$^+$+1).

EXAMPLE 6

Synthesis of dibromo(2-pyridyl)acetonitrile

To a solutionr of (2-pyridyl)acetonitrile (6.0 g, 50.8 mmol) in 120 mL carbon tetrachloride was added N-bromosuccinimide (18.5 g, 104 mmol) at room temperature. The resulting mixture was heated to reflux for 22 h. After cooling, the precipitate was filtered. The car bon tetrachloride was evaporated to give 13.5 g (96%) of dibromo(2-pyridyl)acetonitrile as a dark-brown solid: mp 59–61° C.; $^1$H NMR (CDCl$_3$)δ 8.62 (d, 1H), 7.93 (d, 1H), 7.86 (dt, 1H), 7.35 (dt, 1H) ppm; $^{13}$C NMR (CDCl$_3$)δ 155.23, 148.94, 138.24, 125.38, 120.55, 115.81, 30.81 ppm; HRMS calcd for C$_7$H$_4$N$_2$Br$_2$: 273.8741, found: 273.8730.

EXAMPLE 7

Synthesis of 2-butyl-1,2,4-thiadiazolo[4,5-a]benzimidazole-3 (2H)-one

The mixture of 2-mercaptobenzimidazole (29.30 g, 0.195 mole) and butyl isocyanate (48.3 mL, 0.33 mole) in a 500 ml of round-bottom flask equipped with a condenser was heated to 130–140° C. in an oil bath for 45 min. After the reaction mixture was cooled to room temperature, the solid was filtered, washed with hexane, and dried under vacuum to give 43.48 g (89%) of 1-(butylcarbamoyl)-1,3-dihydrobenzimidazole-2-thione as white crystals: mp 179–180° C.

To a solution of 1-(butylcarbamoyl)-1,3-dihydrobenzimidazole-2-thione (39.89 g, 0.16 mole) in 250 mL of chloroform, was added 25.57 g (0.16 mole) of bromine, in 110 mL of chloroform, at 0° C. After the addition was complete, triethylamine (44.6 mL, 0.32 mole), in 80 mL of chloroform, was added dropwise to the reaction mixture. The mixture was stirred at 0° C for an additional 4 h, and then stirred at room temperature for 14 h. The resulting mixture was washed with water and then with a 10% sodium sulfate solution. The organic layer was dried over magnesium sulfate and evaporated to give the crude product. Recrystallization from methanol gave 27.10 g (69%) of 2-butyl-1,2,4-thiadiazolo[4,5-a]benzimidazole-3 (2H)-one as colourless crystals: mp 153–154° C. (lit.: 156–157° C., Martin et al. Tetrahedron 1983, 39, 2311).

In a similar manner, by replacing n-butyl isocyanate with other alkyl isocyanates, the following compounds were made:
2-ethyl-1,2,4-thiadiazolo[4,5-a]benzimidazole-3(2H)-one
2-isopropyl-1,2,4-thiadiazolo[4,5-a]benzimidazole-3 (2H)-one
2-methyl-1,2,4-thiadiazolo[4,5-a]benzimidazole-3(2H)-one
2-phenyl-1,2,4-thiadiazolo[4,5-a]benzimidazole-3(2H)-one
2-benzyl-1,2,4-thiadiazolo[4,5-a]benzimidazole-3(2H)-one

EXAMPLE 8

Synthesis of 3-[dibromo(2-pyridyl)methyl]-1,2,4-thiadiazolo [4,5-a]benzimidazole A mixture of 2-butyl-1,2,4-thiadiazolo[4,5-a]benzimidazole-3(2H)-one (2.0 g, 8.1 mmol) and dibromo(2-pyridyl)acetonitrile (4.91 g, 17.8 mmol) in 50 mL of dichloromethane was heated to reflux for 16 h. After cooling to room temperature, the precipitate was filtered, washed with dichloromethane and dried to give 2.76 g (80%) of the title compound as a light-brown solid: mp 195° C. (dec); $^1$H NMR (CDCl$_3$)δ 8.25 (m, 2H), 7.96 (dt, 1H), 7.76 (d, 1H), 7.32 (m, 2H), 6.95 (t, 1H), 6.92 (s, 1H) ppm; $^{13}$C NMR (CDCl$_3$)δ 166.08, 157.95, 150.34, 148.28, 147.71, 138.31, 128.76, 124.79, 124.58, 122.94, 121.68, 119.49, 113.97, 54.37 ppm; HRMS calcd for $C_{14}H_8Br_2N_4S$: 421.8836, found: 421.8850.

EXAMPLE 9

Synthesis of 3-(oxophenylmethyl)-1,2,4-thiadiazolo[4,5-a]benzimidazole

A mixture of 2-butyl-1,2,4-thiadiazolo[4,5-a]benzimidazole-3(2H)-one (6.0 g, 24.3 mmole) and benzoyl cyanide (6.36 g, 48.5 mmole) in 80 mL of dichloromethane was stirred at room temperature for 24 h. The precipitate was filtered and washed with dichloromethane. The crude product was recrystallized from acetone to give 6.48 g (96%) of 3-(oxophenylmethyl)-1,2,4-thiadiazolo[4,5-a]benzimidazole as yellow crystals: mp 190–191° C.; $^1$H NMR (CDCl$_3$)δ 8.35 (d, 3H), 7.82 (d, 1H), 7.73 (t, 1H), 7.59 (t, 2H), 7.50 (t, 1H), 7.36 (t, 1H) ppm; $^{13}$C NMR (CDCl$_3$)δ 180.86, 163.69, 150.82, 146.70, 134.79, 134.34, 131.22 (2C), 129.46 (2C), 128.74, 125.82, 122.27, 119.49, 115.23 ppm; IR (KBr)ν 1671 cm$^{-1}$; HRMS calcd for $C_{15}H_9N_3OS$: 279.0466, found: 279.0475. Anal. Calcd for $C_{15}H_9N_3OS$: C, 64.50;H, 3.25; N, 15.04. Found: C, 63.93;H, 3.10; N, 14.53.

In a similar manner, by replacing benzoyl cyanide with pyruvonitrile, the following compound was made:
3-(1-oxoethyl)-1,2,4-thiadiazolo[4,5-a]benzimidazole: mp 180–181° C.; $^1$H NMR (CDCl$_3$)δ 8.70 (d, 1H), 7.80 (d, 1H), 7.50 (t, 1H), 7.38 (t, 1H), 2.83 (s, 3H); $^{13}$C NMR (CDCl$_3$)δ 187.02, 164.15, 150.69, 147.78, 129.63, 125.82, 122.26, 119.27, 115.94, 26.74 ppm; IR (KBr)ν 1703 cm$^{-1}$. HRMS calcd for $C_{10}H_7N_3OS$: 217.0310, found: 217.0318. Anal. Calcd for $C_{10}H_7N_3OS$: C, 55.29;H, 3.25; N, 19.34. Found: C, 55.31;H, 3.29; N, 19.46.

In a similar manner, by replacing benzayl cyanide with other cyanides, the following compounds are made:
3-(1-oxopropyl)-1,2,4-thiadiazolo[4,5-a]benzimidazole
3-(1-oxobutyl)-1,2,4-thiadiazolo[4,5-a]benzimidazole
3-(1-oxo-2-phenylethyl)-1,2,4-thiadiazolo[4,5-a]benzimidazole
3-(cyclopentyloxomethyl)-1,2,4-thiadiazolo[4,5-a]benzimidazole
3-(1-oxo-2-phthalimidoethyl)-1,2,4-thiadiazolo[4,5-a]benzimidazole

EXAMPLE 10

Synthesis of 3-methyl-1,2,4-thiadiazolo[4,5-a]benzimidazole

2-Butyl-1,2,4-thiadiazolo[4,5-a]benzimidazole-3(2H)-one (1.00 g, 4.04 mmol) was refluxed in 100 mL acetonitrile for 18 h. The solvent was then evaporated and the residue was recrystallized from methanol to give 0.671 g (88%) of the title compound: mp 192–193° C.; $^1$H NMR (CDCl$_3$)δ 7.81 (dm, 2H), 7.47 (td, 1H), 7.34 (td, 1H), 2.92 (s, 3H) ppm; IR (KBr)ν 1564, 1481, 1453, 1430, 1304, 1208, 756, 745 cm$^{-1}$; MS m/z 189 (M$^+$), 148 (M$^+$–CH,CN)

In a similar manner, by replacing acetonitrile with other alkyl nitriles, the following compounds are prepared:
3-ethyl-1,2,4-thiadiazolo[4,5-a]benzimidazole
3-isopropyl-1,2,4-thiadiazolo[4,5-a]benzimidazole
3-(2-methylpropyl)-1,2,4-thiadiazolo[4,5-a]benzimidazole

EXAMPLE 11

Synthesis of 3-([4-(methoxycarbonyl)phenyl])-1,2,4-thiadiazolo[4,5-a]benzimidazole A mixture of 2-butyl-1,2,4-thiadiazolo[4,5-a]benzimidazole-3(2H)-one (0.3 g, 1.2 mmole) and methyl 4-cyanobenzoate (0.41 g, 2.5 mmole) in 7 mL of dichloromethane was heated to reflux for 20 h. The precipitate was filtered and washed with dichloromethane to give 0.16 g (48%) of 3-([4-(methoxycarbonyl)]phenyl-1,2,4-thiadiazolo[4,5-a]benzimidazole as a white solid: mp 204–206° C.; $^1$H NMR (CDCl$_3$)δ 8.33 (d, 2H), 7.98 (d, 2H), 7.83 (d, 1H), 7.49 (m, 2H), 7.20 (t, 1H), 4.02 (s, 3H) ppm; $^{13}$C NMR (CDCl$_3$)δ 165.96, 165.30, 151.08, 149.10, 133.16, 132.55, 130.24(2C), 128.69(3C), 125.34, 121.58, 119.96, 112.01, 52.56 ppm; IR (KBr)ν 1729, 1508, 1448, 1275, 733 cm$^{-1}$; HRMS calcd for $C_{16}H_{11}N_3OS$, 309.0572 found 309.05719.

EXAMPLE 12

Synthesis of 3-(4-methylphenylsulfonyl)-1,2,4-thiadiazolo[4,5-a]benzimidazole

A mixture of 2-butyl-1,2,4-thiadiazolo[4,5-a]benzimidazole-3(2H)-one (10.0 g, 40.4 mmole) and p-toluenesulfonyl cyanide (14.7 g, 81.0 mmole) in 120 mL of dichloromethane was stirred at room temperature for 20 h. The precipitate was filtered and washed with dichloromethane to yield 12.2 g (91%) of 3-(4-methylphenylsulfonyl)-1,2,4-thiadiazolo[4,5-a]benzimidazole as white powder: mp 231–234° C.; $^1$H NMR (CDCl$_3$)δ 8.53 (d, 1H), 8.04 (d, 2H), 7.82 (d, 1H), 7.56–7.44 (m, 4H), 2.53 (s, 3H) ppm; $^{13}$C NMR (CDCl$_3$)δ 163.72, 150.38, 147.97, 147.54, 132.48, 130.30(2C), 129.97(2C), 128.49, 126.14, 123.06, 119.70, 114.67, 21.93 ppm; IR (KBr)ν 1592, 1525, 1444, 1337, 1151, 1081, 735 cm$^{-1}$; HRMS calcd for $C_{15}H_{11}N_3O_2S_2$: 329.0293, found: 329.0300. Anal. Calcd for $C_{15}H_{11}N_3O_2S_2$: C, 54.70;Hf 3.37; N, 12.76. Found: C, 54.29;H, 3.14; N, 14.59.

EXAMPLE 13

Synthesis of 3-(methoxycarbonyl)-1,2,4-thiadiazolo[4,5-a]benzimidazole

A mixture of 2-butyl-1,2,4-thiadiazolo[4,5-a]benzimidazole-3(2H)-one (4.0 g, 16.2 mmole) and methyl cyanoformate (2.75 g, 32.4 mmole) in 30 mL of dichloromethane was stirred at room temperature for 21 h. The precipitate was filtered and washed with dichloromethane to give 3.36 g (84%) of 3-(methoxycarbonyl)-1,2,4-thiadiazolo [4,5-a]benzimidazole as a colourless solid: mp 208–209° C.; $^1$H NMR (CDCl$_3$)δ 8.61 (d, 1H), 7.82 (d, 1H), 7.51 (t, 1H), 7.31 (t, 1H), 4.17 (s, 3H) ppm; $^{13}$C NMR (CDCl$_3$)δ 164.02, 156.51, 150.67, 140.89, 129.34, 125.93, 122.41, 119.48, 115.41, 54.04 ppm; IR (KBr)ν 1733 cm$^{-1}$; HRMS calcd for $C_{10}H_7N_3O_2S$ 233.0259, found 233.0262. Anal. Calcd. for $C_{10}H_7N_3O_2S$: C, 51.50;H, 3.02; N, 18.02. Found: C, 51.41;H. 2.89; N, 18.16.

In a similar manner, by replacing methyl cyanoformate with other cyanoformates, the following compounds are made:
3-(ethoxycarbonyl)-1,2,4-thiadiazolo[4,5-a]benzimidazole
3-(butoxycarbonyl)-1,2,4-thiadiazolo[4,5-a]benzimidazole
3-(isopropoxycarbonyl)-1,2,4-thiadiazolo[4,5-a] benzimidazole
3-[(benzyloxy)carbonyl]-1,2,4-thiadiazolo[4,5-a] benzimidazole
3-[(cyclopentyloxy)carbonyl]-1,2,4-thiadiazolo[4,5-a] benzimidazole.

EXAMPLE 14

Synthesis of 3-(2-pyridyl)-1,2,4-thiadiazolo[4,5-a]benzimidazole

A mixture of $^2$-butyl-1,2,4-thiadiazolo[4,5-a]benzimidazole-3(2H)-one (15.0 g, 60.7 mmole) and 2-cyanopyridine (13.3 g, 0.13 mole) in 150 mL of dichloromethane was stirred at room temperature for 72 h. The precipitate was filtered and washed with dichloromethane to give 10.4 g (68%) of 3-(2-pyridyl)-1,2,4-thiadiazolo[4,5-a]benzimidazole as a white solid: mp 173–174° C.; $^1$H NMR $(CDCl_3)\delta$ 8.90 (d, 1H), 8.70 (d, 1H), 8.30 (d, 1H), 7.99 (t, 1H), 7.80 (d, 1H), 7.57 (t, 1H), 7.47 (t, 1H), 7.37 (t, 1H) ppm; $^{13}$C NMR $(CDCl_3)\delta$ 166.10, 151.09, 150.11, 148.74, 147.73, 137.38, 130.50, 125.85, 125.24, 124.52, 121.41, 119.11, 116.33 ppm; IR (KBr)ν 3419, 3054, 1611, 1587, 1501, 1463, 1446, 727 cm$^{-1}$. HRMS calcd for $C_{13}H_8N_4S$ 252.0470, found 252.0882. Anal. Calcd for $C_{13}H_8N_4S$: C, 61.89;H, 3.20; N, 22.21. Found: C, 61.48;H, 3.30; N, 22.24.

EXAMPLE 15

Synthesis of 3-amino-1,2,4-thiadiazolo[4,5-a]benzimidazole

To a cooled solution of 2-butyl-1,2,4-thiadiazolo[4,5-a]benzimidazole-3(2H)-one (2.00 g, 8.08 mmole) in 25 mL dichloromethane, cyanamide (0.728 g, 16.2 mmole) was added in one portion and the mixture was stirred for 48 h at room temperature. The resulting precipitate was filtered, slurried in methanol and subsequently washed with dichloromethane to give 1.01 g (66%) of 3-amino-1,2,4-thiadiazolo[4,5-a]benzimidazole as colourless crystals: mp 255–256° C.; $^1$H NMR (DMSO-d$_6$)δ 8.23 (d, 1H), 7.71 (d, 1H), 7.43 (t, 1H), 7.54 (s, 2H), 7.32 (t, 1H) ppm; IR (KBr)ν 3302, 3151, 1661, 1577, 1487, 1473, 1251, 1207, 810 cm$^{-1}$; HRMS calcd for $C_8H_6N_4S$ 190.0313, found 190.0293. Anal. Calcd for $C_8H_6N_4S$: C, 50.51;H. 3.18; N. 29.45. Found: C, 50.26;H, 3.26; N, 29.38.

EXAMPLE 16

Synthesis of 3-bromo-1,2,4-thiadiazolo[4,5-a]benzimidazole

A mixture of 2-butyl-1,2,4-thiadiazolo[4,5-a]benzimidazole-3(2H)-one (5.0 g, 20.2 mmole) and cyanogen bromide (4.28 g, 40.4 mmole) in 100 mL of dichloromethane was stirred at room temperature for 26 h. The precipitate was filtered and washed with dichloromethane to yield 4.18 g (81%) of 3-bromo-1,2,4-thiadiazolo[4,5-a]benzimidazole as a white powder: mp 189–190° C.; $^1$H NMR $(CDCl_3)\delta$ 8.23 (d, 1H), 7.82 (d, 1H), 7.52 (t, 1H), 7.42 (d, 1H) ppm; $^{13}$C NMR (1:1 CDCl$_3$:DMSO-d$_6$):δ 162.78, 149.67, 129.22, 125.53, 122.25, 119.48, 117.25, 111.27 ppm; IR (KBr):ν 3025, 2925, 1601, 1493, 1451, 1028, 757, 701 cm$^{-1}$; HRMS calcd for $C_8H_4N_3SBr$ 252.9309, found 252.9307. Anal. Calcd for $C_8H_4N_3SBr$: C, 37.81;H, 1.59; N, 16.54. Found: C, 37.44; H, 1.33; N. 16.57.

In a similar manner, by replacing cyanogen bromide with other cyanogen halides, the following compounds are made:
3-iodo-1,2,4-thiadiazolo[4,5-a]benzimidazole
3-chloro-1,2,4-thiadiazolo[4,5-a]benzimidazole

EXAMPLE 17

Synthesis of 3-[oxo(2-pyridyl)methyl]-1,2,4-thiadiazolo[4,5-a]benzimidazole

To a solution of 3-[dibromo(2-pyridyl)methyl]-1,2,4-thiadiazolo[4,5-a]benzimidazole (2.02 g, 4.76 mmol) in 75 mL tetrahydrofuran was added a solution of silver nitrate (0.890 g, 5.24 mmol) in 75 mL water. The suspension was stirred for 2 days and then basified to pH 6 with aqueous sodium bicarbonate. After the addition of 1 mL saturated aqueous sodium chloride, the mixture was filtered on celite and the celite was washed with ethyl acetate. After extraction with water, the ethyl acetate was dried and evaporated to give a crude residue which was purified by flash chromatography using a mixture of chloroform/methanol 10:0.1 as the eluent. 1.05 g (78%) of the title compound was obtained as a yellow solid: mp 182–186° C. (dec); $^1$H NMR $(CDCl_3)\delta$ 8.85 (m, 1H), 8.31 (dt, 1H), 8.19 (d, 1H), 8.01 (td, 1H), 7.83 (d, 1H), 7.63 (ddd, 1H), 7.50 (ddd, 1H), 7.35 (ddd, 1H) ppm; IR (film) 1673, 1511, 1444, 1235, 1057, 879, 733 cm$^{-1}$; MS m/z 280 (M$^+$), 148 (M$^+$-(2-pyridyl)C(O)CN).

EXAMPLE 18

Synthesis of 3-[bis(ethoxycarbonyl)methyl]-1,2,4-thiadiazolo[4,5-a]benzimidazole A mixture of 3-bromo-1,2,4-thiadiazolo[4,5-a]benzimidazole (0.2 g, 0.78 mmole), diethyl malonate (0.15 g, 0.94 mmol) and triethylamine (0.13 mL, 0.94 mmole) in 8 mL of THF was refluxed under a nitrogen atmosphere for 36 h. The resulting mixture was extracted with ethyl acetate, washed with water and 10% aqueous sodium sulfate. The organic layer was dried over magnesium sulfate to give the crude product, which was purified by flash chromatography (35% ethyl acetate:65% hexane) to afford 0.14 g (54%) of the title compound as a yellow oil:

$^1$H NMR (CDCl,)δ 9.48 (s, 1H), 8.06 (d, 1H), 7.63 (d, 1H), 7.34–7.31 (m, 2H), 4.39 (q, 4H), 1.35 (t, 6H) ppm; IR (film) 1748 cm$^{-1}$. HRMS calcd for $C_{15}H_{15}N_3O_4S$ 333.0783, found 333.0794.

EXAMPLE 19

Synthesis of 3-methoxy-1,2,4-thiadiazolo[4,5-al benzimidazole

To a cooled mixture of 3-bromo-1,2,4-thiadiazolo [4,5-a] benzimidazole (4.55 g, 17.9 mmole) in 50 mL of methanol, sodium methoxide (0.967 g, 17.9 mmole) was added in one portion and stirred for 4 h at room temperature. The reaction mixture was evaporated to dryness under vacuum and the residue was taken-up in ethyl acetate and washed with water. The organic layer was dried with sodium sulfate, filtered and evaporated to yield 3.64 g (94%) of 3-methoxy-1,2,4-thiadiazolo[4,5-a]benzimidazole as colourless crystals: mp 172–175° C.; $^1$H NMR $(CDCl_3)\delta$ 7.83 (d, 1H), 7.75 (d, 1H), 7.42 (t, 1H), 7.27 (t, 1H), 4.32 (s, 3H) ppm; $^{13}$C NMR $(CDCl_3)\delta$ 163.2, 150.3, 148.1, 128.2, 124.9, 121.8, 119.2, 111.7, 57.5 ppm; IR (KBr)ν 3418, 2942, 1595, 1492, 1404, 1275, 1255, 1206, 1083, 755 cm$^{-1}$. Anal. Calcd for $C_9H_7N_3OS$: C, 52.67;H, 3.44; N, 20.49. Found: C, 52.28; H, 3.36; N, 20.45.

In a similar manner, by replacing sodium methoxide with other metal alkyloxides, the following compounds are made:
3-ethoxy-1,2,4-thiadiazolo[4,5-a]benzimidazole
3-propoxy-1,2,4-thiadiazolo[4,5-a]benzimidazole
3-isopropoxy-1,2,4-thiadiazolo[4,5-a]benzimidazole 3-butoxy-1,2,4-thiadiazolo[4,5-a]benzimidazole
3-tert-butoxy-1,2,4-thiadiazolo[4,5-a]benzimidazole
3-(cyclopentyloxy)-1,2,4-thiadiazolo[4,5-a]benzimidazole

EXAMPLE 20
Synthesis of 3-(dimethylamino)-1,2,4-thiadiazolo[4,5-a]benzimidazole To a cooled mixture of 3-bromo-1,2,4-thiadiazolo [4,5-a]benzimidazole (15.44 g, 0.0603 mole) in 100 mL dichloromethane, dimethylamine (40% solution in water) (5.44 g, 0.121 mole) was added dropwise. The reaction mixture was allowed to stir for 16 h at room temperature. It was then diluted with dichloromethane, washed with water, dried with sodium sulfate and evaporated under vacuum to give 10.47 g (80%) of 3-(dimethylamino)-1,2,4-thiadiazolo[4,5-a]benzimidazole as colourless crystals: mp 102–104° C.; $^1$H NMR (CDCl$_3$)δ 7.74 (t, 2H), 7.41 (t, 1H), 7.27 (t, 1H), 3.06 (s, 6H) ppm. Anal. Calcd for C$_{10}$H$_{10}$N$_4$S: C, 55.03;H, 4.62; N, 25.69. Found: C, 54.53;H, 4.90; N, 25.50.

In a similar manner, by replacing dimethylamine with other amines, the following compounds were made:
3-(ethylamino)-1,2,4-thiadiazolo[4,5-a]benzimidazole: mp 164.5–165° C. (dec); $^1$H NMR (CDCl$_3$)δ 7.78 (m, 2H), 7.65 (d, 1H), 7.43 (t, 1H), 7.21 (t, 1H) 3.68 (q, 2H), 1.45 (t, 3H)
3-(1-pyrrolyl)-1,2,4-thiadiazolo[4,5-a]benzimidazole: mp 118–119° C.; $^1$H NMR (CDCl$_3$)δ 7.77 (t, 2H), 7.43 (t, 1H), 7.28 (t, 1H), 3.71 (m, 4H), 2.07 (m, 4H) ppm.
3-(4-morpholinyl)-1,2,4-thiadiazolo[4,5-a]benzimidazole: mp 140–142° C.; $^1$H NMR (CDCl$_3$)δ 7.78 (d, 1H), 7.60 (d, 1H), 7.45 (t, 1H), 7.32 (t, 1H), 3.99 (m, 4H), 3.48 (m, 4H) ppm.
3-(1-piperazinyl)-1,2,4-thiadiazolo[4,5-a]benzimidazole: mp 116–118° C.; $^1$H NMR (CDCl$_3$)δ 7.76 (d, 1H), 7.63 (d, 1H), 7.42 (t, 1H), 7.30 (t, 1H), 3.41 (m, 4H), 3.15 (t, 4H), 2.00 (br s, 1H) ppm.
3-(4-methyl-1-piperazinyl)-1,2,4-thiadiazolo[4,5-a]benzimidazole: mp 158–158.5° C.; $^1$H NMR (CDCl$_3$)δ 7.77 (d, 1H), 7.64 (d, 1H), 7.42 (t, 1H), 7.32 (t, 1H), 3.49 (m, 4H), 2.70 (m, 4H), 2.43 (s, 3H) ppm.
3-[[2-(methoxycarbonyl)methyl]amino]-1,2,4-thiadiazolo[4,5-a]benzimidazole: mp 196–197° C. Anal. Calcd for C$_{11}$H$_{10}$N$_4$O$_2$S: C, 50.37;H, 3.84; N, 21.36. Found: C, 50.13;H, 3.96; N, 21.26.

In a similar manner, by replacing dimethylamine with other nucleophilic amines, the following compound is made:
3-(methylamino)-1,2,4-thiadiazolo[4,5-a]benzimidazole

EXAMPLE 21
Synthesis of 3-[(hydroxyimino)phenylmethyl]-1,2,4-thiadiazolo[4,5-a]benzimidazole To a solution of 0.5 g (1.79 mmol) of 3-(oxophenylmethyl)-1,2,4-thiadiazolo[4,5-a]benzimidazole in 7 mL of ethanol was added 0.5 mL (6.46 mmol) of pyridine and 0.5 g (7.20 mmol) of hydroxylamine hydrochloride. The mixture was refluxed for overnight. The precipitate was collected by filtration, and washed with methanol and dichloromethane to give the crude product, which was recrystallized from methanol to yield 0.47 g (89%) of the title compound as white crystals. mp 247° C.; $^1$H NMR (DMSO-d$_6$)δ 11.89 (s, 1H), 7.81 (d, 1H), 7.73 (dd, 2H), 7.45–7.53 (m, 5H), 7.32 (t, 1H) ppm; $^{13}$C NMR (CDCl$_3$)δ 168.25, 155.24, 150.52, 147.95, 136.94, 135.67, 134.30(2C), 133.03, 131.52(2C), 130.35, 127.26, 124.28, 116.91 ppm; IR (KBr)δ 2731, 1549, 1475, 1450, 1251, 1194, 983, 753, 736 cm$^{-1}$ HRMS calcd for C$_{15}$H$_{10}$N$_4$OS 294.0575, found 294.0583

EXAMPLE 22
Synthesis of 3-(1-hydroxyethyl)-1,2,4-thiadiazolo[4,5-a]benzimidazole To a suspension of 3-(1-oxoethyl)-1,2,4-thiadiazolo[4,5-a]benzimidazole (729 mg, 3.36 mmol) in 200 mL methanol, was added sodium borohydride (140 mg, 3.69 mmol). The mixture was stirred for 30 min and 0.1 mL of water was added. The methanol was evaporated and the residue was partitioned between ethyl acetate and 0.1 M hydrochloric acid. The aqueous phase was extracted with ethyl acetate. The organic phases were combined, washed twice with brine, dried and evaporated. The crude residue was purified by chromatography using chloroform/methanol to give 3-(1-hydroxyethyl)-1,2,4-thiadiazolo[4,5-a]benzimidazole. mp 174–175° C.; $^1$H NMR (CDCl$_3$)δ 8.05 (d, 1H), 7.80 (d, 1H), 7.47 (td, 1H), 7.36 (td, 1H), 5.39 (q, 1H), 2.76 (d, 1H), 1.84 (d, 3H) ppm; IR (KBr)v 3136, 1544, 1494, 1478, 1451, 1374, 1250, 1200, 1123, 1103, 1093, 752, 729, 711 cm$^{-1}$; MS m/z 219 (M$^+$), 148 (M$^+$–CH,CH(OH)CN)

EXAMPLE 23
Synthesis of 3-carboxy-1,2,4-thiadiazolo[4,5-a]benzimidazole

To a 6 mL solution of 1N NaOH, 3-(methoxycarbonyl)-1,2,4-thiadiazolo[4,5-a]benzimidazole (1.0 g, 4.3 mmole) in 6 mL of dioxane, was added. The reaction mixture was stirred at room temperature until completion. The resulting mixture was then acidified with 3N HCl to pH ~2.0, and stirred at room temperature for an additional 0.5 h. The solid was filtered, washed with water, and dried under vacuum at 60° C. for 24 h to yield 0.74 g (78%) of the title compound as a colourless solid: mp 184–185° C. (dec); $^1$H NMR (DMSO-d$_6$)δ 13.79 (br s, 1H), 8.59 (d, 1H) 7.78 (d, 1H), 7.51 (t, 1H), 7.40 (t, 1H); IR (KBr)v 3435, 1705 cm$^{-1}$; MS m/z 193 (M$^+$–OH), 175 (M$^-$—CO$_2$).

EXAMPLE 24
Synthesis of sodium 3-carboxylato-1,2,4-thiadiazolo[4,5-al]benzimidazole To a suspension of 3-carboxy-1,2,4-thiadiazolo [4,5-a]benzimidazole (10.00 g, 45.62 mmol) in methanol (150 ml) and water (100 ml), 1M NaOH (45.6 ml) was added over a period of 1 h. After 4 h, the solution turned clear and the methanol was removed under reduced pressure. The aqueous solution was extracted with chloroform, the aqueous phase was freeze-dried to give the title compound (10.4 g, 95%) as a white solid: mp 225–227° C.; $^1$H NMR (DMSO-d$_6$)δ 7.68 (d, 1H), 7.05 (d, 1H), 6.95 (t, 1H), 6.80 (t, 1H) ppm; $^{13}$C NMR (DMSO-d$_6$)δ 167.20, 161.76, 149.68, 148.84, 129.52, 126.23, 122.74, 118.37, 116.06 ppm; IR (KBr)v 3395, 3243, 1663, 1641, 1522, 1443, 1334, 827, 729 cm$^{-1}$.

EXAMPLE 25
Preparation of 3-(4-methyl-1-piperazinyl)-1,2,4-thiadiazolo[4,5-a]benzimidazole dihydrochloride To a clear solution of 3-(4-methyl-1-piperazinyl) -1,2,4-thiadiazolo[4,5-a]benzimidazole (6.07 g, 22.21 mmol) in 100 ml of dichloromethane, hydrogen chloride gas was bubbled through for 40 min. The solution became turbid with time. The suspension was filtered and dried under vacuum to give the title compound as a fine white powder 7.60 g (99%). mp 252° C. (dec); $^1$H NMR (DMSO-d$_6$ & D$_2$O)δ 7.85 (d, 2H), 7.60 (t, 1H), 7.51 (t, 1H), 3.86 (m, 2H), 3.56 (m, 6H), 2.91 (s, 3H) ppm; $^{13}$C NMR (DMSO-d$_6$ & D$_2$O)δ 164.39, 148.80, 144.27, 126.92, 126.12, 123.41, 117.08, 113.20, 51.19, 45.87, 42.32 ppm; IR (KBr)v 3420, 1606, 1571, 1475, 1461, 1225, 981, 761 cm$^{-1}$.

EXAMPLE 26

Preparation of 2-butylimidazo[1,2-d]-1,2,4-thiadiazole-3(2H)-one

2-Mercaptoimidazole (24.39 g, 0.244 mole) and butyl isocyanate (48.3 g, 0.487 mole) were combined in a round-bottom flask and heated to 50° C. for 30 min or until the reaction was complete by TLC. The reaction mixture was then cooled to room temperature and the solidified mass was triturated with 50 mL of hexane for 30 min. The beige solid was filtered, washed with a minimum amount of hexane and dried under reduced pressure to yield 44.96 g (93%) of 1-(butylcarbamoyl)-1,3-dihydroimidazole-2-thione as beige crystals: mp 66–68° C.

To solution containing 1-(butylcarbamoyl)-1,3-dihydroimidazole-2-thione (4.73 g, 23.7 mmole) suspended in 15 mL of dichloromethane cooled to 0° C. under a nitrogen atmosphere, was added bromine (3.79 g, 23.7 mmole) dissolved in 15 mL of dichloromethane, in a dropwise manner. After the addition was complete, triethylamine (4.81 g, 47.5 mmole) dissolved in 15 mL dichloromethane was added such that the temperature of the reaction mixture never exceeded 0° C. The reaction mixture was maintained at 0° C. for an additional 2 h and then stirred for 16 h at room temperature. It was then diluted with 150 mL of dichloromethane and washed twice with water and once with a saturated sodium chloride solution. The organic layer was then dried over magnesium sulfate and evaporated to dryness to yield 4.30 g (92%) of 2-butylimidazo[1,2-d]-1,2,4-thiadiazole-3(2H)-one as an off-white powder: mp 142–143° C.; $^1$H NMR (CDCl$_3$)δ 7.40 (d, 1H), 7.20 (d, 1H), 3.79 (t, 2H), 1.73 (m, 2H), 1.40 (m, 2H), 0.957 (t, 3H) ppm; IR (KBr)ν 1702 cm$^{-1}$.

In a similar manner, by replacing butyl isocyanate with other selected isocyanates, the following compounds are made:

2-methylimidazo[1,2-d]-1,2,4-thiadiazole-3(2H)-one
2-ethylimidazo[1,2-d]-1,2,4-thiadiazole-3(2H)-one
2-propylimidazo[1,2-d]-1,2,4-thiadiazole-3(2H)-one
2-isopropylimidazo[1,2-d]-1,2,4-thiadiazole-3(2H)-one
2-pentylimidazo[1,2-d]-1,2,4-thiadiazole-3(2H)-one
2-hexylimidazo[1,2-d]-1,2,4-thiadiazole-3(2H)-one
2-cyclohexylimidazo[1,2-d]-1,2,4-thiadiazole-3(2H)-one
2-benzylimidazo[1,2-d]1,2,4-thiadiazole-3(2H)-one

EXAMPLE 27

Synthesis of 3-(1-oxoethyl)imidazo[1,2-d]-1,2,4-thiadiazole-3 (2H)-one

To a cooled solution of 2-butylimidazo[1,2-d]-1,2,4-thiadiazole-3(2H)-one (2.49 g, 12.6 mmole) in 5 mL of dichloromethane, pyruvonitrile (1.74 g, 25.2 mmole) was added dropwise and a llowed to stir for 24 h. The precipitate was then collected by filtration, washed with dichloromethane and evaporated by filtpressure to yield 0.662 g (31%) of 3-(1-oxoethyl)imidazo[1,2-d]-1,2,4-thiadiazole-3 (2H)-one as yellow-green crystals: mp 142–144° C.; $^1$H-NMR (CDCl$_3$)δ 8.23 (s, 1H), 7.51 (s, 1H), 2.78 (s, 3H) ppm; IR (KBr)ν 3436, 3168, 3106, 1516, 1408, 1363, 1229, 1136, 730 cm$^{-1}$. Anal. Calcd for C$_6$H$_5$N$_3$SO: C, 43.11;H, 3.01; N, 25.13. Found: C, 43.11;H. 2.91; N. 25.27.

In a similar manner, by replacing pyruvonitrile with benzoyl cyanide, the following compound was made:
3-(oxophenylmethyl)imidazo[1,2-d]-1,2,4-thiadiazole-3 (2H)-one: mp 166–168° C.; $^1$H NMR (CDCl$_3$)δ 8.44 (d, 2H), 8.40 (s, 1H), 7.70 (d, 1H), 7.58 (t, 3H) ppm.

In a similar manner, by replacing pyruvonitrile with other selected cyanide or nitriles, the following compounds are made:
3-(1-oxopropyl)imidazo[1,2-d]-1,2,4-thiadiazole-3(2H)-one
3-(1-oxobutyl)imidazo[1,2-d]-1,2,4-thiadiazole-3(2H)-one
3-(1-oxopentyl)imidazo[1,2-d]-1,2,4-thiadiazole-3(2H)-one
3-(1-oxohexyl)imidazo[1,2-d]-1,2,4-thiadiazole-3(2H)-one
3-(cyclopentyloxomethyl)imidazo[1,2-d]-1,2,4-thiadiazole-3(2H)-one
3-(1-oxo-2-phthalimidoethyl)imidazo[1,2-d]-1,2,4-thiadiazole-3(2H)-one

EXAMPLE 28

Synthesis of 3-(methoxycarbonyl)imidazo[1,2-d]-1,2,4-thiadiazole

To a cooled solution of 2-butylimidazo[1,2-d]-1,2,4-thiadiazole-3(2H)-one (2.95 g, 15.0 mmole) in 25 mL dichloromethane, methyl cyanoformate (2.54 g, 30 mmole) was added dropwise and the mixture was stirred for 16 h at room temperature. The precipitate was filtered and subsequently washed with dichloromethane to give 2.18 g (80%w) of 3-(methoxycarbonyl)imidazo[1,2-d]-1,2,4-thiadiazole as colourless crystals: mp 164.5–165° C.; $^1$H NMR (CDCl$_3$)δ 8.13 (s, 1H), 7.51 (s, 1H), 4.11 (s, 3H) ppm; IR (KBr)ν 3440, 1737, 1527, 1253, 1071 cm$^{-1}$. Anal. Calcd for C$_6$H$_5$N$_3$O$_2$S: C, 39.34;H, 2.75; N, 22.94. Found: C, 39.41;H, 2.51; N, 22.94.

In a similar manner, by replacing methyl cyanoformate with other cyanoformates, the following compounds are made:
3-(ethoxycarbonyl)imidazo[1,2-d]-1,2,4-thiadiazole
3-(propoxycabonyl)imidazo[1,2-d]-1,2,4-thiadiazole
3-(butoxycabonyl)imidazo[1,2-d]-1,2,4-thiadiazole
3-(isopropoxycarbonyl)imidazo[1,2-d]-1,2,4-thiadiazole
3-[(pentyloxy)cabonyl]imidazo[1,2-d]-1,2,4-thiadiazole
3-[(cyclopentyloxy)cabonyl]imidazo[1,2-d]-1,2,4-thiadiazole
3-[(benzyloxy)cabonyl]imidazo[1,2-d]-1,2,4-thiadiazole

EXAMPLE 29

Synthesis of 3-bromoimidazo[1,2-d]-1,2,4-thiadiazole

To a cooled solution of 2-butylimidazo[1,2-d]-1,2,4-thiadiazole-3(2H)-one (4.78 g, 0.0242 mole) in 25 mL dichloromethane, cyanogen bromide (5.13 g, 0.0482 mole) was added in one portion and the mixture was stirred for 16 h at room temperature. The precipitate was filtered, slurried in 10 mL of methanol and subsequently washed with dichloromethane to give 4.45 g (90%) of 3-bromoimidazo[1,2-d]-1,2,4-thiadiazole as a colourless powder: mp 220° C. (dec); MS in/z 205, 203 (M$^+$). Anal. Calcd for C$_4$H$_2$N$_3$SBr●½H$_2$O: C, 22.55;H, 1.42; N, 19.72; O, 3.75; S, 15.02; Br, 37.50. Found: Cf 22.79;H, 1.41; N, 19.42; O, 2.67; S, 14.61; Br, 38.20.

In a similar manner, by replacing cyanogen bromide with other cyanogen halides, the following compounds are made:
3-iodoimidazo[1,2-d]-1,2,4-thiadiazole
3-chloroimidazo[1,2-d]-1,2,4-thiadiazole

EXAMPLE 30

Synthesis of 3-methylsulfonyl-1,2,4-thiadiazolo[4,5-a]benzimidazole

To a solution of 3-methylthio-1,2,4-thiadiazolo [4,5-a]benzimidazole (100 mg, 0.45 mmole) in 10 mL dichloromethane was added m-chloroperbenzoic acid (287 mg, 0.95 mmole). The mixture was stirred at room temperature and the starting material was converted to the sulfoxide after a few hours; it was then further oxidized to the sulfone after 18 h. The solvent was then evaporated and the residue purified by chromatography using chloroform/methanol 10:0.1 as the eluent to yield 50 mg (44% of 3-methylsulfonyl-1,2,4-thiadiazolo[4,5-a]benzimidazole as white solid: mp 203–207° C. (dec); $^1$H NMR (CDCl$_3$)δ 8.31 (d, 1H), 7.84 (d, 1H), 7.54 (ddd, 1H), 7.43 (td, 1H), 3.63 (s, 3H) ppm; IR (KBr)ν 1530, 1487, 1444, 1324, 1315, 1193, 1147, 1141, 735 cm$^{-1}$, MS m/z 253 (M$^+$), 174 (M$^+$–CH$_3$SO$_2$), 148 (M$^+$–CH$_3$SO$_2$CN).

EXAMPLE 31

Synthesis of 3-[4-(2-pyridyl)piperazinyl]-1,2,4-thiadiazolo [4,5-a]benzimidazole To a cooled solution of 3-bromo-1,2-4-thiadiazolo [4,5-a]benzimidazole (0.30 g, 1.17 mmol) in 10 mL of dichloromethane, 2-pyridylpiperazine (0.54 mL, 3.51 mmol) was added dropwise and the mixture was allowed to stir for 16 h. The reaction mixture was diluted with 100 mL of dichloromethane and washed with water (2×30 mL) and then brine (1×25 mL). The organic layer was dried over sodium sulfate and evaporated to give a yellow oil which was purified by column chromatography (40% EtOAc; 60% hexane) to yield a white solid (0.27 g, 68.5%); $^1$H-NMR (CDCl$_3$)δ 3.58 (m, 4H, 2CH$_2$); 3.82 (m, 4H, 2CH$_2$), 6.75 (m, 2H, pyr-H), 7.30 (t, 1H, ArH), 7.44 (t, 1H, ArH), 7.55 (m, 1H, pyr-H), 7.68 (d, 1H, ArH), 7.79 (d, 1H, ArH), 8.24 (m, 1H, pyr-H), m.p. 176–177.5° C.

In a similar manner, by replacing 2-pyridylpiperazine with other piperazine derivatives, the following compounds were made:

3-[4-ethylpiperazinyl]-1,2,4-thiadiazolo[4,5-a] benzimidazole
$^1$H-NMR (CDCl$_3$)δ 1.15 (t, 3H, CH$_3$), 2.55 (q, 2H, CH$_2$), 2.70 (br. s, 4H, 2 CH$_2$), 3.49 (br.s, 4H, 2CH$_2$), 7.25 (m, 1H, ArH), 7.40 (m, 1H, ArH), 7.65 (d, 1H, ArH), 7.79 (d, 1H, ArH); m.p. 153–154.5° C.

3-[4-propylpiperazinyl]-1,2,4-thiadiazolo[4,5-a] benzimidazole
$^1$H-NMR (CDCl$_3$)δ 0.96 (t,3H, CH$_3$), 1.58 (m, 2H, CH$_2$), 2.45 (t, 2H, CH$_2$), 2.74 (br. s, 4H, 2CH$_2$), 3.49 (br. s, 4H, 2CH$_2$), 7.26 (t, 1H, ArH), 7.30 (t, 1H, ArH), 7.64 (d, 1H, ArH), 7.77 (d, 1H, ArH); m.p. 137–138° C.

3-[4-(2-hydroxyethyl)piperazinyl]-1,2,4-thiadiazolo [4,5-a] benz imidazole
$^1$H-NMR (CDCl$_3$)δ 2.65 (s, 1H, OH), 2.72 (t, 2H, CH$_2$) 2.84 (S, 4H, 2CH$_2$), 3.51 (s, 4H, 2CH$_2$) 3.70 (t, 2H, CH$_2$) 7.31 (t, 1H, ArH), 7.45 (t, 1H, ArH), 7.66 (d, 1H, ArH), 7.80 (d, 1H, ArH); m.p. 160–161.5° C.

3-[4-(3-chlorophenylpiperazinyl]-1,2,4-thiadiazolo[4,5-a] benzimidazole
$^1$H-NMR (CDCl$_3$)δ 3.37 (m, 6H, 3CH$_2$), 3.54 (m, 4H, 2CH$_2$), 6.88 (d, 1H, ArH), 7.04 (dd, 1H, ArH), 7.10 (br.s, 1H, ArH), 7.29 (t, 1H, ArH), 7.41 (t, 1H, ArH), 7.50 (t, 1H, ArH), 7.78 (d, 1H, ArH), 7.82 (d, 1H, ArH); m.p. 218.5–219.5° C.

3-[4-benzylpiperazinyl]-1,2-4-thiadiazolo[4,5-a] benzimidazole
$^1$H-NMR (CDCl$_3$)δ 2.76 (br.s, 4H, 2CH$_2$), 3.49 (br.s, 4H, 2CH$_2$), 3.66 (s, 2H, CH$_2$), 7.30–7.50 (m, 8H, ArH), 7.64 (d, 1H, ArH), 7.78 (d, 1H, ArH); m.p. 110–112.5° C.

3-[4-cinnamylpiperazine]-1,2-4-thiadiazolo[4,5-a] benzimidazole
$^1$H-NMR (CDCl$_3$)δ 2.81 (s, 4H, 2CH$_2$), 3.32 (d, 2H, CH$_2$), 3.51 (s, 4H, 2CH$_2$), 6.27–6.36 (m, 1H, CH), 6.60 (d, 1H, CH), 7.23– 7.46 (m, 7H, ArH), 7.65 (d, 1H, ArH), 7.79 (d, 1H, ArH) m.p. 120–121.5° C.

3-[4-(3-amino-2-pyridyl)piperazinyl]1,2,4-thiadiazolo[4,5-a]benzimidazole
$^1$H-NMR (CDCl$_3$)δ 3.42 (m, 4H, 2CH$_2$), 3.55 (m, 4H, 2 CH$_2$) 3.88 (s, 2H, NH$_2$), 6.92 (dd, J=4.74 HZ, 7.69 Hz, 1H, pyr-H-4), 7.02 (dd, J=1.57 Hz, 7.69 Hz, 1H, pyr-H-3), 7.30 (d, 1H), ArH), 7.44 (d, 1H, ArH), 7.76 (apparent br. t, 2H, ArH), 7.86 (dd, J=1.57 Hz, 4.78 Hz, 1H, pyr-H); m.p. 176–177.5° C.

3-[4-(1-(4-chlorophenyl)-1-phenylmethyl)piperazinyl]-1,2,4-thiadiazolo[4,5-a]benzimidazole
$^1$H-NMR (CDCl$_3$)δ 2.68 (br.s, 4H, 2CH$_2$), 3.49 (br.s, 4H, 2CH$_2$), 4.35 (s, 1H, CH), 7.2–7.5 (m, 11H, ArH), 7.59 (d, 1H, ArH), 7.79 (d, 1H, ArH); m.p. 172.5–174° C.

EXAMPLE 32

Synthesis of 3-[2-pyridylamino]-1,2,4-thiadiazolo[4,5-a] benzimidazole

To a cooled solution of 3-bromo-1,2,4-thiadiazolo[4,5-a] benzimidazole (0.30 g, 1.17 mmol) in 15 mL of dichloromethane, 2-aminopyridine (0.276 g, 2.93 mmol) was added dropwise and the mixture was allowed to stir for 48 h. The reaction mixture wad diluted with 100 mL of dichloromethane and washed with water (2×30 mL) and then brine (1×25 mL). The organic layer was dried over magnesium sulfate and evaporated to give a yellow solid (0.26 g, 83%) $^1$H-NMR (CDCl$_3$)δ 6.59 (apparent 5, 1H, pyr-H), 7.12 (apparent br. d, 1H, pyr-H), 7.28 (t, 1H, ArH), 7.38 (t, 1H, ArH), 7.51 (m, 2H, ArH & pyr-H), 7.70 (d, 1H, ArH), 8.28 (d, 1H, pyr-H); m.p. 155.5–157° C.

In a similar manner, by replacing 2-aminopyridine with other amine derivatives, the following compounds were made:

3-[3-pyridylamino]-1,2,4-thiadiazolo[4,5-a]benzimidazole
$^1$H-NMR (CDCl$_3$)δ 7.41 (t, 1H, ArH), 7.48 (t, 1H, ArH), 7.62 (dd, 1H, pyr-H), 7.75 (d, 1H, ArH), 8.34 (d, 1H, ArH), 8.44 (m, 2H, pyr-H), 9.02 (d, 1H, pyr-H); m.p. 175–176° C.

3-[2-pyridylmethylamino]-1,2,4-thiadiazolo[4,5-a] benzimidazole
$^1$H-NMR (CDCl$_3$)δ 2.02 (s, 1H, NH), 4.84 (d, 2H, CH$_2$), 7.22–7.56 (M, 4H, 2ArH & 2 Pyr-H), 7.75 (m, 2H, ArH & pyr-H), 7.85 (d, 1H, ArH), 8.66 (d, 1H, pyr-H); m.p. 155.5–157° C.

3-[N-methyl-(2-pyridylethyl)amino]-1,2,4-thiadiazolo[4,5-a]benzimidazole
$^1$H-NMR (CDCl$_3$)δ 3.11 (s, 3H, CH$_3$), 3.18 (t, 2H, CH$_2$), 3.87 9t, 2H, CH$_2$), 7.04–7.11 (m, 2H, pyr-H), 7.26 (m, 1H, Ar-H), 7.40 (t, 1H, ArH), 7.52 (m, 1H, pyr-H), 7.63 (d, 1H, ArH), 7.74 (1H, d, ArH), 8.41 (d, 1H, pyr-H); m.p. 105–107° C.

EXAMPLE 33

Synthesis of 3-bromomethyl-1,2,4-thiadiazolo[4,5-a] benzimidazole

A solution of 2-butyl-1,2,4-thiadiazolo[4,5-a]benzimidazole-3(2H)-one (15 g, 60.65 mmol) and bromoacetonitrile (18.19 g, 151.6 mmol) in dichloromethane (150 mL) was stirred for 48 h. A white precipitate was formed and the insoluble solid was filtered to give 12.50 g (77%) of the title compound: $^1$H NMR (CDCl$_3$)δ 4.79 (s, 2H, CH$_2$), 7.42 (t, 1H, ArH), 7.51 (t, 1H, ArH), 7.84 (d, 1H, ArH), 7.94 (d, 1H, ArH); mp 242–244° C.

EXAMPLE 34

Synthesis of 3-{[4-ethylpiperazinyl]methyl}-1,2,4-thiadiazolo [4,5-a]benzimidazole 1-Ethylpiperazine (0.732 ml, 6.03 mmol) was added to a suspension of 3-bromomethyl-1,2,4-thiadiazolo[4,5-a]benzimidazole (704 mg, 2.62 mmol) in dichloromethane (20 mL). The mixture was left stirring at room temperature for 26 hr. The material was diluted with dichloromethane (150 mL), and washed with water (15 mL) and brine (15 mL). The organic layer was dried over sodium sulfate and evaporated to give a solid which was recrystallized from acetonitrile (600 gm, 75.9% yield).

$^1$H-NMR (CDCl$_3$)δ 1.06 (t, 3H, CH,), 2.39 (q, 2H, CH$_2$) 2.44 (m, 4H, 2CH$_2$), 2.70 (m, 4H, 2CH$_2$), 3.90 (s, 2H, CH$_2$), 7.31 (t, 1H, ArH), 7.43 (t, 1H, ArH), 7.78 (d, 1H, ArH), 7.92 (d, 1H, ArH); m.p. 140–141.5° C.

In a similar manner, by replacing 1-ethylpiperazine with piperazine derivatives, the following compounds were made:

3-{[4-propylpiperazinyl]methyl}-1,2,4-thiadiazolo[4,5-a]benzimidazole $^1$H-NMR (CDCl$_3$)δ 0.89 (t, 3H, CH,), 1.51 (m, 2H, CH$_2$), 2.30 (t, 2H, CH$_2$), 2.50 (br.s, 4H, 2CH$_2$), 2.70 (s, 4H, 2CH$_2$), 3.99 (s, 2H, CH$_2$), 7.32 (t, 1H, ArH), 7.45 (t, 1H, ArH), 7.80 (d, 1H, ArH), 7.95 (d, 1H, ArH); m.p. 108–110° C.

3-{(4-(2-hydroxyethyl)piperazinyl]methyl}-1,2,4-thiadiazolo [4,5-a]benzimidazole $^1$H-NMR (CDCl$_3$)δ 2.55 (M, 6H, 2CH$_2$ of piperazine, CH$_2$), 2.70 (m, 4H, 2CH$_2$), 3.61 (m, 2H, CH$_2$), 3.99 (s, 2H, CH$_2$), 7.32 (t, 1H, ArH), 7.45 (t, 1H, ArH), 7.78 (d, 1H, ArH), 7.91 (d, 1H, ArH); m.p. 165–166.5° C.

3-{[4-phenylpiperazinyl]imethyl}-1,2,4-thiadiazolo[4,5-a]benzimidazole $^1$H-NMR(CDCl$_3$)δ 2.80 (m, 4H, 2CH$_2$), 3.20 (m, 4H, 2CH$_2$), 4.00 (s, 2H, CH$_2$), 6.90 (m, 3H, ArH), 7.25 (t, 4H, ArH), 7.50 (t, 1H, ArH), 7.80 (d, 1H, ArH), 8.00 (d, 1H, ArH); m.p. 197–197.5° C.

3-{[4-(4-amino)phenylpiperazinyl]methyl}-1,2,4-thiadiazolo [4,5-a]benzimidazole $^1$H-NMR (CDCl$_3$)δ 2.82 (m, 4H, 2 CH$_2$), 3.00 (m, 4H, 2CH$_2$), 3.31 (s, 2H, NH$_2$), 4.01 (s, 2H, CH$_2$), 6.63 (d, 2H, ArH), 6.78 (d, 2H, ArH), 7.32 (t, 1H, ArH), 7.45 (t, 1H, ArH), 7.80 (d, 1H, ArH), 7.98 (d, 1H, ArH); m.p. 199.5–200.5° C.

3-{[4-benzylpiperazinyl]methyl}-1,2,4-thiadiazolo[4,5-a]benzimidazole $^1$H-NMR (CDCl$_3$)δ 2.50 (br.s, 4H, 2CH$_2$), 2.68 (br.s, 4H, 2CH$_2$), 3.49 (s. 2H, CH$_2$), 3.98 (S, 2h, chb2), 7.30 (t, 6H, ArH), 7.46 (t, 1H, ArH), 7.79 (d, 1H, ArH), 7.94 (d, 1H, ArH); m.p. 120.5–122° C.

3-{[4-cinnamylpiperazinyl]methyl}-1,2,4-thiadiazolo[4,5-a]benzimidazole $^1$H-NMR (CDCl$_3$)δ 2.71 (m, 4H, 2CH$_2$ 2.55 (m, 4H, 2CH$_2$), 3.14 (d, 2H, CH$_2$), 3.98 (s, 2H, CH$_2$), 6.27 (d, 1H, CH), 6.49 (d, 1H, CH), 7.30–7.37 (m, 6H, ArH), 7.46 (t, 1H, ArH), 7.77 (d, 1H, ArH), 7.93 (d, 1H, ArH); m.p. 162–163° C.

3-{[4-(2-pyridyl)piperazinyl]methyl}-1,2,4-thiadiazolo [4,5-a]benzimidazole $^1$H-NMR (CDCl$_3$))δ 2.80 (m, 4H, 2CH$_2$), 3.60 (m, 4H, 2CH$_2$), 4.00 (s, 2H, CH$_2$), 6.60 (m, 2H, pyr-H), 7.31 (t, 1H, ArH), 7.45 (t, 2H, ArH), 7.80 (d, 1H, ArH); 7.98 (d, 1H, pyr-H), 8.18 (m, 1H, pyr-H); m.p. 214–214.5° C.

3-{4-(3-aamino-2-pyridyl)piperazinyl]methyl}-1,2,4-thiadiazolo[4,5-a]benzimidazole $^1$H-NMR (CDCl$_3$)δ 2.82 (br.s, 4H, 2 CH$_2$), 3.17 (br.s, 4H, 2CH$_2$), 3.79 (s, 2H, NH$_2$), 4.07 (s, 1H, CH$_2$), 6.84 (m, 1H, pyr-H), 6.94 (m, 1H, pyr-H), 7.30 (m, 1H, ArH), 7.50 (m, 1H, ArH) 7.79 (m, 2H, pyr-H, ArH), 8.0 (d, 1H, ArH); m.p. 214–215.5° C.

3-{[4-(4-methoxyphenyl)piperazinyl]methyl}-11,2,4-thiadiazolo[4,5-a]benzimidazole $^1$H-NMR (CDCl$_3$)δ 2.80 (m, 4H, 2CH$_2$), 3.10 (m, 4H, 2 CH$_2$)I 3.80 (s, 3H, OCH$_3$), 4.10 (s, 2H, CH$_2$), 6.80 (m, 4H, ArH), 7.30 (t, 1H, ArH), 7.50 (t, 1H, ArH), 7.80 (d, 1H, ArH), 8.00 (d, 1H, ArH); m.p. 202–204.5° C.

3-{[4-(1-(4-chlorophenyl)-1-phenylmethyl)piperazinyl]methyl}-1,2,4-thiadiazolo[4,5-a]benzimidazole $^1$H-NMR (CDCl$_3$)δ 2.44 (br.s, 4H, 2 CH$_2$), 2.68 (br.s, 4H, 2 CH$_2$), 3.99 (s, 2H, CH$_2$), 4.18 (s, 1H, CH), 7.20–7.40 (m, 10H, ArH), 7.50 (t, 1H, ArH), 7.79 (d, 1H, ArH), 7.91 (d, 1H, ArH); m.p. 82–84° C.

EXAMPLE 35

Synthesis of 3-dipropylaminomethyl-1,2,4-thiadiazolo[4,5-a]benzimidazole

Dipropylamine (0.64 mL, 4.67 mmol) was added to a suspension of 3-bromomethyl-1,2,4-thiadiazolo[4,5-a]benzimidazole (0.5 g, 1.87 mmol) in dichloromethane (40 mL). The mixture was left stirring at room temperature for 26 h. The material was diluted with dichloromethane (100 mL)), and washed with water (3×40 mL) and 10% sodium sulfate solution (15 mL). The organic layer was dried over magnesium sulfate and evaporated to give a solid which was recrystallized from acetonitrile (370 mg, 69% yield).

$^1$H-NMR (CDCl$_3$)δ 0.82 (t, 6H, 2CH$_3$), 1.50 (m, 4H, 2CH$_2$), 2.60 (m, 4H, 2CH$_2$), 4.11 (s, 2H, CH$_2$), 7.31 (t, 1H, ArH), 7.44 (t, 1H, ArH), 7.78 (d, 1H, ArH), 8.03 (d, 1H, ArH); m.p. 70-5–72.5° C.

In a similar manner, by replacing dipropylamine with other amine derivatives, the following compounds were made:

3-dimethylaminomethyl-1,2,4-thiadiazolo [4,5-a]benzimidazole $^1$H-NMR (CDCl$_3$)δ 2.41 (s, 6H, 2 CH,), 3.90 (s, 2H, CH$_2$), 7.32 (t, 1H, ArH), 7.44 (t, 1H, ArH), 7.76 (d, 1H, ArH), 7.99 (d, 1H, ArH); m.p. 134–135.5° C.

3-diethylaminomethyl-1,2,4-thiadiazolo[4,5-a]benzimidazole $^1$H-NMR (CDCl$_3$)δ 1.07 (t, 6H, 2CH$_3$), 2.73 (q, 4H, 2 CH$_2$), 4.08 (s, 2H, CH$_2$), 7.30 (m, 1H, ArH), 7.43 (m, 1H, ArH), 7.77 (d, 1H, ArH), 8.04 (d, 1H, ArH); m.p. 109–110.5° C.

3-dibutylaminomethyl-1,2,4-thiadiazolo[4,5-a]benzimidazole $^1$H-NMR (CDCl$_3$)δ 0.85 (t, 6H, 2CH$_3$), 1.26 (m, 4H, 2CH$_2$), 1.43 (m, 4H, 2 CH$_2$) 2.65 (m, 4H, 2CH$_2$) 4.10 (S, 2H, CH$_2$), 7.27 (t, 1H, ArH), 7.45 (t, 1H, ArH), 7.78 (d, 1H, ArH), 8.02 (d, 1H, ArH); m.p. 72–72.5° C.

3-(morpholinomethyl)-1,2,4-thiadiazolo[4,5-a]benzimidazole $^1$H-NMR (CDCl$_3$)δ 2.66 (m, 4H, 2 CH$_2$), 3.71 (m, 4H, 2 CH$_2$), 3.99 (s, 2H, CH$_2$) 7.33 (t, 1H, ArH), 7.45 (t, 1H, ArH), 7.80 (d, 1H, ArH), 7.91 (d, 1H, ArH); m.p. 145–147° C.

3-(imidazolylmethyl)1,2,4-thiadiazolo[4,5-a]benzimidazole $^1$H,NMR (CDCl$_3$)δ 6.35 (s, 2H, CH$_2$), 7.48 (t, 1H, ArH), 7.54 (t, 1H, ArH), 7.72 (d, 1H, ArH), 7.84 (m, 2H, ArH, Imd-H), 8.14 (d, 1H, ArH), 9.12 (d, 1H, ArH); m.p. 226–227° C.

3-(1,2,4-triazolylmethyl)-1,2,4-thiadiazolo[4,5-a]benzimidazole $^1$H-NMR (CDCl$_3$)δ 6.26 (s, 2H, CH$_2$), 7.39 (t, 1H, ArH), 7.50 (t, 1H, ArH), 7.80 (d, 1H, ArH), 8.04 (d, 1H, ArH), 8.10 (s, 1H, H of triazole), 8.83 (s, 1H, H of triazole); m.p. 204.5–206° C.

EXAMPLE 36

Synthesis of 3-(2-pyrazinyl)-1,2,4-thiadiazolo[4,5-a]benzimidazole

A mixture of 2-butyl-1,2,4-thiadiazolo[4,5-a]benzimidazole-3(2H)-one (300 mg, 1.213 mmol) and pyrazinecarbonitrile (319 mg, 3.03 mmol) in 8 mL of dicloromethane was stirred at room temperature for 36 hr. The precipitate was filtered and washed with dichloromethane to give 0.28 g (91%) of 3-(2-pyrazinyl)-1,2,4-thiadiazolo[4,5-a]benzimidazole as a white solid; $^1$H NMR (CDCl$_3$)δ 7.32 (t, 1H, ArH), 7.50 (t, 1H, ArH), 7.83 (d, 1H, ArH), 8.67 (d, 1H, ArH), 8.87 (br.d, 2H, py-H), 9.59 (s, 1H, py-H); mp 255–256.5° C.

EXAMPLE 37

Synthesis of 4-(2-pyridyl)piperazinylcarbonyl-1,2,4-thiadiazolo[4,5-a]benzimidazole 1,1-Carbonyldiimidazole (0.355 g, 2.19 mmol) was added to a solution of 2-carboxy-1,2,4-thiadiazolo[4,5-a] benzimidazole (0.3 g, 1.37 mmol) in DMF (10 mL). The resulting solution was stirred at 40° C. for 2 h. The reaction mixture gradually changed from a white suspension into a yellow solution. N-(2-pyridyl)piperazine (0.268 g, 1.64 mmol) was added to the reaction mixture. The resulting mixture was stirred at 40° C. for 3 h, and cooled. The material was diluted with dicloromethane (100 mL) wad washed with 1N HCl (40 mL), and then 5% NaOH (60 mL). The organic layer was dried over magnesium sulfate and evaporated to give the title compound as a solid (0.2 g, 40% yield).

$^1$H-NMR (CDCl$_3$)δ 3.69 (m, 2H, CH$_2$), 3.79 (m, 2H, CH$_2$), 4.05 (m, 4H, 2CH$_2$), 6.70 (m, 2H, pyr-H), 7.30 (t, 1H, ArH), 7.40–7.60 (m, 2H, ArH and pyr-H), 7.80 (d, 1H, ArH), 8.00 (d, 1H, ArH), 8.23 (m, 1H, pyr-H); m.p. 222–223.5° C.

In a similar manner, by replacing 4-(2-pyridyl) piperazine with other amine derivatives, the following compounds were made:

3-{4-(benzyl)piperazinylcarbonyl}-1,2,4-thiadiazolo[4,5-a]benzimidazole $^1$H NMR (CDCl$_3$)δ 2.72 (m, 4H, 2 CH$_2$), 3.60 (s, 2H, CH$_2$), 3.92 (m, 4H, 2CH$_2$), 7.31 (t, 7H, ArH), 7.46 (t, 1H, ArH), 7.80 (d, 1H, ArH), 7.98 (d, 1H, ArH); m.p. 230-5–231.5° C.

3-{4-methylpiperazinylcarbonyl}-1,2,4-thiadiazolo[4,5-a]benzimidazole $^1$H NMR (CDCl$_3$)δ 2.37 (s, 3H, CH,), 2.51 (t, 2H, CH$_2$), 2.60 (t, 2H, CH$_2$), 3.90 (t, 2H, CH$_2$), 3.96 (t, 2H, CH$_2$), 7.33 (t, 1H, ArH), 7.73 (t, 1H, ArH), 7.80 (d, 1H, ArH), 7.98 (d, 1H, ArH).

EXAMPLE 38

Synthesis of 3-(4-butylpiperazinyl)-1,2,4-thiadiazolo [4,5-a]benzimidazole

A mixture of potassium carbonate (700 mg, 5.06 mmol), butyl bromide (0.43 mL, 0.4 mmol), 3-piperazinyl-1,2,4-thiadiazolo[4,5-a]benzimidazole (798 mg, 3.07 mmol) in THF (15 mL) and DMSO (2 mL) was refluxed for 16 h. The solution was evaporated to dryness, the residue partitioned between dichloromethane and water. The organic layer was washed five times with water, dried over sodium sulfate and evaporated to give an oil. This oil was mixed with acetonitrile, an insoluble solid was formed which was filtered (595 mg). The solid was purified by chromatography to give the title compound which was recrystallized from hexane (5:95) (440 mg, 41%).

$^1$H-NMR (CDCl$_3$)δ 0.95 (t, 3H, CH$_3$), 1.30 (m, 2H, CH$_2$), 1.50 (m, 2H, CH$_2$), 2.40 (t, 2H, CH$_2$), 2.7 (m, 4H, 2CH$_2$), 3.5 (m, 4H, 2CH$_2$), 7.3 (t, 1H, ArH), 7.4 (t, 1H, ArH), 7.65 (d, 1H, ArH), 7.8 (d, 1H, ArH); m.p. 121–122.5° C.

EXAMPLE 39

Synthesis of 2-mercapto-5-(tert-butoxycarbonyl) aminobenzimidazole

A. A mixture of 2-mercapto-5-nitrobenzimidazole (10.0 g, 5 1.23 mmol) and iron fillings (8.0 g, 143.24 mmol) in ethanol (80 mL) and water (10 mL) was refluxed. Then, concentrated HCl (1.2 mL) was added dropwise in ca. 12 min. The resulting dark brown mixture was refluxed for a further 1.5 h then cooled in ice and neutralized with a saturated sodium bicarbonate solution to pH 7.0. The mixture was diluted with EtOH (50 mL), slurried with celite (0.82 g) and filtered over a bed of celite. The cake was washed with EtOH (3×100 mL). The combined filtrate was concentrated in vacuo to afford 9.2 g of a light brown solid. Crystallization from hot water gave the 2-mercapto-5-aminobenzimidazole (6.74 g, 80%) as a light brown solid.

$^1$H-NMR (DMSO)δ: 4.98 (br. s, 2H), 6.40–6.43 (m, 2H, Ar-H), 6.81–6.85 (d, J=9.0 Hz, 1H, Ar-H), 12.06 (br. s, 1H). $^{13}$C-NMR (DMSO)δ: 165.9 (CS), 144.9, 133.4, 123.6, 109.8, 94.4 IR (KBr, cm$^{-1}$): 3362, 3295, 3173, 1637, 1622, 1507.

B. A solution of 2-mercapto-5-aminobenzimidazole (22.0 g, 133.2 mmol) and di-tert-butyldicarbonate (30.52 g, 139.86 mmol) in anhydrous THF (200 mL) was stirred at room temperature for 16 h under a blanket of nitrogen.

THF was removed by evaporation under reduced pressure and the residue was crystallized from acetonitrile to afford the title compound (28.7 g, 80%) as a light yellow solid. $^1$H-NMR (DMSO)δ: 1.50 (s, 9H), 7.00 (d, J=8.6 Hz, 1H, Ar-H), 7.11 (dd, J=8.6 and 1.8 Hz 1H, Ar-H), 7.53 (s, 1H, Ar-H), 9.41 (br.s, 1H), 12.41 (br.s, 2H). $^{13}$C-NMR (DMSO) δ: 167.9 (CS), 152.9 (C=O), 134.9, 134.9, 132.5, 127.5, 113.3, 109.3, 99.5, 79.0 (C-0), 28.2 IR (KBr, cm$^{-1}$): 3300, 3127, 1724, 1706, 1623, 1530. M.p. 217.1–217.7° C. Elemental Analysis calc (found) %, C$_{54.32}$ (54.32); H 5.70 (5.71) and N 15.84 (15.85).

EXAMPLE 40

Synthesis of 5'-(tert-butoxycarbonyl)amino-2-butyl-3-oxo-2,3-dihydro-1,2,4-thiadiazolo-[4,5-a]benzimidazole and 6'-(tert-butoxycarbonyl)amino-2-butyl-3-oxo-2,3-dihydro-1,2,4-thiadiazolo-[4,5-a]benzimidazole A. To a slurry of 2-mercapto-5-(tert-butoxycarbonyl) aminobenzimidazole (11.46 g, 43.19 mmol) in o-xylene (50 mL) pre-heated to 100° C. was added n-butyl isocyanate (7.3 mL, 64.79 mmol) via syringe. The mixture was then heated at 145–150° C. for 1.5 h, then cooled to room temperature and diluted with hexane (200 mL). The solid was collected by suction filtration and dried under vacuum to afford 1-butylcarbonyl-2-mercapto-5-(tert-butoxycarbonyl) aminobenzimidazole (14.19 g, 95%). $^1$H-NMR (DMSO)δ: 0.94 (t, J=7.2 Hz, 3H), 1.20–1.60 (m, 4H, 2CH$_2$), 1.51 (s, 9H), 3.37–3.43 (m, 2H, CH$_2$N), 7.19–7.23 (dd, J=9.0 and 1.9 Hz, 1H, Ar-H), 7.64 (s, 1H), 7.96 (d, J=9.0 Hz, 1H, Ar-H), 9.59 (s, 1H), 10.22 (t, J=5.4 Hz, 1H, NHCH$_2$). Elemental Analysis calc (found %: C, 56.0 (55.8); H, 6.6 (5.7) and N, 15.4 (15.3).

B. A slurry of 1-butylcarbamoyl-2-mercapto-5-(tert-butoxycarbonyl)aminobenzimidazole (12.90 g. 34.50 mmol) in chloroform (50 mL) was cooled to −5° C. and triethylamine (9.9 mL, 70.79 mmol) was added in one portion. The resulting clear solution was stirred at ca. 0° C. for 45 min., then bromine (1.82 mL, 35.4 mmol) in chloroform (40 mL) was added dropwise over ca. 1.5 h.

After stirring for a further 15 min at 0° C., the mixture was allowed to warm to room temperature then diluted with chloroform (1.25 L). The organic phase was washed with brine (2×100 mL), dried over sodium sulfate, filtered and concentrated in vacuo. The residue was slurried in methanol (100 mL) and filtered. The off-white solid was collected and dried under vacuum to afford the title compounds as a mixture in ca. 85/15 ratio (by $^1$H-NMR).

The proton NMR spectra obtained by heating the samples were helpful in the assignment of the peaks in the aromatic region corresponding to the 2 isomers.

Isomer 1: $^1$H-NMR (DMSO)δ: 0.95 (t, J=7.2 Hz, 3H), 1.36–1.43 (q, J=6.8 Hz, 2H, CH$_2$N), 1.53 (S, 3H), 1.65–1.73 (m, 2H, CH$_2$), 3.73–3.78 (t, J=6.8 Hz, 2H, CH$_2$, N), 7.38 (d, J=8.7 Hz, 1H, Ar-H), 7.80 (d, J=8.6 Hz, 1H, Ar-H), 7.98 (s, 1H, Ar-H), 9.53 (s, 1H)

Isomer 2: $^1$H-NMR (DMSO)δ: 0.95 (t, J=7.2 Hz, 3H), 1.36–1.43 (q, J=7.4 Hz, 2H, CH$_2$CH$_3$), 1.53 (S, 9H), 1.65–1.73 (m, 2H, CH$_2$), 3.73–3.78 (t, J=6.8 Hz, 2H, CH$_2$N), 7.38 (d, J=8.7 Hz, 1H, Ar-H), 7.63 (d, J=8.6 Hz, 1H, Ar-H), 8.34 (s, 1H, Ar-H), 9.60 (s, 1H).

EXAMPLE 41

Synthesis of 5'amino-[3-(2-pyridyl)]-1,2,4-thiadiazolo [4,5-a]benzimidazole and 6'-amino-[3-(2-pyridyl)]-1,2,4-thiadiazolo[4,5-a]benzimidazole A. To a slurry of products from Example 40, part B (1.0 g, 2.76 mmol) in chloroform (5.0 mL) was added 2-cyanopyridine (0.575 g, 5.52 mmol) in one portion. The resulting mixture was refluxed for 5 h, then stirred at room temperature for 16 h.

Chloroform was removed under reduced pressure and the residue was slurried with diethyl ether (10 mL) and filtered. The off-white solid was collected and dried under vacuum. Thus, 0.68 g (67%) of 5'-(tert-butoxycarbonyl)amino-[3-(2-pyridyl)]-1,2,4-thiadiazolo [4,5-a]benzimidazole and 6'-(tert-butoxycarbonyl)amino-[3-(2-pyridyl)]-1,2,4-thiadiazolo[4,5-a]benzimidazole in ca. 1:1 ratio were obtained.

$^1$H-NMR (CDCl$_3$)δ: 1.56 (s, 9H), 6.67 (br.s. 1H, NH), 7.23–7.32 (m, 1H, py-H), 7.54–6.60 (m, 1H, Ar-H), 7.66–7.69 (d, J=8.7 Hz, 0.5H, Ar-H), 7.79 (d, J=1.9 Hz, 0.5H, Ar-H), 7.93–7.98 (t, J=8.0 Hz, 1H, py-H), 8.28–8.32 (m, 1H, py-H), 8.64 (d, J=9.0 Hz, 0.5H, Ar-H), 8.86–8.89 (dd, J=4.8 and 0.9 Hz, 0.5H, py-H), 8.98 (br.d, J=4.8 Hz, 0.5H, py-H) and 9.20 (br. s, 0.5H).

B. A slurry of the compounds obtained in Example 41, part A (1.0 g, 2.72 mmol) in a solution of HCl in MeOH (25 mL) were stirred at room temperature for 4.5 h. A further 25 mL of HCl in MeOH was added, and volatile materials were removed in vaccuo. The residue was slurried in diethyl ether and filtration afforded the title compounds as their light yellow HCl salts (0.99 g, 96.6%) in ca. a 1:1 mixture of isomers (by HPLC: 20 mM ammonium acetate/acetonitrile 80/20; C18 column). IR (KBr, cm$^{-1}$): 3419, 1611, 1551, 1527. Elemental Analysis: calc. (found) %: C, 41.5 (41.0); H, 3.2 (3.5) and N, 18.6 (18.3).

EXAMPLE 42

Synthesis of 1,2,4-thiadiazolo[4,5-a]benzimidazol-3-yl-L-leucyl isomylamide.

Potassium carbonate (544 mg, 3.94 mmol) was added to a solution of L-leucyl isoamylamide (0.788 g, 3.94 mmol) and 3-bromo-1,2,4-thiadiazolo[4,5-a]benzimidazole (1.0 g, 3.94 mmol) in THF (15 mL). The mixture was stirred at room temperature for 16 h and then refluxed for a further 8 h. The solvent was evaporated to dryness and the residue was partitioned between ethyl acetate (125 mL) and water (15 mL). The organic phase was washed with brine (10 mL), dried over sodium sulfate and evaporated to give a solid which was further purified by column chromatography (10% MeOH: CHCl$_3$) to give the title compound (715 mg).

$^1$H-NMR (CDCl$_3$)δ 0.92 (d, 6H, 2CH$_3$), 0.92–1.10 (dd, 6H, 2CH$_3$), 1.40–1.52 (m, 2H), 1.54–1.78 (m, 2H), 1.80–2.00 (m, 2H, CH$_2$), 3.34–3.45 (m, 2H, CH$_2$NH), 4.48–4.58 (m, 1H, α-CH of leu), 6.56 (t, J=5.6 Hz, 1H, NHCH$_2$), 6.60 (d, J=8.3 Hz, 1H, NHCH), 7.15 (t, 1H, J=7.4 Hz, Ar-H), 7.34 (t, 1H, J=8.2 Hz, Ar-H), 7.64 (d, 1H, J=8.2 Hz, Ar-H), 7.77 (d, 1H, J=8.1 Hz, Ar-H), $^{13}$C-NMR (CDCl$_3$)δ 172.5 (CO—CH), 164.4 (c-s), 150.4, 145.0, 127.8, 124.5, 121.3, 119.1, 110.2, 55.4 (CH—CO), 41.7, 38.4, 38.2, 25.8, 24.9, 23.0, 22.4, 22.1. IR (thin film, cm$^{-1}$): 3241 (NH), 1660 (C=O), 1574.

M.p. 105–107° C. Elemental Analysis: Calc. (found) %; C, 61.10 (61.30); H, 7.29 (7.05); N, 18.75 (18.43).

EXAMPLE 43

Synthesis of {1,2,4-thiadiazolo[4,5-a]benzimidazol-3-yl}-carbonyl-L-leucyl isoamylamide 1,1-Carbonyldimidazole (1.30 g, 8.03 mmol) was added to a suspension of 3-carboxy-1,2,4-thiadiazolo[4,5-a] benzimidazole (1.10 g, 5.02 mmol) in DMF (30 mL). The mixture was heated at 45° C. for 2 h at which time the mixture turned into a yellow solution. The solution was cooled to 0° C., leucyl isoamylamide (1.21 g, 6.02 mmol) and DMF (5 mL) were added and the resulting mixture was stirred for 16 h at R.T. The mixture wad diluted with ether (400 mL), and the ethereal layer washed with 0.5 M HCl (25 mL), water (3×25 mL), and brine (925 mL). The ethereal layer was dried over sodium sulfate, and evaporated to give a solid (1.77 g) which was further purified by column chromatography to give 1.33 g of the desired material.

$^1$H-NMR (CDCl$_3$)δ 0.90 (d, 6H, J=6.5 Hz, 2CH$_2$), 1.05 (dd, 6H, 2CH$_3$), 1.38–1.48 (m, 2H), 1.54–1.68 (m, 1H), 1.72–1.85 (m, 3H), 3.22–3.38 (m, 2H, CH$_2$NH), 4.62–4.78 (m, 1H, CHCO), 6.30 (t, 1H, NH), 7.32 (t, 1H, J=7.3 Hz, Ar-H), 7.45 (t, 1H, J=7.4 Hz, Ar-H), 7.75 (d, 1H, J=8.0 Hz, Ar-H), 7.93 (d, 1H, J=8.4 Hz, Ar-H), 8.73 (d, 1H, J=8.3 Hz, NH)

$^{13}$C-NMR (CDCl$_3$)δ 170.8 (COCH), 164.4 (CS), 155.4, 150.5, 144.1, 129.4, 125.8, 122,2, 119.1, 116.3, 52.6 (CHCO), 41.4, 38.3, 38.2, 25.8, 24.9, 22.9, 22.4, 22.1. IR (KBr, cm$^{-1}$): 3295 (NH), 1651 (C=O), 1527.

M.p. 164–167° C.

EXAMPLE 44

Synthesis of 5-amino-3-methoxy-1,2,4-thiadiazole

This material was prepared according to the procedure of J. Goeredeler et al., Chem. Ber., 1955,88, 843. Cyanamide (5.77 g, 13.78 mmol) was added slowly to a solution of HCl (5.77 g) in methanol (100 mL). The resulting mixture was stirred at room temperature for 3 days. The residue was evaporated under reduced pressure to give methylisourea hydrochloride (15.16 g). Sodium hypochlorite solution (0.769 M, 149 mL) was added dropwise to a solution of methylisourea hydrochloride (12.63 g, 0.114 mol) in water (75 mL) at 0° C. over 30 min. After 1.5 h, the solution was saturated with sodium chloride and extracted with ether (3×700 mL). The combined ethereal layer was dried over sodium sulfate and evaporated to give N-chloromethylisourea (10.26 g, 83% yield). KSCN (9.19 g, 94.5 mmol) was added to a solution of N-chloromethylisourea (10.26 g. 94.5 mmol) in methanol (200 mL). After 16 h, the insoluble residue was filtered and further washed with methanol. The combined filtrate was evaporated to give a solid which was purified by column chromatography (elution g r adient: 5 to 7% MeOH: CHCl$_3$). The isolated solid was recrystallized from toluene to give the title compound (3.14 g).

EXAMPLE 45

Synthesis of 5-{3-methoxy-1,2,4-thiadiazolyl}carbamoylisoleucyl isoamylamide

A solution of 5-amino-3-methoxy-1,2,4-thiadiazole (1.0 g, 7.67 mmol) in THF (20 mL) was added dropwise to a solution of triphosgene (0.837 g, 2.82 mmol) and dipropyl ethylamine (1.08 g, 8.35 mmol) at 15° C. and the resulting mixture was stirred at room temperature for 1 hr. A solution of leucyl-isoamylamide (1.53 g, 7.62 mmol) in dichloromethane (15 mL) was added over 15 min. After 2 h, the solvent was removed under reduced pressure, and the residue diluted with EtOAc (500 mL). The material was washed with ammonium sulfate solution (10%, 50 mL) and brine (50 mL). The organic layer was dried over sodium sulfate and evaporated to give an oil which was purified by column chromatography (1.5% MeOH:CHCl$_3$) to give the title compound (469 mg, 17% yield).

$^1$H-NMR (CDCl$_3$)δ 0.86 (d, J=6.55 Hz, 6H, 2CH$_3$), 0.93 (dd, 6H, 2CH$_3$), 1.34 (m, 2H), 1.53–1.73 (m, 4H, CH$_2$ of leu, CH$_2$ of isoamyl), 3.17–3.33 (m, 2H, CH$_2$NH), 4.10 (s, 3H, OCH$_3$), 6.58 (t, J=5.4 Hz, 1H, NHCH$_2$), 6.70 (d, J=8.6 Hz, 1H, NHCH), 12.60 (br.s, 1H, NHCO).

$^3$C-NMR (CDCl$_3$ 178.1 (C—OCH$_3$), 171.7 (CH—C═O), 166.0 (C—S), 1 5 3.9 (N—CO—N), 56.6 (CH$_3$O), 52.7 (CH—CO), 41.9, 38.2, 38.0, 2 5.8, 2 4.7, 22.8, 22.4, 22.3, 22.2. IR (Kbr, cm$^{-1}$): 3359 (NH), 1701 (C═O), 1680, 1645, 1554. M.p. 169–172° C.

EXAMPLE 46

Synthesis of 5-{benzyloxycarbonyl-L-phenylalanyl-L-alaniamido}-3-methoxy-1,2,4-thiadiazole EDCI (300 mg, 1.62 mmol) was added to a solution of HOBt (131 mg, 0.97 mmol) and carbobenzyloxy-L-phenylalanyl-L-alanine (300 mg, 0.81 mmol) in DMF (2 mL) at 0° C. After 25 min., 5-amino-3-methoxy-1,2,4-thiadiazole (140 mg, 1.05 mmol) was added and the solution was stirred at room temperature for 2 days. The material w as evaporated to dryness and extracted with ethyl acetate. The organic layer was dried over sodium sulfate and evaporated to give an oil which was chromatographed (10% MeOH:CH$_2$Cl$_2$) to yield 90 mg of solid material. The solid was further purified by thick layer chromatography (5% MeOH: CH$_2$Cl$_2$) to give 30 mg of the title compound.

$^1$H-NMR (MeOD)δ 1.42 (d, 3H, CH$_3$), 2.80–2.95 (dd, 1H, CH$_2$ of phe), 3.08–3.18 (dd, 1H, CH$_2$ of phe), 3.99 (s, 3H, CH$_3$O), 4.45 (dd, 1H, α-CH of phe), 4.58 (q, 1H, α-CH of ala), 5.05 (s, 2H, OCH$_2$), 7.10–7.40 (m, 10H, Ar-H)

$^{13}$C-NMR (MeOD)δ 177.3 (COCH$_3$), 174.4 (CO, 174.2 (CO), 169.5 (CS), 158.3 (CO$_2$), 138.2, 138.1, 130.4, 129.4, 128.9, 128.8, 128.7, 127.8, 127.7, 67.7 (OCH$_2$), 57.6 (CHCH$_2$), 57.1 (CH$_3$O), 39.0 (CH$_2$CH, 17.2 (CH$_3$CH)

EXAMPLE 47

Synthesis of N-[3-(4-methyl-piperazinyl-yl)-[1,2,4] thiadiazol-5-yl]-N-phenyl-benzamidine.

5-Cyanimino-4,5-dihydro-3,4-diphenyl-1,2,4-diphenyl-1, 2,4-thiadiazole was prepared according to the procedure of H. Sonnenschein et al., Liebigs Ann. Chem., 1992, 287–289. 1-Methylpiperazine (0.152 ml, 1.375 mmol) was added to a solution of 5-cyanimino-4,5-dihydro-3,4-diphenyl-1,2,4-thiadiazole (153 mg, 0.55 mmol) in dioxane (3 ml). The mixture was stirred at room temperature for 3 days. TLC (35% EtOAc:hexane) indicated reaction completion. A white solid was formed which was filtered and then recrystallized from dichloromethane:hexane (1:9). This gave 97 mg of the titled compound which was further purified by column chromatography (10% MeOH:CH$_2$Cl$_2$).

H-NMR (CDCll$_3$): 2.3 (s, 3H, OMe), 2.4 (m, 4H, 2CH$_2$), 3.5 (m, 4H, 2CH$_2$), 7.15–7.25 (m, 10H, ArH), 8.51 (s, 1H, NH) M.p.=152.5–152.7° C.

EXAMPLE 48

Acid stability of 7-methoxy-3-[(4-methoxy-3,5-dimethyl-2-pyridyl)oxomethyl]-1,2,4-thiadiazolo[4,5-a]benzimidazole.

To examine acid stability of the captioned compound, the compound was dissolved in a minimum volume of methanol and the resulting solution was added to a 6 molar solution of hydrochloric acid. The compound was found to be very stable in acid and was totally recovered after stirring for 48 hours at room temperature. Omeprazole, on the other hand, underwent complete decomposition in a few minutes under the above conditions. 1,2,4-Thiadiazole derivatives are superior to omeprazole as a direct thiol trapping agent in acidic medium because they are stable in acid.

EXAMPLE 49

Reaction of 3-[(4-methoxy-3,5-dimethyl-2-pyridyl) oxomethyl]-1,2,4-thiadiazolo[4,5-a]benzimidazole with 3-mercaptopropionic acid.

To a suspension of 250 mg of 3-[(4-methoxy-3,5-dimethyl-2-pyridyl)oxomethyl]-1,2,4-thiadiazolo[4,5-a] benzimidazole in 125 mL methanol and 38 mL 0.1 M hydrochloric acid was added 161 μL of 3-mercaptopropionic acid. After complete degradation of the starting material, the mixture was neutralized to pH 6 with aqueous sodium bicarbonate and extracted with ethyl acetate. The ethyl acetate was dried on anhydrous magnesium sulfate and evaporated. The crude material was purified by chromatography to give 93 mg of 2-imino-2-(2-mercapto-1-benzimidazolyl)-1-(4-methoxy-3,5-dimethyl-2-pyridyl) ethanone, 65 mg of 2-mercaptobenzimidazole and 61 mg of methyl 2-(4-methoxy-3,5-dimethyl-2-pyridyl)-2-oxoacetate. 2-Imino-2-(2-mercapto-1-benzimidazolyl)-1-(4-methoxy-3,5-dimethyl-2-pyridyl)ethanone: $^1$H NMR (CDCl$_3$)δ 10.55 (br s, 1H, NH or SH), 10.35 (br s, 1H, NH or SH), 8.10 (d, 1H, J=7 Hz, ArH), 7.80 (s, 1H, H6 of pyridyl), 7.35–7.20 (m, 2H, 2×ArH), 7.10 (d, 1H, J=7.9 Hz, ArH), 3.75 (s, 3H, OCH$_3$), 2.60 (s, 3H, ArCH$_3$), 2.15 (s, 3H, ArCH$_3$) ppm; IR (KBr)v 3262, 1691, 1635, 1502, 1458, 1396, 1328, 1272, 1247, 1004, 746 cm$^{-1}$; MS (electrospray) m/z 341 (MH$^+$), 191 (MH$^+$–2-mercaptobenzimidazole). 2-Mercaptobenzimidazole: the material was found to be identical to an authentic sample purchased from Aldrich Chemical Co. by $^1$H NMR, IR and TLC. Methyl 2-(4-methoxy-3,5-dimethyl-2-pyridyl)-2-oxoacetate:

$^1$H NMR (CDCl$_3$)δ 8.45 (s, 1H, ArH), 4.1 (s, 3H, OCH$_3$), 3.85 (s, 3H, OCH$_3$), 2.65 (s, 3H, ArCH$_3$), 2.4 (s, 3H, ArCH$_3$) ppm; IR (KBr)v 1747, 1703, 1468, 1394, 1310, 1242, 1206, 1120, 1004, 740 cm$^{-1}$; MS m/z 224 (M$^+$+H), 164 (M$^+$–CO$_2$Me), 136 (M$^+$–CO$_2$Me—CO)

EXAMPLE 50

Reaction of 3-(dimethylamino)-1,2,4-thiadiazolo[4,5-a] benzimidazole with phenethyl mercaptan.

To a solution of 23 mg of 3-(dimethylamino)-1,2,4-thiadiazolo[4,5-a]benzimidazole in 10 mL of methanol was added 360 μL of phenethyl mercaptan. After 1 min, the reaction is complete. The solvent was evaporated and the crude material was purified by chromatography to give 15 mg of N$^1$,N$^1$-dimethyl-2-mercapto-1-benzimidazolylamidine: $^1$H NMR (DMSO-d$_6$)δ 7.3–7.0 (m, 4H, 4×ArH), 3.35 (br s, 2H, NH, SH), 2.88 (s, 6H, 2×NCH$_3$) ppm; IR (KBr)v 3210, 1641, 1475, 1452, 1407, 1319 cm$^{-1}$; MS m/z 220 (M+), 150 (M$^+$–Me$_2$NC═NH)

EXAMPLE 51

Reaction of 3-bromo-1,2,4-thiadiazolo[4,5-a]benzimidazole with phenethyl mercaptan.

To a suspension of 500 mg of 3-bromo-1,2,4-thiadiazolo [4,5-a]benzimidazole in 50 mL methanol was added 790 μL of phenethyl mercaptan. The solid rapidly dissolves. After completion of the reaction, the solvent was evaporated and the residue purified by chromatography to give 296 mg of 2-mercapto-1-benzimidazolecarbonitrile:

$^1$H NMR (DMSO-d$_6$)δ 12.85 (br s, 1H, SH), 7.5–7.2 (m, 4H, 4×ArH) ppm; IR (KBr)v 2259, 1509, 1459, 1303, 1189, 752 cm$^{-1}$; MS m/z 175 (M$^+$), 150 (M$^+$–CN)

EXAMPLE 52

Reaction of 3-methoxy-1,2,4-thiadiazolo[4,5-a] benzimidazole with phenethyl mercaptan.

To a solution of 23 mg of 3-methoxy-1,2,4-thiadiazolo[4,5-a]benzimidazole in 10 mL of methanol was added 376 μL of phenethyl mercaptan. After 1 min, the reaction is complete. The methyl 2-mercapto-1-benzimidazolecarboximidate was identified as the major reaction product of the reaction: $^1$H NMR (DMSO-$d_6$)δ 13.45 (br s, 1H, SH or NH), 9.8 (s, 1H, NH or SH), 7.7 (d, 1H, J=8 Hz, ArH), 7.35–7.2 (m, 3H, 3×ArH), 3.95 (s, 3H, OCH$_3$) ppm; IR (KBr)ν 3437, 3095, 1679, 1450, 1440, 1376, 1193, 735 cm$^{-1}$; MS m/z=207 (M$^+$), 150 (M$^+$−MeOC=NH)

EXAMPLE 53

Reaction of 3-(oxophenylmethyl)-1,2,4-thiadiazolo[4,5-a] benzimidazole with phenethyl mercaptan To a suspension of 26 mg of 3-(oxophenylmethyl)-1,2,4-thiadiazolo [4,5-a]benzimidazole in 10 mL methanol was added 31 μL of phenethyl mercaptan. It was found that the substrate undergoes complete conversion to 2-mercaptobenzimidazole by comparing with an authentic sample of 2-mercaptobenzimidazole purchased from Aldrich Chemical Co.

EXAMPLE 54

Reaction of 3-Ehydroxy(4-methoxy-3,5-dimethyl-2-pyridyl) methyll-1,2,4-thiadiazolo[4,5-a]benzimidazole with phenethyl mercaptan.

To a suspension of 25 mg of 3-[hydroxy(4-methoxy-3,5-dimethyl-2-pyridyl)methyl]-1,2,4-thiadiazolo[4,5-a] benzimidazole in 10 mL methanol was added 250 μL of phenethyl mercaptan. It was found that the substrate undergoes complete conversion to 2-mercaptobenzimidazole by comparing with an authentic sample of 2-mercaptobenzimidazole purchased from Aldrich Chemical Co.

EXAMPLE 55

Reaction of 3-[(4-methylphenyl)sulfonyl]-1,2,4-thiadiazolo[4,5-a]benzimidazole with phenethyl mercaptan.

To a suspension of 31 mg of 3-[(4-methylphenyl)sulfonyl]-1,2,4-thiadiazolo[4,5-a]benzimidazole in 10 mL methanol was added 313 μL of phenethyl mercaptan. It was found that the substrate undergoes complete conversion to 2-mercaptobenzimidazole by comparing with an authentic sample of 2-mercaptobenzimidazole purchased from Aldrich Chemical Co.

EXAMPLE 56

Reaction of 5-amino-3-methoxy-1,2,4-thiadiazole with phenethyl mercaptan

To a solution of 250 mg of 5-amino-3-methoxy-1,2,4-thiadiazole in 10 mL methanol was added 1.3 mL of phenethyl mercaptan. After completion of the reaction, the solvent was evaporated. The crude material was purified by chromatography to give 236 mg of 3-carbamoylisourea. The structure of the compound was confirmed by X-ray crystallography:

$^1$H NMR (CDCl$_3$)δ 10 (br s, 1H, NH), 6.55 (br d, 2H, NH$_2$), 5.55 (br s, 1H, NH), 3.75 (s, 3H, OCH$_3$) ppm (in solution, the compound may exist in the 1-thiocarbamoylisourea tautomeric form to give 1 NH$_2$ and 2 NH in the NMR spectrum) IR (KBr)ν 3420, 3282, 3266, 3169, 1626, 1601, 1519, 1465, 1411, 1380, 1098 cm$^{-1}$; MS m/z 133 (M$^+$), 117 (M$^+$−NH$_2$), 100 (M$^+$−SH).

EXAMPLE 57

Reaction of 3-[(4-methoxy-3,5-dimethyl-2-pyridyl)oxomethyl]-1,2,4-thiadiazolo[4,5-a]benzimidazole with phenethyl mercaptan Phenethyl mercaptan (120 μL, 0.90 mmol) was added to a suspension of 3-[(4-4-methoxy-3,5-dimethyl-2-pyridyl)oxomethyl]-1,2,4-thiadiazolo[4,5-a]benzimidazole (300 mg, 0.887 mmol) in methanol (150 ml) and 0.1 M hydrochloric acid (38 mL). After stirring the mixture at room temperature for 51 h, the mixture was neutralized to pH 6 with aqueous sodium bicarbonate and extracted with ethyl ether. The ether layer was dried on sodium sulfate and evaporated. The crude material was purified by chromatography (elution gradient: 10% EtOAc:hexane to 30% EtOAc: hexane) to give 110 mg of diphenethyl disulfide (92% yield from phenethyl mercaptan), 63 mg of the methyl ester of 2-oxo-2-(4-methoxy-3,5-dimethyl-2-pyridyl)acetic acid (37.6% yield from consumed titled 1,2,4-thiadiazolo [4,5-a] benzimidazole), 44 mg of 3-[(4-methoxy-3,5-dimethyl-2-pyridyl)oxomethyl]-1,2,4-thiadiazolo[4,5-a]benzimidazole (14.6% recovered starting material) and 2-mercaptobenzimidazole (46 mg, 40% yield from titled 1,2,4-thiadiazolo [4,5-a]benzimidazole).

Methyl 2-oxo-2-(4-methoxy-3,5-dimethyl-2-pyridyl) acetate:

$^1$H NMR (CDCl$_3$)δ 8.45 (s, 1H, ArH), 4.1 (s, 3H, OCH$_3$), 3.85 (s, 3H, OCH$_3$), 2.65 (s, 3H, ArCH$_3$), 2.4 (s, 3H, ArCH$_3$) ppm; IR (KBr)ν 1747, 1703, 1468, 1394, 1310, 1242, 1206, 1120, 1004, 740 cm$^{-1}$; MS m/z 224 (M$^+$+HO, 164 (M$^+$−CO$_2$Me), 136 (M$^+$−CO$_2$Me—CO).

2-Mercaptobenzimidazole: the material was found to be identical to an authentic s ample purchased from Aldrich Chemical Co. by $^1$H NMR, IR and TLC.

Diphenethyl disulfide: H-NMR (CDCl$_3$): 3.03 (m, 8H, 2CH$_2$CH$_2$), 7.27 (m, 6H, ArH), 7.30 (m, 4H, ArH), C-NMR (CDCl$_3$: 35.79, 40.27, 126,46, 128.57, 128.67, 140.08.

EXAMPLE 58

Reaction of 3-(4-methyl-piperzinyl)-1,2,4-thiadiazolo[4,5-a]benzimidazole with thiophenol A solution of 3-(4-methylpiperazinyl)-1,2,4-thiadiazolo [4,5-a]benzimidazole dihydrochloride (1.494 g. 4.31 mmol) and thiophenol (1.43 ml, 12.94 mmol) in methanol (400 ml) and 1N HCl (120 ml) was stirred at room temperature for 3.5 days. The material was evaporated to give a solid residue which was partitioned between ether (3×100 ml) and water (20 ml). The ethereal layer was dried over sodium sulfate and evaporated to give 753 mg of diphenyl disulfide (53.3% yield). The aqueous layer was neutralized by dropwise addition of 2N NaOH at 0° C. and then extracted with dichloromethane (3×100 ml). The dichloromethane layer was dried over sodium sulfate and evaporated to give 1-[imino-(5-methyl-piperazine-1-yl) methyl-1H-benzimidazole-2-thiol as a solid (1.13 g, 95.1% yield).

H-NMR (DMSO): 2.19 (s, 3H, N—Me), 2.33 (br.s, 4H, 2CH$_2$CH$_2$—), 3.24 (br. s, 4H, 2CH$_2$CH$_2$—), 7.14–7.23 (m, 4H, ArH). C-NMR (DMSO): 44.81, 45.11, 53.59, 109.52, 110.42, 123.09, 123.89, 131.47, 131.57, 149-34 (C=NH), 166.89 (CSH).

EXAMPLE 59

Reaction of 3-benzoyl-1,2,4-thiadiazolo[4,5-a]benzimidazole with thiophenol

A solution of thiophenol (1.08 ml, 10.47 mmol), 3-benzoyl-1,2,4-thiadiazolo[4,5-a]benzimidazole (975 mg, 3.49 mmol) in methanol (400 ml) and 1N HCl solution (120 ml) was stirred at room temperature for 16 h. The solution was evaporated under reduced pressure to remove methanol;

the aqueous mixture was neutralized to pH 7.0 with solid sodium bicarbonate and extracted with $CH_2Cl_2$. The organic layer was dried over sodium sulfate and evaporated to give a solid. This material was purified by column chromatography to give the following compounds:

Diphenyl disulfide (700 mg solid; $R_1$=0.69, 106 EtoAc:hexane) which has identical NMR to diphenyl disulfide from Aldrich Chemical.

H-NMR ($CDCl_3$): 7.3–7.35 (m, 2H, ArH), 7.35–7.45 (m, 4H, ArH); 7.63–7.68 (m, 4H, ArH), C-NMR ($CDCl_3$): 127.326, 127.703, 129.241, 137.219.

2-mercaptobenzimidazole (180 mg, 34.3% yield; $R_1$=0.46, 20% EtOAc:hexane) which has identical NMR to 2-mercaptobenzimidazole from Aldrich Chemical. Methyl benzoylformate (120 mg, 21% yield; $R_1$=0.57, 206 EtOAc:hexane) which has identical NMR to methyl benzoylformate from Aldrich Chemical. H-NMR ($CDCl_3$): 52.67, 128.86, 130.03, 132.44, 134.89, 164.01 (C=O), 185.98 (C=O), IR: 1740, 1687, $cm^{-1}$.

EXAMPLE 60

Reaction of 1,2,4-thiadiazolo[4,5-a]benzimidazole derivative with 2-mercaptoethanol. Determination of $ti_{/2}$ values.

Calculated amount of the 1,2,4-thiadiazolo[4,5-a] benzimidazole derivative (final solution strength=$5 \times 10^{-3}$M) and phenol (118 mg, final solution strength=$5 \times 10^{-3}$M) were dissolved in of methanol (250 ml) in a volumetric flask. 100 ml of the solution was transferred to a clean volumetric flask, and the resulting solution was stirred at R.T. 100 µl of 2-mercaptoethanol (final solution strength=$1.15 \times 10^{-2}$M) was added within 60 sec with the tip of the syringe inserted into the solution. The course of the reaction was monitored by HPLC (Hewlett Packard Model 1100) equipped with a PE express 3.3 cm, C18 column and an UV detector set at 254 nm. The column is eluted with 70% 50 mM ammonium acetate; 30% acetonitrile as the mobile phase.

Percentage reaction completion was calculated as follows: At time 0, 100% starting material remained unreacted.

At time t, % of unreacted starting material={$h_{sample}/h_{int.std}$ at time t}/{$h_{sample}/h_{int.std}$ at time O}*100%.

The % unreacted starting material was plotted against the time scale, $t_{1/2}$ is the time point corresponding to 50% of unreacted starting material.

Reaction of tricyclic 1,2,4-thiadiazoles with mercaptoethanol at pH 7.0

| Y Group | $t_{1/2}$ at pH = 7.0 |
| --- | --- |
| MeO | 0.31 h |
| $Me_2N$ | 1.5 h |
| morpholino | 2.4 h |
| 4-methylpiperazinyl | 6.7 h |
| phenyl | 45 h |
| methyl | 59 h |
| 2-pyridyl | 134 h |
| acetyl | 110 h |
| morpholinomethyl | 98 h |
| dimethylaminoethyl | 64 h |

EXAMPLE 61

Effects of compounds of Formula I on Gastric Acid Secretions in Rats

Fasted, adult (140–240 g), male, Sprague-Dawley rats were fasted for 24 h from food, but not water, and then treated by oral gavage with 1 to 1.5 mL total volume of compound of Formula I (300 µmmol/Kg) on different days. Two hours later, rats were anesthetized with a combination of pentobartital and thiopental, the abdomen was opened and the pylorus was ligated, and tracheal, gastric, and peripheral venous canulas were placed. The stomachs were lavaged with 10 mL 0.9% saline every 10 min. for 30 min and the gastric effluent collected in receptacles to determine the basal acid secretion. Acid output was determined in each gastric effluent sample by back-titration to pH 7.0 using 0.02M NaOH. Then, 5 mL of an 8% peptone meal (pH 5.5) was instilled into the stomachs, mixed, and drained after 10 min each time for 2 hours. Acid output was determined in each gastric effluent containing the peptone meal by back-titration to pH 5.5 using 0.02 M NaOH.

In the controlled vehicle (n=6), 806 peptone stimulated acid output is noted at 160 numol/30 min after 1 hr., while rats dosed with 7-methoxy-3-[(4-methoxy-3,5-dimethyl-2-pyridyl)oxomethyl]-1,2,4-thiadiazolo[4,5-a]benzimidazole have an observed level of acid output at 20 µmmol/30 min after 1 h. 7-Methoxy-3-[(4-methoxy-3,5-dimethyl-2-pyridyl)oxomethyl]-1,2,4-thiadiazolo[4,5-a]benzimidazole demonstrated significant (p<0.05) inhibition of meal-stimulated acid secretion at 300 pmol/kg doses.

EXAMPLE 62

Effects of compounds of Formula I on Gastric Acid Secretions in Rats (Dose-dependent study)

Fasted, adult (140–240 g), male, Sprague-Dawley rats were fasted for 24 h from food, but not water, and then treated by oral gavage with 1 to 1.5 mL total volume of 4 different doses (0.3, 3, 30, and 300 µmol/kg) of each compound on different days. Two hours later, rats were anesthetized with a combination of pentobartital and thiopental, the abdomen was opened and the pylorus was ligated, and tracheal, gastric, and peripheral venous canulas were placed. The stomachs were lavaged with 10 mL 0.9% saline every 10 min. for 30 min and the gastric effluent collected in receptacles. Acid output was determined in each gastric effluent sample by back-titration to pH 7.0 using 0.02M NaOH. Then, 5 mL of an 80 peptone meal (pH 5.5) was instilled into the stomachs, mixed, and drained after 10 min each time for 2 hours. Acid output was determined in each gastric effluent sample by back-titration to pH 7.0 using 0.02 M NaOH. After measuring basal acid output for at least 30 minutes, acid output was then measured during a 2 h intravenous infusion of histamine (5 mg/kg).

Figure 3:
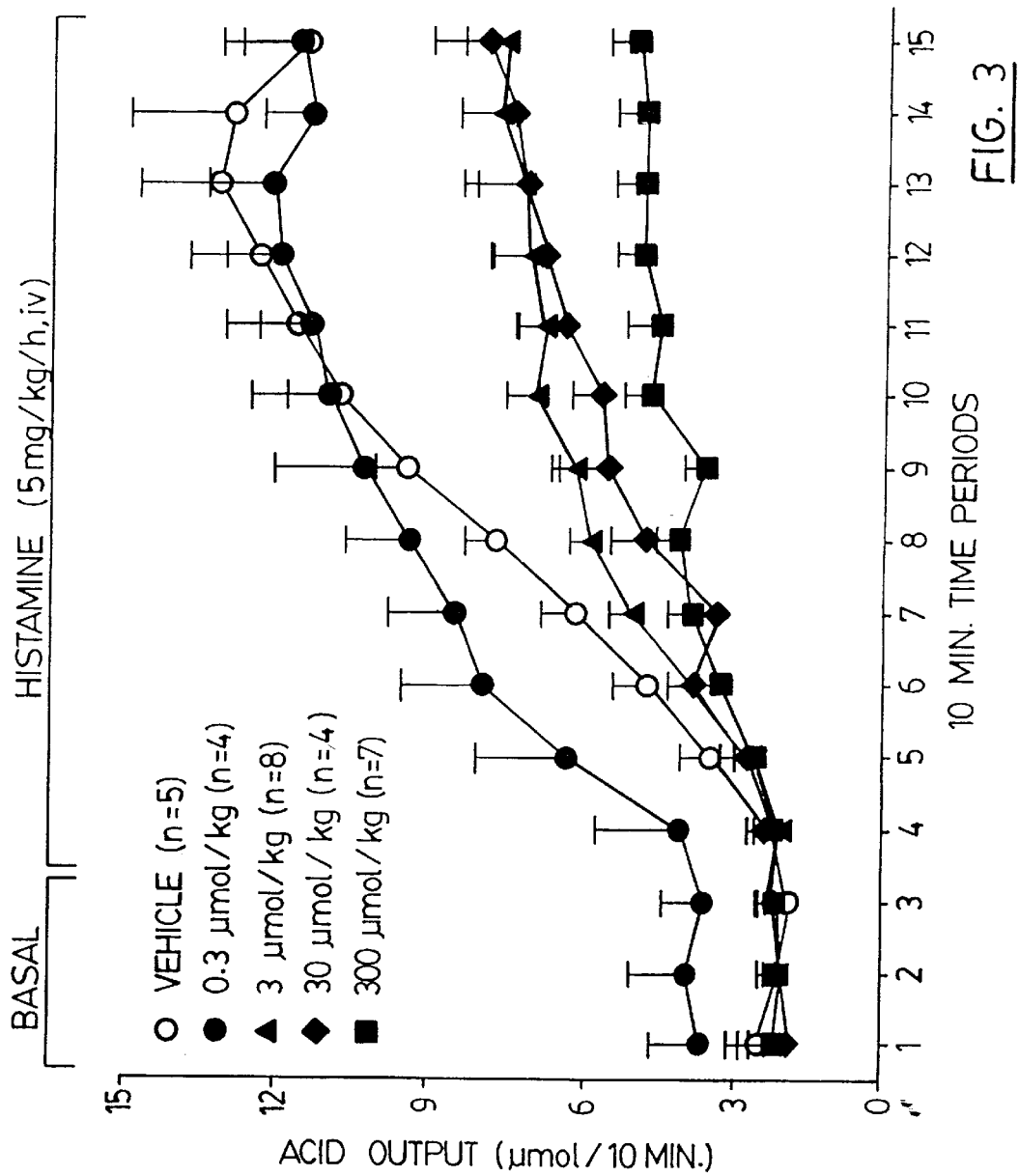
FIG. 3 is a graphical presentation of the results of Example 41 below.

FIG. 3 shows gastric acid output (mmol/min) after administration of vehicle and after administration of 4 doses of 7-methoxy-3-[(4-methoxy-3,5-dimethyl-2-pyridyl) oxomethyl]-1,2,4-thiadiazolo[4,5-a]benzimidazole (0.3, 3, 30, and 300 mmol/kg) in anesthetized rats.

7-methoxy-3-[(4-methoxy-3,5-dimethyl-2-pyridyl) oxomethyl]-1,2,4-thiadiazolo[4,5-a]benzimidazole demonstrated significant (p<0.05) inhibition of histamine-stimulated acid secretion at 3, 30, 300 µmol/kg doses.

EXAMPLE 63

In Vitro Inhibition of Gastric Acid Secretion By 3-(4-methyl-1-piperazinyl)-1,2,4-thiadiazolo[4,5-a] benzimidazole dihydrochloride Acid secretion is measured indirectly by the accumulation of the weak base $^{14}$C-aminopyrine in the isolated murine gastric glands of mouse. The assay is performed in polypropylene eppendorf tubes containing 0.5 mL of resuspended mouse gastric glands. In addition, tubes contain the tested drug, acid secretagogues (e.g. histamine, di-butyryl cyclic AMP (cAMP), carbachol) and $^{14}$C-aminopyrine. Tubes are incubated for 60 min. at 37° C. and continuously rotated. The reaction is stopped by centrifugation of the gland suspension for five min. at 1500 g. Supernatant is aspirated leaving the pellet containing intact gastric glands. The pellet is washed extensively and digested overnight in 1 mL of Protosol (Amersham). After neutralisation with acetic acid and addition of scintillation fluid, the radioactivity is counted in a beta-counter (Beckman). The amount of radioactivity trapped in the pellet corresponds directly with the amount of acid being secreted. Each experimental point is done in triplicate. In each experiment, energy independent consumption was estimated with 0.1 mM of dinitrophenol and basal acid secretion in the absence of acid stimulants. These values were then subtracted from corresponding results in order to calculate basal or secretagogue stimulated acid secretion.

Mouse glands respond to a variety of conventional secretagogues and post-receptor mediators but not to gastrin. The maximum stimulation of acid secretion is achieved with 1 mM cAMP, 0.1 mM histamine, 0.1 mM IBMX, 10 μM carbachol, 10 μM forskolin, 10 μM calcium ionophore A23187, 1 μM thapsigarin. Each experiment is repeated a number of times and all results are expressed as a % of the maximum stimulation. For the purpose of comparing the relative potency of the compounds, each experiment contains positive controls using omeprazole for post-receptor/cAMP mediated responses and ranitidine which inhibits histamine mediated acid secretion.

3-(4-Methyl-1-piperazinyl)-1,2,4-thiadiazolo[4,5-a]benzimidazole dihydrochloride completely inhibited cAMP and histamine stimulated acid secretion at 100 μM. Using the above procedure, the $ED_{50}$ value for this compound was found to be 50 μM.

EXAMPLE 64
Inhibition of Cathepsin B, Cathepsin L and Papain by 1,2,4-thiadiazoles and 1,2,4-thiadiazolo[4,5-a]benzimidazole derivatives: Enzyme Assays and Kinetic Measurements Conditions for the above experiments can be found in the following references: Menard R. et al., Biochemistry 1990, 29, 6706–6713; Fox T. et al., Biochemistry 1992, 31, 12571–12576; Cannona E. et al., Biochemistry 1996, 35, 8149–8157. A typical experiment consisted of choosing an inhibitor concentration such that maximum inhibition could be achieved in less than two hours, monitoring the complete progress curve (i.e. fluorescence vs time), and analyzing the data. The analysis yield two parameters: the % inhibition once steady state was re ached, and a rate constant which represents the rate at which this steady state is reached. Typically, the enzyme activity decreases with time until the maximum level of inhibition is reached (i.e. steady state) where the enzyme activity remains constant. Since significant levels of activity could still be detected at steady state (i.e. inhibition is not complete), the data was fitted to equation (1), which is normally used for slow-binding reversible inhibitors.

$$[P] = v_o \cdot t + \frac{(v_i - v_o)[1 - e^{-k_{abs} t}]}{k_{abs}} \quad (1)$$

$$\% \text{ inhibition} = (1 - v_i/v_o) \cdot 100 \quad (2)$$

In this equation, [P] represents the concentration of product (obtained from the flourescene readings), $k_{abs}$ is the first order rate constant to reach steady state, $v_o$ is the initial rate which corresponds to the rate in the absence of the inhibitor, and $v_i$ is the rate of the inhibited enzyme at steady state. The % inhibition was obtained by using equation (2), where the rate measured in the absence of the inhibitor was used for $v_o$. An example of a simple mechanism for such a process is given below:

For this mechanism, the value of $k_{abs}$ determined experimentally would correspond to:

$$k_{abs} = k_{on} \cdot [inh] + k_{off}$$

The value of $k_{abs}$ varies with inhibitor concentration. Often $k_{off}$ is much slower than $k_{on}[inh]$ and $k_{abs}/[inh]$ can be used to approximate $k_{on}$. This approach is used in this study and the results are shown in below:

3-[4-methylpiperazinyl]-1,2,4-thiadiazolo[4,5-a]benzimidazole
cathepsin L: 98% inhibition at 200 μm [inhibitor]; $k_{abs}/[inh]=24$ $M^{-1}s^{-1}$.
cathepsin B: 68% inhibition at 200 μm [inhibitor]; $k_{abs}/[inh]=19$ $m^{-1}s^{-1}$.
papain: 99% inhibition at 200 μm [inhibitor]; $k_{abs}/[inh]=28$ $M^{-1}s^{-1}$.

1,2,4-thiadiazolo[4,5-a]benzimidazol-3-yl carboxylic acid sodium salt
cathepsin L: 98% inhibition at 50 μM [inhibitor]; $k_{abs}/[inh]=184$ $M^{-1}s^{-1}$.
cathepsin B: 85% inhibition at 200 μM [inhibitor]; $k_{abs}/[inh]=34$ $M^{-1}s^{-1}$.
papain: 99.6% inhibition at 200 μM [inhibitor]; $k_{abs}/[inh]=131$ $M^{-1}s^{-1}$.

3-[2-pyridylcarbonyl]-1,2,4-thiadiazolo[4,5-a]benzimidazole
cathepsin L: 99% inhibition at 200 μM [inhibitor]; $k_{abs}/[inh]=68$ $M^{-1}s^{-1}$.
cathepsin B: 58% inhibition at 200 μM [inhibitor]; $k_{abs}/[inh]=15$ $M^{-1}s^{-1}$.
papain: 79% inhibition at 1 μM [inhibitor]; $k_{abs}/[inh]=2479$ $M^{-1}s^{-1}$.

3-[N-morholinomethyl]-1,2,4-thiadiazole[4,5-a]benzimidazole
cathepsin L: 806 inhibition at 200 μM [inhibitor]; $k_{abs}/[inh]=7$ $M^{-1}s^{-1}$.
cathepsin B: 60% inhibition at 200 μM [inhibitor]; $k_{abs}/[inh]=8$ $M^{-1}s^{-1}$.
papain: 92% inhibition at 200 μM [inhibitor]; $k_{abs}/[inh]=7$ $M^{-1}s^{-1}$.

1,2,4-thiadiazolo [4,5-a]benzimidazol-3-yl-L-proline methyl ester
cathepsin L: 99% inhibition at 10 μM [inhibitor]; $k_{abs}/[inh]=1050$ $M^{-1}s^{-1}$.
cathepsin B: 886 inhibition at 10 μM [inhibitor]; $k_{abs}/[inh]=626$ $M^{-1}s^{-1}$.
papain: 97% inhibition at 0.26 μM [inhibitor]; $k_{abs}/[inh]=356$ $M^{-1}s^{-1}$.

3-[2-(N-morpholino)ethoxy]-1,2,4-thiadiazolo[4,5-a]benzimidazole
cathepsin L: 99% inhibition at 25 μM [inhibitor]; $k_{abs}/[inh]=356$ $M^{-1}s^{-1}$.
cathepsin B: 91% inhibition at 50 μM [inhibitor]; $k_{abs}/[inh]=107$ $M^{-1}s^{-1}$.
papain: 99.6% inhibition at 0.66 μM [inhibitor]; $k_{abs}/[inh]=5560$ $M^{-1}s^{-1}$.

{1,2,4-thiadiazolo[4,5-a]benzimidazol-3-yl}-carbonyl-L-leucyl isoamylamide cathepsin L: 93% inhibition at 5 µM [inhibitor]; $k_{abs}$/[inh]= 307 $M^{-1}s^{-1}$.

papain: 95% inhibition at 5 µM [inhibitor]; $k_{abs}$/[inh]=500 $M^{-1}s^{-1}$.

5-{3-methoxy-1,2,4-thiadiazolyl}carbamoyl-isoleucyl isoamylamide cathepsin L: 99% inhibition at 5 µM [inhibitor]; $k_{abs}$/[inh]= 3482 $M^{-1}s^{-1}$.

cathepsin B: 56% inhibition at 5 µM [inhibitor]; $k_{abs}$/[inh]= 1062 $M^{-1}s^{-1}$.

papain: 97% inhibition at 1 µM [inhibitor]; $k_{abs}$/[inh]=3896 $M^{-1}s^{-1}$.

EXAMPLE 65

Crystal structure determination of enzyme inhibitor complex of 5-{3-methoxy-1,2,4-thiadiazolyl}carbamoyl-isoleucyl isoamylamide (T11AA) with papain and actinidin: T11AA/papain complex and T11AA/actinidin complex Purified papain was obtained commercially and purified actinidin was obtained by an aqueous extraction of homogenized Kiwifruit, followed by ammonium sulfate fractionation and DEAE ion-exchange chromatography. The actinidin/T11AA and papain T11AA reactions followed the same protocol. The mercaptoproteins were isolated by β-mercaptoethanol activated mercurial-agrose affinity chromatography. The proteins were eluted as mercurial derivatives. The mercurial-mercaptoproteins, at 0.1% w/v, were incubated with an 8-fold molar excess of T11AA and EDTA at pH 7.5. Papail/T11AA was redissolved at 2.5% w/v in 67% 2:1 methanol/ethanol, 76 mM NaCl, and 1 mM A100-73.

Papain T11AA crystals were grown by sitting-drop vapour diffusion. An aliquot of papain T11AA was incubated over a reservoir containing 67% 2:1 methanol/ethanol and 0.1 M ethanolamine buffer, pH 9.3 at 23° C. Large single crystals grew in 4 to 6 weeks.

Actinidin T11AA was redissolved at 0.5% w/v in 20 mM MES buffer, pH 6.0 and 0.5 mM T11AA. Actinidin T11AA crystals were grown by hanging drop vapour diffusion. A 1:1 mixture of actinidin T11AA and reservoir solution, which contained 20 mM MES buffer, pH 6.0 and 1.4 M ammonium sulfate, was incubated over the reservoir at 4° C. Large single crystals grew in 7 to 10 days.

The crystals were mounted in a wax-sealed glass capillary tubes containing mother liquor. The data were collected on a Siemens Multi-wire Detector mounted on a Rigaku RU200 X-ray generator. Three data sets were collected on one papain/T11AA crystal and two data sets were collected on two actinidin T11AA crystals. XDS was used for data reduction and the respective data sets were scaled together. The protein crystals had the following unit cell dimensions:

For papain/T11AA: a=42.9A, b=49.9A, c=95.7A, α=β=γ=90°.

For actinidin/T11AA: a=3.9A, b=77.9A, c=81.4A, α=β=γ=90°.

Both crystals had the space group $P2_12_12_1$. The papain/T11AA scaled data set was complete to a resolution of 2.2A (60% complete to 2.0A) with an overall Rsym=8.8%. The actinidin scaled data set was complete to a resolution of 2.7A with an overall Rsym=10%. XPLOR was used for structural refinements. 65 water molecules were modeled into the papain T11AA structure. For papain T11AA, the $R_{cryst}$=18.4% and the $R_{free}$=20.4%. For actinidin T11AA, the $R_{cryst}$=20.5% and the $R_{free}$=24.4%.

The electron density maps for the papain T11AA and actinidin T11AA complexes showed continuous electron density extending from their respective catalytic cysteine residues (Cys25). This demonstrated that T11AA reacted covalently with papain and actinidin to produce protein/inhibitor complexes. T11AA was completely modeled into the active site of papain whereas a partial model of T11AA was completed modeled into the active site of papain whereas a partial model T11AA in the actinidin active site was obtained.

Kinetic data showed complete inhibition of enzymatic activity in actinidin T11AA preparation and in redissolved actinidin T11AA crystals.

EXAMPLE 66

Gastric ATPase enzyme inhibition assay

The enzyme used is the hog $H^+/K^+$ ATPase (Sachs, et al. J. Biol. Chem. 251:7690–7698, 1976). A modified procedure reported by Yoda A. and Hokin, L.E., Biochem. Res. Commun., 1970, 800–884 is used. Potassium stimulated ATP hydrolysis using hog gastric (GI) vesicles, a preparation enriched in $H^+/K^+$ ATPase, is measured.

The difference between activity in the presence of $Mg^{++}$ and presence of $Mg^{++}$ and $K^+0$ is taken as enzyme activity. Nigericin, a $K^+$ ionophore, is also present in the (+)$K^+$ incubation mixture to provide access of $K^+$ to the vesicle interior. Hydrolysis activity is measured by quantitative analysis of a phosphomolybdate complex. This complex exhibits a maximal optical density at 320 nM. The optical density of many drugs used for the inhibition of $H^+/K^+$ ATPase interfere in this wavelength. Therefore, a modification of the as say was used wherein the phosphomolybdate complex was reduced with Fiske and Subbarow reducer (1-amino-2-naphthol-4-sulfuric acid plus sodium sulfite). This shifts the optical density from 3 20 nm for the oxidized phosphomolybdate complex to 600–700 nm. This modification has the added advantage of providing a means of automated assay when multiple samples being tested. In this modification, the optical density of the assay mixtures was read at 700 nm.

Basal $Mg^{++}$ levels are measured in 2 ml $MgCl_2$, 2 mM $Na_2ATP$, 40 mM Pipes-tris, pH 6.10. 20 mM KCl and 10 µg/ml nigericin is added to determine the extent of stimulation by $K^+$. Test compounds or vehicle are then added. Enzyme (10 µg/ml) is then added to initiate the reaction. The final volume is 200 µl. The protocol for these assays is shown below.

| | Volume per well | |
|---|---|---|
| Reagent[a] | $Mg^{2+}$ alone | $K^+$ plus Nigericin |
| 100 mM PIPES-Tris pH 6.1 | 80 µl | 80 µl |
| 20 mM $MgCl_2$ | 20 µl | 20 µl |
| 200 mM KCl | (—) | 20 µl |
| Nigericin (200 µl/ml) | 10 µl | 10 µl |
| Water | 20 µl | (—) |
| Vehicle, or solution containing test substance | | |
| 20 mM ATP[b] | 20 µl | 20 µl |
| Enzyme[c] | 20 µl | 20 µl |

[a]To reduce the number of additions, salt solutions and water can be combined as a single addition. Further reductions in the number of additions can be achieved by using enzyme to which nigericin (final concentration after addition of enzyme of 10 µg/ml).
[b]ATP must be prepared in ice cold distilled water immediately after addition.
[c]Enzyme must be thawed and diluted in buffer immediately before addition.

Zero blanks (water controls) and phosphate standards (200 µl) are added appropriate for assays used: 0.005, 0.01, 0.25, 0.050, 0.075, 0.1 . . . 0.5 mM standards. The order of the addition of reagents generally follows as described above. However, it may be more preferable to add either enzyme before ATP if it is important to provide time for pre-cubation with test compounds. Time additions of the last reagent are used to provide a uniform assay time.

The reaction is run for 30 min. to 1 hour. The re action is stopped by addition of 50 μl of a solution prepared by adding 4 volumes of 2.5 M sulfric acid plus one volume of 1.25% (w/v) Fiske and Subbarow reagent. Colour is developed at room temperature for ten minutes and optical density at 700 nm is determined. In the event that a white precipitate forms, the clear supernatants (after mixing and setting) can be used for the determination of enzyme activity.

3-[4-methylpiperazinyl]-1,2,4-thiadiazolo-[4,5-a] benzimidazole; $EC_{50}=2\times10^{-6}$ M.

3-[piperazinyl]-1,2,4-thiadiazolo-[4,5-a]benzimidazole; $EC_{50}=1\times10^{-6}$M.

3-[N-morpholinomethyl]-1,2,4-thiadiazole-[4,5-a] benzimidazole; $EC_{50}=2\times10^{-7}$ M.

3-[2-(N-morpholino)ethylamino]1,2,4-thiadiazolo-[4,5-a] benzimidazole; $EC_{50}=2\times10^{-7}$M.

What is claimed is:

1. 3,5-Disubstituted 1,2,4-thiadiazole compounds corresponding to the general formula:

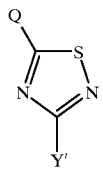

wherein Q represents a group —T—(—AMA—] L where T is a chemical spacer group bonded to the thiadiazole nucleus and selected from

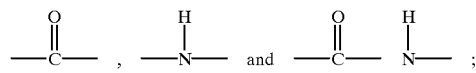

L is an N-terminal peptide protector group or a terminal group

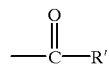

where R' and R" are as defined below in group Y' and —AMA— is an amino acid or peptide residue —[NH—CHA$^1$—CO]$_n$— where A$^1$ is any one of the known amino acid α-substituents and n is an integer from 1 to 3;

and Y' is lower alkyl, lower alkoxy, amino, carboxyl, or lower alkoxycarbonyl [or 1-piperazinyl; lower alkyl substituted with 1 or 2 substituents selected from hydroxy, lower alkylcarbamoyl, phenyl, halophenyl, heterocyclyl, carboxy and lower alkoxycarbonyl; benzyl; phenyl optionally substituted with amino, halo, hydroxy, lower alkoxy, lower alkyl, lower alkylamino, or di(lower alkyl)amino; heterocyclyl optionally substituted with 1–3 substituents selected from nitro, amino, halo, hydroxy, lower alkoxy, lower alkyl, lower alkylamino, or di(lower alkyl)amino; 1,1-diphenylmethyl wherein both phenyl rings are optionally substituted with halo, amino, hydroxy or lower alkoxy; 2-pyridyl where the pyridyl ring is optionally substituted with 1–3 substituents selected from nitro, amino, halo, hydroxy, lower alkoxy, lower alkyl, lower alkylamino, or di(lower alkyl)amino; or a group —CR$_2$—CO—NH-loweralkyl.

2. Compounds according to claim 1 wherein Q represents an amino acid residue of formula:

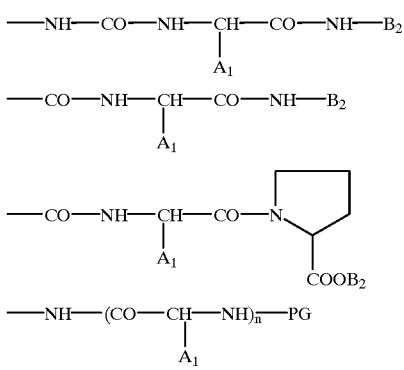

in which PG is an N-protective group selected from heterocyclylcarbonyl, benzoyl, carbobenzyloxy, and tert-butoxy; A, is lower alkyl; B$_2$ is lower alkyl optionally substituted with amino, guanidino or N,N-di-(loweralkyl) guanidino; and n is 1 or 2.

3. Compounds according to claim 2 wherein group Y' is selected from lower alkyl, lower alkoxy, amino, carboxyl and lower alkoxycarbonyl.

4. A compound according to claim 1 which is

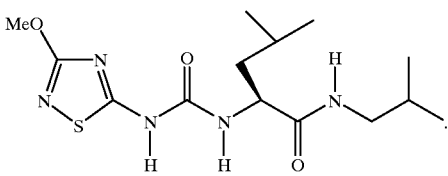

5. A compound according to claim 1 which is

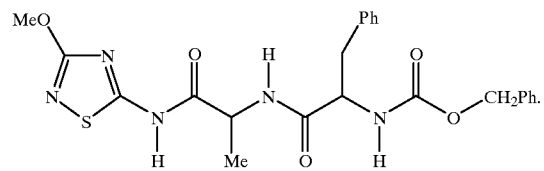

* * * * *

UNITED STATES PATENT AND TRADEMARK OFFICE
CERTIFICATE OF CORRECTION

PATENT NO. : 6,114,537
DATED : September 5, 2000
INVENTOR(S) : Karimian et al.

It is certified that error appears in the above-identified patent and that said Letters Patent is hereby corrected as shown below:

Column 2,
Line 51, the chemical formula NHC(O)NR'RR" should be -- NHC(O)NR'R" --.

Column 4,
Lines 40 to 44, replace:

with:

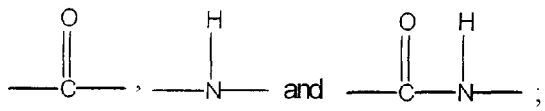

Column 5,
Lines 35 through 40, replace:

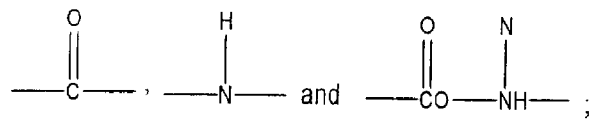

with:

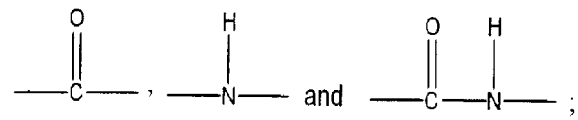

UNITED STATES PATENT AND TRADEMARK OFFICE
CERTIFICATE OF CORRECTION

PATENT NO.    : 6,114,537
DATED         : September 5, 2000
INVENTOR(S)   : Karimian et al.

It is certified that error appears in the above-identified patent and that said Letters Patent is hereby corrected as shown below:

Column 56,
Line 12, the word "-CR$_2$-" should read -- -CH$_2$- --.
Line 34, the word "A," should be -- A$_1$ --.

Signed and Sealed this

Tenth Day of September, 2002

Attest:

Attesting Officer

JAMES E. ROGAN
*Director of the United States Patent and Trademark Office*